(12) United States Patent
Eriksson et al.

(10) Patent No.: US 11,352,420 B2
(45) Date of Patent: Jun. 7, 2022

(54) METHODS AND COMPOSITIONS FOR PDGF-CC INHIBITION

(71) Applicant: Paracrine Therapeutics AB, Balsta (SE)

(72) Inventors: Ulf Eriksson, Balsta (SE); Hong Li, Sollentuna (SE); Andrew Scott, Kew East (AU); Laura Allan, St. Helena (AU)

(73) Assignee: PARACRINE THERAPEUTICS AB, Bålsta (SE)

( * ) Notice: Subject to any disclaimer, the term of this patent is extended or adjusted under 35 U.S.C. 154(b) by 124 days.

(21) Appl. No.: 16/312,843

(22) PCT Filed: Jun. 30, 2017

(86) PCT No.: PCT/US2017/040170
§ 371 (c)(1),
(2) Date: Dec. 21, 2018

(87) PCT Pub. No.: WO2018/005904
PCT Pub. Date: Jan. 4, 2018

(65) Prior Publication Data
US 2021/0179701 A1    Jun. 17, 2021

Related U.S. Application Data

(60) Provisional application No. 62/357,536, filed on Jul. 1, 2016.

(51) Int. Cl.
*C07K 16/22* (2006.01)
*A61K 39/00* (2006.01)

(52) U.S. Cl.
CPC ........ *C07K 16/22* (2013.01); *A61K 2039/505* (2013.01); *C07K 2317/24* (2013.01); *C07K 2317/33* (2013.01); *C07K 2317/34* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,603,931 A | 2/1997 | Raso | |
| 7,294,753 B2 | 11/2007 | Kloetzer et al. | |
| 10,647,768 B2 * | 5/2020 | Johnson | A61P 13/08 |
| 2004/0234519 A1 | 11/2004 | Tso et al. | |
| 2005/0282233 A1 | 12/2005 | Eriksson et al. | |
| 2006/0127893 A1 | 6/2006 | Ewert et al. | |
| 2006/0191024 A1 | 8/2006 | Kloetzer et al. | |
| 2010/0233180 A1 | 9/2010 | Khoshnan et al. | |
| 2014/0206847 A1 | 7/2014 | Endoh | |
| 2014/0255397 A1 | 9/2014 | Eriksson et al. | |
| 2015/0167015 A1 | 6/2015 | Poraty-Gavra et al. | |

FOREIGN PATENT DOCUMENTS

| | | |
|---|---|---|
| WO | 00/18212 A2 | 4/2000 |
| WO | 2000/43774 A2 | 7/2000 |
| WO | 2007/022287 A2 | 2/2007 |
| WO | 2007/142277 A1 | 12/2007 |
| WO | 2008/133857 A1 | 11/2008 |
| WO | 2011/046309 A2 | 4/2011 |
| WO | 2013/099043 A1 | 7/2013 |
| WO | 2013/160359 A1 | 10/2013 |
| WO | 2015/089449 A2 | 6/2015 |
| WO | 2016/092096 A1 | 6/2016 |

OTHER PUBLICATIONS

Ohno et al., Proc. Natl. Acad. Sci. USA, vol. 82, pp. 2945-2949, May 1985.*
Tas, JM, et al. Mus Musculus Clone D6H0519P3D12 Immunoglobulin Heavy Chain Variable Region (Igh) mRNA, Partial cds. Science. Mar. 9, 2016, vol. 351; pp. 1048-1054; mRNA sequence, 318 bp; Accession No. KU615284.1.
R&D Systems, Human PDGF-C Antibody, MAB1560, Jul. 5, 2015 (Year:2015) https://www.mdsystems.com/products/human-pdgf-c-antibody-619346_mab1560, 7 pages.
Office Action dated Sep. 23, 2021 in U.S. Appl. No. 15/774,341, 22 pages.

* cited by examiner

*Primary Examiner* — Marianne P Allen
(74) *Attorney, Agent, or Firm* — Fox Rothschild LLP

(57) ABSTRACT

The present invention relates, in part, to isolated antibodies that specifically interact with and show measurable binding affinity to an epitope of platelet derived growth factor C (PDGF-C). Such antibodies may be used for the modulation of PDGF-C activity in or secreted from a cell to study its effects on cell function and, in certain embodiments, for the treatment and/or prevention of a disease or condition associated with PDGF-C signing pathway.

2 Claims, 29 Drawing Sheets

Specification includes a Sequence Listing.

CLUSTAL 2.1 multiple sequence alignment

```
6B3LC      DIVMTQSPSSLAVSVGQRVTMSCKSSQSLLNSRNQKNYLAWYQQKPGQSPKLLIYFASTR   60
19C7LC     DIVMTQSPSSLAVSVGQKVTMSCKSSQSLLNSRNQKNLLAWYQQKPGQSPKLLVYFASTR   60
11F5LC     DIVMTQSPSSLAVSVGQKTAVSCKSSQSLLNSSNQKNYLAWYQQKPGQSPKLLIYFASTR   60
12F5LC     DVVMTQTPLSLPVSLGDQASISCRSSQSIVHS-WGNTYLEWYLQKPGQSPKLLIYKVSNR   59
                 **:*. ::.:*. : :.*:*.*::. .**  :* **:****:***** *. ::*

6B3LC      ESGVPDRFTGSGSGTDFTLTISSVQAEDLAVYYCQQRYSTPLTFGAGTKLELKR        114
19C7LC     ESGVPDRFTGSGSGTDFTLTISSVQAEDLAVYYCQQHYSTPLTFGAGTKLELKR        114
11F5LC     DSGVPDRFTGSGSGTDFTLTISSVQAEDLAVYYCQQHYSTPLTFGAGTKLELKR        114
12F5LC     FSGVPDRFSGSGSGTDFTLKISRVEAEDLGVYYCFQGSHVPLTFGSGTKLEIKR        113
           .******:*******:*** ** *:****.**** * . : ****:****:**
```

Legend:

"*"  Fully conserved residue
":"  Strongly conserved residue
"."  Weakly conserved residue
"-"  Indicates gap in sequence Underlined Sequence: CDR designation by Kabat and Chothia numbering.

Light Chain Variable Regions with CDR regions underlined

CLUSTAL 2.1 multiple sequence alignment

```
mu6B3LC    DIVMTQSPSSLAMSVGQKVTMSCKSSQSLLNSRTRKNYLAWYQQKPGQSPKLLVYFASTR  60
ch6B3LC    DIVMTQSPDSLAVSLGERATINCKSSQSLLNSRTRKNYLAWYQQKPGQSPKLLIYFASTR  60
           ******** ***.* *.:: *:.*********.*************:*****
```

```
mu6B3LC    ESGVPDRFTGSGSGTDFTLTISSVQAEDLAVYYCQQHYSTPLTFGAGTKLELKR  114
ch6B3LC    ESGVPDRFSGSGSGTDFTLTISSLQAEDVAVYYCQQHYSTPLTFGQGTKLELKR  114
           ********:*************..****:*************:******
```

Heavy Chain Variable Regions with CDR regions underlined

CLUSTAL 2.1 multiple sequence alignment

```
mu6B3HC    QVQLQQSGPELVRPGASVKLSCKASGYTFTSYGIVWVRQRTGQGLEWIGEIYPRSGKTYY  60
ch6B3HC    QVQLVQSGAEVKKPGASVKVSCKASGYTFTSYGISWVRQAPGQGLEWMGWINTYTGEPTY  60
           **** *** :*::*****:*******.*****: ****  ******:* *:.::..:.
```

```
mu6B3HC    NEKFKGKATLTADKSSSTVYMELRSLTSEDSAVYFCAREGIGDGGYEDYWGQGTTLTVS  120
ch6B3HC    AQKFQGRVTMTTDTSTSTAYMELRSLRSDDTAVYYCAREGIGDGGYEDYWGQGTLVTVS  120
           ::**:*:.*:*:* *:**.******* *:*:***:****************** :***
```

```
mu6B3HC    S 121
ch6B3HC    S 121
```

Legend:

"*" Fully conserved residue
":" Weakly conserved residue
Underlined Sequence: CDR designation by Kabat and Chothian numbering

FIG. 5

*Homology of Protein Sequence 231-345 in PDGFC with PDGFD*

KEY: Shaded amino acid: homologous amino acids in PDGFC and PGDFD
Boxed sequence: 6B3 Epitope Peptide Sequence

231 RKSRVWDLNLLTEEVRLYSCTPRMFSVSL

A.
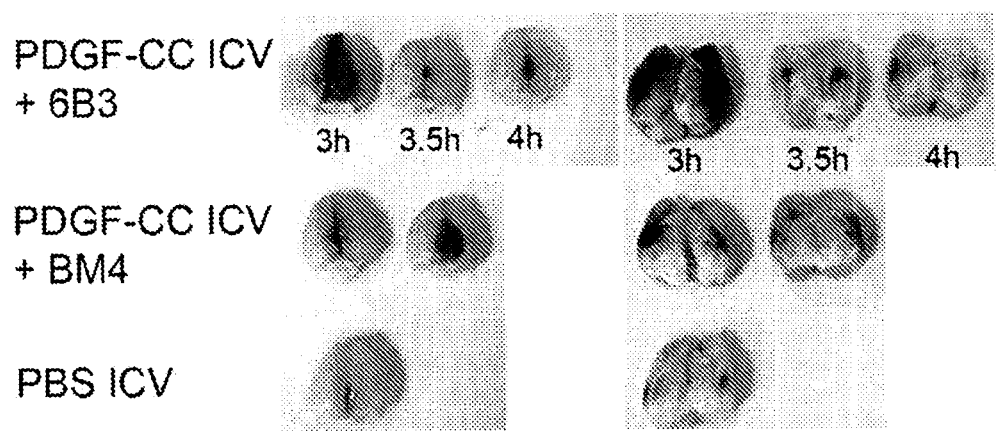
B.
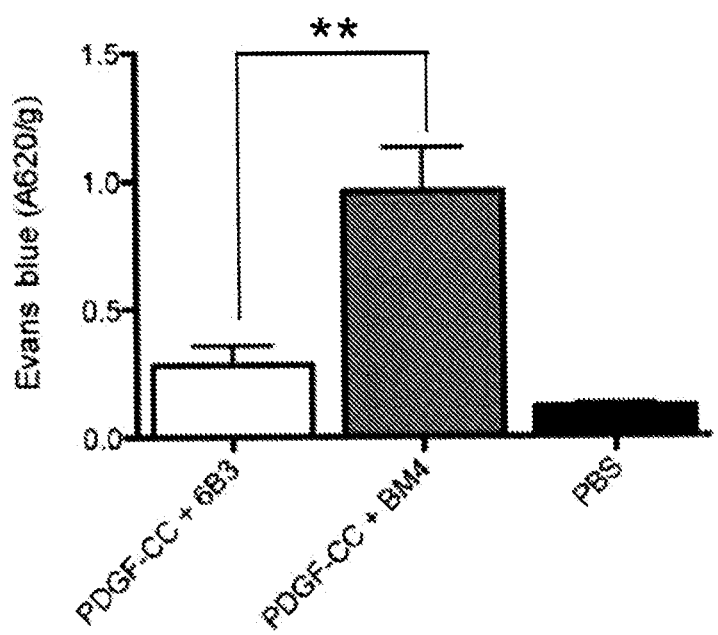
FIG. 18

Mouse  gkkakvvnlnllkeevklyscctpznfsvairoelkrtdclfwpgcllvkrcggncacclhncneocqcvprk
Human  grtsrvvdlnllteevrlyscctpznfsvairoelkrtdclfwpgcllvkrcggncacclhncneocqcvpak
       *    *********************************************************

Mouse  vtkkyhevlglrpktgvkglnksltdvalenheecdcvcrgnagg
Human  vtkkyhevlglrpktgvrglnksltdvalenheecdcvcrgstgg
       ******************:**********

Figure 19

```
MLLLGLLLLT  SALAGQRTGT  RAESNLSSKL  QLSSDKEQNG
VQDPRHERVV  TISGNGSIHS  PKFPHTYPRN  MVLVWRLVAV
DENVRIQLTF  DERFGLEDPE  DDICKYDFVE  VEEPSDGSVL
GRWCGSGTVP  GKQTSKGNHI  RIRFVSDEYF  PSEPGFCIHY
SIIMPQVTET  TSPSVLPPSS  LSLDLLNNAV  TAFSTLEELI
RYLEPDRWQV  DLDSLYKPTW  QLLGKAFLYG  KKSKVVNLNL
LTEEVRLYSC  TPRNFSVSIR  EELKRTDTIF  WPGCLLVKRC
GGNCACCLHN  CNECQCVPSK  VTKKYHEVLQ  LRPKTGVRGL
HKSLTDVALE  HHEECDCVCR  GSTGG
```

Figure 20

CLUSTAL O(1.2.1) multiple protein sequence alignment of mu6B3 and hu6B3 light chain variable region sequences.

```
mu6B3LC    DIVMTQSPSSLAMSVGQKVTMSCKSSQSLLNSRNQKNYLAWYQQKPGQSPKLLVYFASTR
hu6B3LC    DIVMTQSPSSLAMSVGERATINCKSSQSLLNSRNQKNYLAWYQQKPGQPPKLLIYFASTR
           ****************:  :.*:.*********************.:.**** mu6B3LC    ESGVPDRFTGSGSGTDFTLTISSVQAEDLAVYYCQQHYSTPLTFGAGTKLELKR
hu6B3LC    ESGVPDRFSGSGSGTDFTLTISSVQAEDVAVYYCQQHYSTPLTFGGGTKVELKR
           ********:*******************:*********************.***:****
```

Legend:

"*" Fully conserved residue
":" Strongly conserved residue
"." Weakly conserved residue
"-" Indicates gap in sequence Underlined Sequence: CDR designation by Kabat and Chothia numbering

Fig. 25

CLUSTAL O(1.2.1) multiple protein sequence alignment of heavy chain variable region of mu6B3 and hu6B3 HC 'R' sequences

```
mu6B3HC    QVQLQQSGVEVARPGASVKLSCKASGYTFRSYGITWVRQRTGQGLEWIGEIYPRSGKTYY
hu6B3HCR   QVQLVQSGAEVKKPGASVKVSCKASGYTF*SYGITWVRQATGQGLEWMGEIYPRSGKTGY
           **  * * * * ****  *   **** ****** * mu6B3HC    NEKFKGKATLTADTSSSTVYMELRSLTSEDSAVYFCAREGYGYDGGYFDYWGQGTTLTVS
hu6B3HCR   AQKFQGRVTMTADTSTSTVYMELRSRSEDSAVYFCAREGYGYDGGYFDYWGQGTLVTVS
            ***  * ***** ***** ************************ ** mu6B3HC    S
hu6B3HCR   S
           *
```

Legend:

"*" Fully conserved residue
":" Strongly conserved residue
"." Weakly conserved residue
"-" Indicates gap in sequence Underlined Sequence: CDR designation by Kabat and Chothia numbering

Fig. 26A

CLUSTAL O(1.2.1) multiple protein sequence alignment of heavy chain variable region mu6B3 and hu6B3 HC 'G' sequences.

```
mu6B3HC    QVQLQQSGVEVARPGASVKLSCKASGYTFRSYGITWVRQRTGQGLEWIGEIYPRSGKTYY
hu6B3HCG   QVQLVQSGAEVKKPGASVKVSCKASGYTFGSYGITWVRQATGQGLEWMGEIYPRSGKTGY
           **  *.  :***:***  *******  ***:*****  * mu6B3HC    NEKFKGKATLTADTSSSTVYMELRSLTSEDSAVYFCAREGYGYDGGYFDYWGQGTTLTVS
hu6B3HCG   AQKFQGRVTMTADTSTSTVYMELRSRSEDSAVYFCAREGYGYDGGYFDYWGQGTLVTVS
            :**:*: .*:***:**** :****************************  :* mu6B3HC    S
hu6B3HCG   S
           *
```

Legend:

"*" Fully conserved residue
":" Strongly conserved residue
"." Weakly conserved residue
"-" Indicates gap in sequence Underlined Sequence: CDR designation by Kabat and Chothia numbering

Fig. 26B

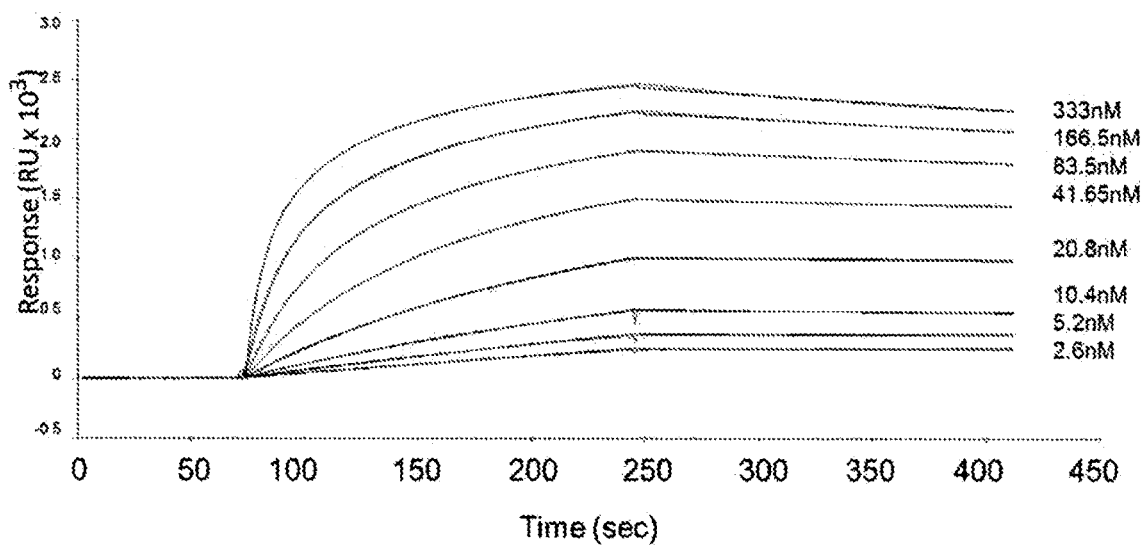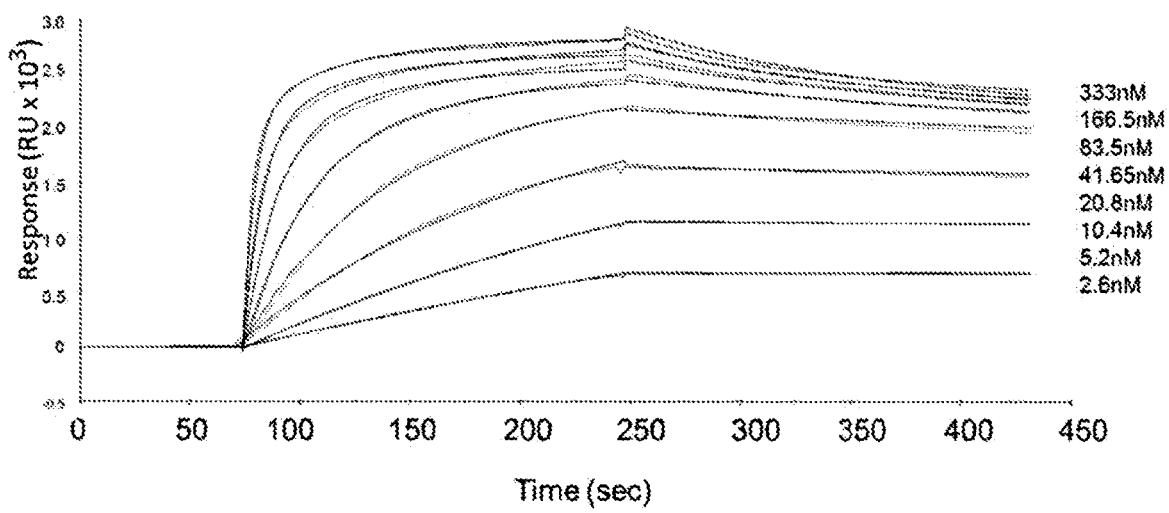
FIG 28 ial Application No. 62/357,536 filed on Jul. 1, 2016. The content of the application is incorporated herein by reference in its entirety.

METHODS AND COMPOSITIONS FOR PDGF-CC INHIBITION

CROSS REFERENCE TO RELATED APPLICATION

This application claims priority to U.S. Provisional Application No. 62/357,536 filed on Jul. 1, 2016. The content of the application is incorporated herein by reference in its entirety.

INCORPORATION BY REFERENCE OF SEQUENCE LISTING PROVIDED AS A TEXT FILE

A Sequence Listing is provided herewith as a text file, "SequenceListing_ST25.txt" created on Jul. 26, 2017, and having a size of 46,457 bytes. The contents of the text file are incorporated by reference herein in their entirety.

FIELD OF THE INVENTION

The present invention relates, in part, to isolated antibodies that specifically interact with and show measurable binding affinity to an epitope of platelet derived growth factor C (PDGF-C) and its dimeric form PDGF-CC. Such antibodies may be used for the modulation of PDGF-CC activity in or secreted from a cell, to study PDGF-CC effects on cell function and, in certain embodiments, for the treatment and/or prevention of a disease or condition associated with PDGF-C expression.

BACKGROUND OF THE INVENTION

Platelet-derived growth factors (PDGFs) are important for normal tissue growth and maintenance, and are also involved in several pathological conditions such as malignancies, atherosclerosis and fibrosis. PDGF signaling is mediated through two structurally related tyrosine kinase receptors, PDGFR-α and PDGFR-β. The PDGF family consists of disulfide-bonded dimers involving four polypeptide chains: the classical PDGF-A and PDGF-B chains and the more recently discovered PDGF-C and PDGF-D chains. The hallmark of each of these chains is that they all contain a VEGF/PDGF homology domain (VHD). The PDGF-C and -D chains are further distinct in that they each also have a CUB domain upstream from the VHD, which forms a two-domain structure.

PDGF-C is secreted from cells as a latent dimer, PDGF-CC, and it is known that regulated proteolytic removal of the CUB domain is required before PDGF-CC can bind to and activate its cognate receptor (PDGFR). Activated PDGF-CC, like PDGF-AA, is thought to signal through PDGFR-α homodimers, though there is some thought that both PDGF-CC, and also PDGF-DD, are able to activate the PDGFRα/β heterodimeric complexes as well.

The participation of PDGF-CC in angiogenesis—a morphological hallmark of many malignant carcinomas—has been demonstrated in numerous models, including mouse embryos, mouse cornea, and ischemic heart tissue. While the specifics of its role are still being studied, PDGF-CC is thought to induce angiogenesis by VEGF up-regulation, activation of PDGF receptors, and/or through a direct effect on the stroma. Autocrine and paracrine PDGF-mediated signaling is, therefore, thought to lead or contribute to accelerated tumor cell growth and invasion thought vascularization of the tumor and its surrounding tissue.

Recent studies have shown that such effects may be countered by inhibiting the activity of PDGF-CC. Specifically, it has been shown that inhibition of PDGF-CC activity leads to a reduction of angiogenesis, which slowed the progression of certain malignancies. In certain instances, it further resulted in a reduction of tumor cell growth (Crawford Y., et al. *Cancer Cell* 15:21-34, 2009). Accordingly, PDGF-CC presents an attractive target for studying PDGF induced angiogenesis. PDGF-CC also presents an attractive target for potential therapeutic and/or potential chemotherapeutic agents for treating malignant carcinomas, particularly those expressing PDGF-C, or otherwise using a PDGF-CC dependent pathway for vascularization and tumor growth.

Recent studies have also shown that PDGF-CC signaling controls the integrity of the blood-brain barrier, the specialized blood vessel wall found in cerebral blood vessels and blood vessels of the spinal cord and the retina of the eye. The unique properties of the blood-brain barrier make it impermeable for most constituents of the blood under normal conditions, including ions and most other small molecules. The reason for this is to seal off the central nervous system (CNS) from toxic and/or infectious agents in the blood, and that normal neuronal activity is not compatible with the properties of the blood. In several types of pathological conditions of the brain and other parts of the CNS, including but not limited to stroke, trauma, inflammatory conditions like multiple sclerosis (MS), infections, primary and secondary cancers, surgery, lack of normal oxygen and nutrient supply to the brain subsequent to cardiac arrest or birth complications, neurodegenerative diseases of the CNS including Alzheimer's disease, the blood-brain barrier integrity becomes compromised resulting in extravasation of fluid and other blood components into the parenchyma of the CNS. This results in swelling and inflammation of the tissue leading to loss of normal perfusion and increased damage to the brain, spinal cord and retina. Accordingly, PDGF-CC presents as an attractive target for potential therapeutic agents for treatment of conditions with a compromised blood-brain barrier as described above. The potential role of PDGF-CC in controlling the integrity of the blood-brain barrier has previously been recognized by Su et al. "Activation of PDGF-CC by plasminogen activator impairs blood brain barrier integrity during ischemic stroke. Nature Medicine, 14; 731-737, 2008, and by Eriksson et al. "Methods and compositions for modulation of blood-neural barrier", International application, PCT/US2007/066804, both which are hereby incorporated as references.

SUMMARY OF THE INVENTION

In certain aspects, the present invention relates to isolated antibodies or fragments thereof that specifically interact with and/or show measurable affinity to an epitope of platelet-derived growth factor C (PDGF-C), including its dimeric form, PDGF-CC. In further aspects, such antibodies or fragments thereof specifically interact with and/or show measurable affinity to a polypeptide within the active portion of the protein PDGF-C (SEQ ID NO: 2) or a polypeptide substantially homologous thereto. In even further aspects, the antibodies or fragments thereof specifically interact with and/or show measurable affinity to an epitope of SEQ ID. NO.: 3 or to a sequence within SEQ ID. NO.: 3 or a polypeptide that is substantially homologous thereto.

Antibodies of the present invention (collectively referred to as anti-PDGF-C antibodies, or as anti-PDGF-CC antibodies) specifically interact with and/or show measurable affinity with both PDGF-C and PDGF-CC, and may include the entire antibody, a fragment or substantially homologous fragment of the monoclonal antibodies (mAbs) 6B3, 11F5, 19C7 and 12F5, of the chimeric antibody ch6B3 or of the humanized antibody hu6B3. Fragments may include one or a portion of the variable light and heavy chain sequences or CDR regions of 6B3, ch6B3, hu6B3, 11F5, 12F5 and 19C7, or may be substantially homologous to such sequences. Light and heavy chain CDRs of each of 6B3, ch6B3, hu6B3, 11F5, 12F5 and 19C7 are as follows:

6B3
Peptide—light chain—SEQ ID NO: 16 (CDR1), SEQ ID NO: 17 (CDR2), and SEQ ID NO: 18 (CDR3); heavy chain—SEQ ID NO: 34 (CDR1), SEQ ID NO: 35 (CDR2), and SEQ ID NO: 36 (CDR3);
Nucleic acid—light chain—SEQ ID NO: 64 (CDR1), SEQ ID NO: 65 (CDR2), and SEQ ID NO: 66 (CDR3); heavy chain—SEQ ID NO: 82 (CDR1), SEQ ID NO: 83 (CDR2), and SEQ ID NO: 84 (CDR3);

ch6B3
Peptide—light chain—SEQ ID NO: 28 (CDR1), SEQ ID NO: 29 (CDR2), and SEQ ID NO: 30 (CDR3); heavy chain—SEQ ID NO: 46 (CDR1), SEQ ID NO: 47 (CDR2), and SEQ ID NO: 48 (CDR3);
Nucleic acid—light chain—SEQ ID NO: 76 (CDR1), SEQ ID NO: 77 (CDR2), and SEQ ID NO: 78 (CDR3); heavy chain—SEQ ID NO: 94 (CDR1), SEQ ID NO: 95 (CDR2), and SEQ ID NO: 96 (CDR3);

11F5
Peptide—light chain—SEQ ID NO: 19 (CDR1), SEQ ID NO: 20 (CDR2), and SEQ ID NO: 21 (CDR3); heavy chain—SEQ ID NO: 37 (CDR1), SEQ ID NO: 38 (CDR2), and SEQ ID NO: 39 (CDR3);
Nucleic acid—light chain—SEQ ID NO: 67 (CDR1), SEQ ID NO: 68 (CDR2), and SEQ ID NO: 99 (CDR3); heavy chain—SEQ ID NO: 85 (CDR1), SEQ ID NO: 86 (CDR2), and SEQ ID NO: 87 (CDR3);

12F5
Peptide—light chain—SEQ ID NO: 22 (CDR1), SEQ ID NO: 23 (CDR2), and SEQ ID NO: 24 (CDR3); heavy chain—SEQ ID NO: 40 (CDR1), SEQ ID NO: 41 (CDR2), and SEQ ID NO: 42 (CDR3);
Nucleic acid—light chain—SEQ ID NO: 70 (CDR1), SEQ ID NO: 71 (CDR2), and SEQ ID NO: 72 (CDR3); heavy chain—SEQ ID NO: 88 (CDR1), SEQ ID NO: 89 (CDR2), and SEQ ID NO: 90 (CDR3).

19C7
Peptide—light chain—SEQ ID NO: 25 (CDR1), SEQ ID NO: 26 (CDR2), and SEQ ID NO: 27 (CDR3); heavy chain—SEQ ID NO: 43 (CDR1), SEQ ID NO: 44 (CDR2), and SEQ ID NO: 45 (CDR3);
Nucleic acid—light chain—SEQ ID NO: 73 (CDR1), SEQ ID NO: 74 (CDR2), and SEQ ID NO: 75 (CDR3); heavy chain—SEQ ID NO: 91 (CDR1), SEQ ID NO: 92 (CDR2), and SEQ ID NO: 93 (CDR3).

hu6B3
Peptide—light chain—SEQ ID NO: 31 (CDR1), SEQ ID NO: 32 (CDR2), and SEQ ID NO: 33 (CDR3); heavy chain—SEQ ID NO: 49 (CDR1), SEQ ID NO: 50 (CDR2), and SEQ ID NO: 51 (CDR3);
Nucleic acid—light chain—SEQ ID NO: 79 (CDR1), SEQ ID NO: 80 (CDR2), and SEQ ID NO: 81 (CDR3); heavy chain—SEQ ID NO: 97 (CDR1), SEQ ID NO: 98 (CDR2), and SEQ ID NO: 99 (CDR3);

To this end, and in certain aspects, the antibodies or portion of the anti-PDGF-C antibodies of the present invention are encoded in an isolated nucleic acid molecule, which includes one or more of the foregoing sequences, fragments, or homologues thereof. The nucleic acid molecule may encode the variable heavy chain and/or light chain and/or CDRs, including fragments thereof, of monoclonal antibodies 6B3, 11F5, 19C7, and 12F5, of chimeric antibody ch6B3 or of humanized antibody hu6B3. Such nucleic acid sequences may be cloned into an expression vector and inserted into a recombinant host cell. To this end, the present invention includes each of the isolated nucleic acids, the recombinant expression vectors encoding such isolated nucleic acids and host cell expressing such vectors.

Anti-PDGF-C antibodies of the present invention that incorporate one or more of the foregoing sequences, including substantially homologous variants thereof, may be provided as monoclonal antibodies, chimeric antibodies, humanized antibodies, human monoclonal antibodies, or other variants defined herein.

The present invention also relates to treatment methods using one or a combination of the anti-PDGF-C antibodies of the present invention alone or in a pharmaceutical composition. One embodiment of a treatment method includes modulating activity of platelet-derived growth factor CC (PDGF-CC) in a cell, such as a PDGF-CC expressing carcinoma, by administering to the mammal an effective amount of at least one anti-PDGF-C antibody of the present invention. In further embodiments, the treatment methods of the present invention include modulation of PDGF-CC mediated autocrine or paracrine signaling from a cell. With certain PDGF-CC expressing carcinomas, for example, PDGF-CC autocrine or paracrine signaling is associated vascularization, stromal support, or other tumor effects in or around the cells, which lead to cell viability and/or tumor growth. Administration of one or more anti-PDGF-C antibodies of the present invention may be used to inhibit or prevent such signaling resulting in a decrease of such effects. To this end, treatment methods of present invention also include methods of reducing angiogenesis, stromal support, cell viability, tumor size, or the like, by administering to the mammal an effective amount of at least one anti-PDGF-C antibody of the present invention.

In yet another embodiment, a treatment method includes modulating activity of platelet-derived growth factor CC (PDGF-CC) in the blood-brain barrier by administering to the mammal an effective amount of at least one anti-PDGF-C antibody of the present invention. In further embodiments, the treatment methods of the present invention include modulation of PDGF-CC mediated opening of the blood-brain barrier in several pathological conditions of the CNS. Administration of one or more anti-PDGF-C antibodies of the present invention may be used to inhibit or prevent such signaling resulting in a decrease of such effects. To this end, treatment methods of present invention also include methods of reducing opening of the blood-brain barrier by CNS pathologies, or the like, by administering to the mammal an effective amount of at least one anti-PDGF-C antibody of the present invention.

Additionally, the present invention includes diagnostic assays, drug screen assays, and the like for diagnosing in a bodily fluid of a patient or subject the presence of a PDGF-CC expressing cell or otherwise identifying alternative therapeutics that exhibit targeted inhibition of PDGF-CC activity. Anti-PDGF-C antibodies of the present invention may also be used as a molecular tool to study the activity of PDGF-CC in a PDGF-CC expressing cell.

In conjunction with such embodiments, the present invention also includes a kit for detecting platelet-derived growth factor C (PDGF-C) peptide while showing minimal affinity to a platelet-derived growth factor other than PDGF-C that includes (1) an antibody or a fragment thereof, capable of specifically binding in vitro to an epitope of a platelet-derived growth factor C (PDGF-C) peptide while showing minimal affinity to a platelet derived growth factor other than PDGF-C; and, (2) a reagent that binds, directly, or indirectly, to said antibody or the fragment thereof.

The present invention also provides a method for modulating permeability of blood-brain barrier in a higher vertebrate animal in need thereof. The method comprises administering to the animal an effective amount of an antibody described above or an antigen-binding portion thereof. Also provided is a method for treating a cerebrovascular disease or condition. This method comprises administering to a subject in need thereof an effective amount of an antibody described above or an antigen-binding portion thereof. Examples of the disease or condition include edema ascites, hydrothorax, hydropericardium, cerebral/brain edema, hydrocephalus, glaucoma, acute pulmonary edema, a retinopathy, a maculopathy, stroke, ischemic retinopathies, Alzheimer's disease, multiple sclerosis, trauma, inflammation, and tumors of the CNS. In one example, the retinopathy is diabetic retinopathy. In another, the maculopathy is wet age-related macular degeneration (AMD).

In another aspect, this invention provides a non-human transgenic animal, the genome of which comprises a heterologous platelet derived growth factor C (PDGF-C) gene encoding a heterologous PDGF-C protein. The heterologous PDGF-C protein can be at least 75% (e.g., 80%, 85%, 90%, 95%, 96%, 97%, 98%, 99%, and 100%) identical to a human PDGF-C protein (SEQ ID NO: 1). The transgenic animal can be a mouse, a rat, or a rabbit. In one example, the animal is a mouse. In that case, the heterologous PDGF-C protein can be a humanized mouse PDGF-C protein. The humanized mouse PDGF-C protein can be protein can be at least 75% (e.g., 80%, 85%, 90%, 95%, 96%, 97%, 98%, 99%, and 100%) identical to a mouse PDGF-C protein (SEQ ID NO: 104). It can comprise one or more of the following mutations to a mouse PDGF-C protein: K242T, K246R, R299S, K318R, N342S, and A343T. For example, the humanized mouse PDGF-C protein can comprise the sequence of SEQ ID NO: 103.

One of skill in the art will readily appreciate that the foregoing is not necessarily limiting to the invention and that additional embodiments and advantages of the present invention are readily available based on the disclosure provided herein.

To aid in the understanding of the invention, the following non-limiting definitions are provided:

The term "homology" as used herein may refer to the existence of shared structure between two compositions. The term "homology" in the context of proteins may refer to the amount (e.g. expressed in a percentage) of overlap between two or more amino acid and/or peptide sequences. In the context of nucleic acids, the term may refer to the amount (e.g. expressed in a percentage) of overlap between two or more nucleic acid sequences. As used herein, the percent (%) homology between two sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm. Such homology is well-represented in the art via local alignment tools and/or algorithms, and may include pairwise alignment, multiple sequence alignment methods, structural alignment methods, and/or phylogenetic analysis methods.

For example, the percent identity of two amino acid sequences or of two nucleic acids can be determined using the algorithm of Karlin and Altschul *Proc. Natl. Acad. Sci. USA* 87:2264-68, 1990, modified as in Karlin and Altschul *Proc. Natl. Acad. Sci. USA* 90:5873-77, 1993. Such an algorithm is incorporated into the NBLAST and XBLAST programs (version 2.0) of Altschul, et al. *J. Mol. Biol.* 215:403-10, 1990. BLAST nucleotide searches can be performed with the NBLAST program, score=100, wordlength-12 to obtain nucleotide sequences homologous to the nucleic acid molecules of the invention. BLAST protein searches can be performed with the) (BLAST program, score=50, wordlength=3 to obtain amino acid sequences homologous to the protein molecules of the invention. Where gaps exist between two sequences, Gapped BLAST can be utilized as described in Altschul et al., *Nucleic Acids Res.* 25(17):3389-3402, 1997. When utilizing BLAST and Gapped BLAST programs, the default parameters of the respective programs (e.g., XBLAST and NBLAST) can be used.

As used herein "substantially homologous" means a sequence that is largely, but not entirely, homologous, and which retains most or all of the activity as the sequence to which it is homologous. Specifically, "substantially homologous" means that a sequence is at least 70% identical, and preferably at least 75%, 80%, 90%, 95%, 96%, 97%, 98%, 99% homology to the reference sequence.

As used herein, a heterologous polypeptide, nucleic acid, or gene is one that originates from a foreign species, or, if from the same species, is substantially modified from its original form. Two fused domains or sequences are heterologous to each other if they are not adjacent to each other in a naturally occurring protein or nucleic acid.

A transgene is to a nucleic acid sequence (encoding, e.g., one or more subject polypeptides), which is partly or entirely heterologous to a subject or a cell into which it is introduced, or, is homologous to an endogenous gene of the subject or cell into which it is introduced but is intended to be inserted into the subject's genome in such a way as to alter the genome (e.g., it is inserted at a location which differs from that of the natural gene or its insertion results in a knockout). A transgene can include one or more operably linked transcriptional regulatory sequences (e.g., an enhancer sequence) and any other nucleic acid, such as an intron, that may be necessary for optimal expression of a nucleic acid of interest. A transgenic cell is a cell containing a transgene. A transgenic animal is any animal in which one or more, or all, of the cells of the animal include a transgene. The transgene can be introduced into the cell by introduction into a precursor cell by way of deliberate genetic manipulation known in the art. The transgene may be integrated within a chromosome, or it may be an extra-chromosomally replicating DNA.

As used herein, the term "epitope" refers to a site on an antigen to which B and/or T cells respond or a site on a molecule against which an antibody will be produced and/or to which an antibody will bind. For example, an epitope can be recognized by an antibody defining the epitope. An epitope can be either a "linear epitope" (where a primary amino acid primary sequence comprises the epitope; typically at least 3 contiguous amino acid residues, and more usually, at least 5, and up to about 8 to about 10 amino acids in a unique sequence) or a "conformational epitope" (an epitope wherein the primary, contiguous amino acid sequence is not the sole defining component of the epitope). A conformational epitope may comprise an increased number of amino acids relative to a linear epitope, as this conformational epitope recognizes a three-dimensional structure of the peptide or protein. For example, when a protein molecule folds to form a three dimensional structure, certain amino acids and/or the polypeptide backbone forming the conformational epitope become juxtaposed enabling the antibody to recognize the epitope. Methods of determining conformation of epitopes include but are not limited to, for example, x-ray crystallography, two-dimensional nuclear magnetic resonance spectroscopy and site-directed spin labeling and electron paramagnetic resonance spectroscopy. See, for example, Epitope Mapping Protocols in Methods in Molecular Biology, Vol. 66, Glenn E. Morris, Ed. (1996), the disclosure of which is incorporated in its entirety herein by reference.

As used herein, the term "isolated" is as it is used within the art, namely the state in which antibodies/specific binding members, nucleic acid molecules and the such are found. Antibodies/specific binding members and nucleic acid molecules will be free or substantially free of material with which they are naturally associated such as other polypeptides or nucleic acids with which they are found in their natural environment, or the environment in which they are prepared (e.g. cell culture) when such preparation is by recombinant DNA technology (practiced in vitro) or in vivo. "Isolated" covers any form containing the identified and characterized component(s) of the present invention following removal from that initial environment. Examples, but certainly not limitations, include pharmaceutical formulations, formulation with diluents, antibodies/specific binding members, nucleic acid molecules and portions thereof which have been modified (e.g., antibody glycosylation) either in vitro or in vivo and removed from that environment.

The terms "subject" or "patient" is meant to include any member of the Phylum Chordata, including, without limitation, humans and other primates, including nonhuman primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like.

The term "treating" or "treatment" of a disease refers to executing a protocol, which may include administering one or more drugs to a subject (human or otherwise), in an effort to alleviate signs or symptoms of the disease. Alleviation can occur prior to signs or symptoms of the disease appearing, as well as after their appearance. Thus, "treating" or "treatment" includes "preventing" or "prevention" of disease. In addition, "treating" or "treatment" does not require complete alleviation of signs or symptoms, does not require a cure, and specifically includes protocols which have only a marginal positive effect on the subject.

As used herein, the terms "effective amount" or "pharmaceutically effective amount" of antibody, as provided herein, refers to a nontoxic but sufficient amount of the active ingredient in order to provide the desired biological result. An appropriate "effective" amount in any individual case may be determined by one of ordinary skill in the art using routine experimentation.

As used herein, the terms "pharmaceutically acceptable" or "pharmacologically acceptable" mean a material may be administered to an individual in a drug delivery device along with the formulated biological agent without causing any undesirable biological effects or interacting in a deleterious manner with any of the components of the composition in which it is contained (e.g., a "pharmaceutically acceptable composition").

As used herein, the phrases "physiologically acceptable carrier" and "pharmaceutically acceptable carrier" which may be interchangeably used refer to a carrier, diluent, and excipient that does not cause significant irritation to an organism and does not abrogate the biological activity and properties of the administered compound. An adjuvant is included under these phrases.

As used herein, the term "excipient" refers to an inert substance added to a pharmaceutical composition to further facilitate administration of an active ingredient.

BRIEF DESCRIPTION OF THE DRAWINGS

FIG. 2 illustrates the binding specificity of the four mAbs identified, 6B3, 11F5, 12F5, and 19C7, wherein

FIG. 3 provides an alignment of the complete variable light chain amino acid sequences (SEQ ID NOs: 4-7) of the antibodies 6B3, 11F5, 12F5, and 19C7, with CDRs underlined.

FIG. 4 provides an alignment of the complete variable heavy chain amino acid sequences (SEQ ID NOs: 10-13) 6B3, 11F5, 12F5, and 19C7, with CDRs underlined.

FIG. 5 provides an alignment of the complete variable heavy and light chain amino acid sequences of ch6B3 (SEQ ID NOS: 14 and 8, respectively), as compared to the murine antibody (mu6B3) (SEQ ID NOS: 10 and 4, respectively).

FIG. 8 illustrates residues 231 to 345 of the PDGF-C amino acid sequence (SEQ ID NO: with the 6B3 epitope sequence highlighted and homologies to PDGF-D indicated.

FIGS. 18A and 18B show results demonstrating modulation of PDGF-CC mediated opening of the blood-brain barrier by anti-PDGF-C antibody. FIG. 18A is a set of photographs illustrating the extravasion of Evans Blue in mouse brains following an intrathecal injection of PDGF-CC and an intraperitonal injections of anti-PDGF-C antibody 6B3, or control antibody BM4. FIG. 18B is a diagram showing the same results.

FIG. 19 provides a comparison of the amino acid sequences for the growth factor domains of mouse and human PDGF-CC (SEQ ID NO: 108 and 109). The red arrows indicate those amino acids that were changed to generate the partly humanized PDGF-CC mouse strain.

FIG. 20 illustrates the amino acid sequence of the partially humanized mouse PDGF-C protein (residues 1-345, SEQ ID NO: 103). The six amino acid replacements in the growth factor domain (amino acid residues 229-345) are underlined. The amino acid replacements are $^{242}$K to $^{242}$T, $^{246}$K to $^{246}$R, $^{299}$R to $^{299}$S, $^{318}$K to $^{318}$R, $^{342}$N to $^{342}$ s, and $^{343}$A to $^{343}$T.

FIG. 25 provides an alignment of the complete variable light chain protein sequences of hu6B3 (SEQ ID NO: 9), as compared to the murine antibody (mu6B3) (SEQ ID NO: 4), with CDRs underlined.

FIG. 26A provides an alignment of the complete variable heavy chain protein sequences (SEQ ID NO: 14) of hu6B3HCR, as compared to the murine antibody (mu6B3, SEQ ID NO: 15), with CDRs underlined. The hu6B3"R" version demonstrated superior binding characteristics for PDGF-CC and was selected as the final sequence of the humanized antibody. FIG. 26B provides an alignment of the complete variable heavy chain protein sequences of and hu6B3HCG (SEQ ID NO: 110), as compared to the murine antibody (mu6B3, SEQ ID NO: 15), with CDRs underlined.

FIG. 27 illustrates by ELISA analysis (FIG. 27A) and Western blotting (FIG. 27B) that the specificity and function of murine 6B3 anti-PDGF-CC antibody is retained following chimerization and humanization.

FIG. 28 illustrates sensorgrams from the biosensor analysis of the interaction between immobilized PDGF-CC and increasing concentrations of hu6B3 antibody variants A) heavy chain G30R and B) heavy chain R30.

DETAILED DESCRIPTION OF THE INVENTION

Figure 1:
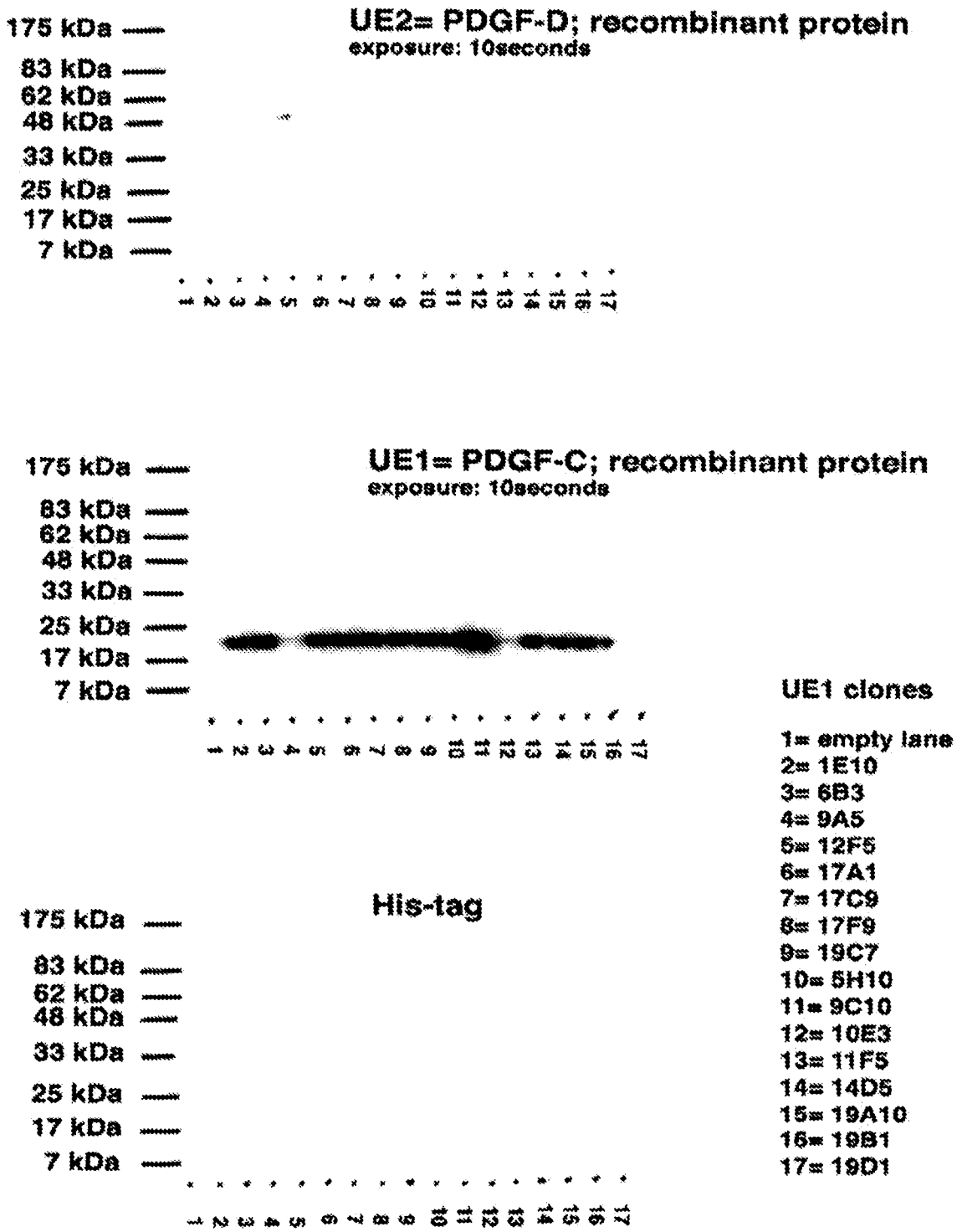
FIG. 1 illustrates Hybridoma Supernatant of PDGF-CC monoclonal antibodies binding activity for recombinant human PDGF-DD protein (top panel), PDGF-CC protein (middle panel), and histidine polypeptide (bottom panel).

PDGF-C is demonstrated herein to be a molecular hallmark for many existing carcinomas and has been linked to the induction pathway for angiogenesis and tumor growth, and as a factor controlling the physiological properties of the blood-brain barrier of the CNS. PDGF-C expression is also linked to other disease states such as atherosclerosis and fibrosis. Accordingly, it presents a viable target for the study of PDGF-C expressing cells, or alternatively, for a method of treating a patient diagnosed with a disease or condition where the associated cell types exhibit PDGF-C expression/secretion. In certain aspects, the present invention relates to isolated antibodies that specifically interact with and show measurable affinity to one or more epitopes of platelet-derived growth factor C (PDGF-C), herein "anti-PDGF-C antibodies." Such antibodies may be used for the modulation of PDGF-CC activity in or secreted from a cell to study its effects on cell function and, in certain embodiments, for the treatment of the disease or condition associated with increased PDGF-C expression or increased PDGF-CC activity. In certain embodiments, the anti-PDGF-C antibodies may be administered to a subject to treat or prevent tumor cell growth and metastasis and/or for the prevention of angiogenesis and tumor growth, as well as administrated to a subject to treat a CNS injury or CNS disease.

In certain aspects, it refers to the human form of the protein, which has the following amino acid sequence:

SEQ ID NO: 1
MSLFGLLLVTSALAGQRRGTQAESNLSSKFQFSSNKEQNGVQDPQHERII

TVSTNGSIHSPRFPHTYPRNTVLVWRLVAVEENVWIQLTFDERFGLEDPE

DDICKYDFVEVEEPSDGTILGRWCGSGTVPGKQISKGNQIRIRFVSDEYF

PSEPGFCIHYNIVMPQFTEAVSPSVLPPSALPLDLLNNAITAFSTLEDLI

RYLEPERWQLDLEDLYRPTWQLLGKAFVFG<u>RKSRVVDLNLLTEEVRLYSC</u>

<u>TPRNFSVSIREELKRTDTIFWPGCLLVKRCGGNCACCLHNCNECQCVPSK</u>

<u>VTKKYHEVLQLRPKTGVRGLHKSLTDVALEHHEECDCVCRGSTGG</u>.

The present invention, however, is not limited to this form and may include any variant, natural or synthetic, that exhibits the properties of PDGF-C and PDGF-CC in a targeted cell that are discussed herein or otherwise known in the art.

The targeted epitope(s) of the anti-PDGF-C antibodies include any one or more peptide sequences of PDGF-C against which one or more antibodies of the present invention will bind with measurable affinity. Such sequences may include active or non-active regions of the protein and include either linear epitopes and/or conformation epitopes, as defined herein. In certain aspects, they include one or more regions where the binding of the antibodies results in a measurable reduction of PDGF-CC activity in the host cell. To this end, in certain aspects, the epitope is at a position of the protein where the binding of the antibody modifies protein activity such as active site blocking, steric hindrance, allosteric inhibition, or the like. Such a binding site may include, but is not limited to, one or more epitopes within the PDGF-CC core active domain, which is provided at residues 231-345 (underlined above) of the full-length sequence, which is provided as SEQ ID NO.: 2. In another embodiment, the epitope includes the amino acid sequence (or an amino acid sequence within) SVSIREELKRTDTIFWPGC (SEQ ID NO: 3). The epitopes of the present invention are not limited to the exact sequences within SEQ ID NOS.: 1-3 and may include any sequence having at least 70% homology, 80% homology, 90% homology or 99% homology.

The anti-PDGF-C antibodies of the present invention include two identical heavy chains and two light chains containing one or more of the antigen binding domains identified herein. The light chain includes one variable domain ($V_L$) and one constant domain ($C_L$). The heavy chain also includes one variable domain ($V_H$) and, depending on the class or isotype of antibody, three or four constant domains ($C_{H1}$, $C_{H2}$, $C_{H3}$ and $C_{H4}$). Isotypes include, but are not limited to, IgA, IgD, IgE, IgG, and IgM, with IgA and IgG further subdivided into subclasses or subtypes. In certain non-limiting inventions, the isotype of the present invention is IgG, which includes one or a combination of its sub-types (e.g. IgG1, IgG2, IgG3, and IgG4).

Dependent on the application, certain isotypes or isotype derivatives may be preferentially used for the antibodies contemplated by this invention.

In some embodiments of the invention, the antibody has an isotype that leads to significant complement-dependent cytotoxicity (CDC) and/or effector mediated killing by antibody-dependent cellular cytotoxicity (ADCC). Such effector functions include, but are not limited to, activation of the first component of the complement (C1), Fc gamma receptor I (FcγRI, also known as CD64)), FcγRII (also known as CD32) or FcγRIIIa/b (also known as CD16). For IgG isoforms, the levels of effector function decrease in the order of IgG3≥IgG1≥IgG2≥IgG4. Therefore, isotypes like IgG3 and IgG1 with significant effector function and/or ability to activate the complement are particularly useful for oncology applications of the contemplated antibodies, such as the treatment or prevention of tumor cell growth, viability, or metastasis, and the prevention of angiogenesis.

In another embodiment of the invention, the antibody has an isotype that is considered relatively inactive, e.g. that exhibits reduced or no effector functions. Non-limiting examples for such isotypes include IgG2, IgG4, or other isotypes that have been mutated to decrease their effector functions. For example, substitution of human IgG1 and IgG2 residues 233-236 and IgG4 residues at positions 327, 330 and 331 have been demonstrated to significantly decrease CDC and ADCC (see Armour K L, Clark M R, Hadley A G, Williamson L M. Recombinant human IgG molecules lacking Fcgamma receptor I binding and monocyte triggering activities. Eur J Immunol. 1999 August; 29(8):2613-24 and Shields R L, Namenuk A K, Hong K, Meng Y G, Rae J, Briggs J, Xie D, Lai J, Stadlen A, Li B, Fox J A, Presta L G. High resolution mapping of the binding site on human IgG1 for Fc gamma RI, Fc gamma RII, Fc gamma RIII, and FcRn and design of IgG1 variants with improved binding to the Fc gamma R. J Biol Chem. 2001 Mar. 2; 276(9):6591-604). Isotypes with reduced effector functions are particularly useful for antibodies that are administered for treating disorders or conditions associated with a compromised a BBB of the CNS.

The paired heavy chain constant domains are generally understood to define the Fc region of the antibody. Based on its sequence, it provides the antibody with one or more of the isotypes discussed above. The Fc region is associated with Fc receptor binding, activation of complement-mediated cytotoxicity and antibody-dependent cellular-cytotoxicity. To this end, it is at least partially responsible for eliciting immunological reactivity.

The $V_L$ and $V_H$ domains of the antibody are generally defined as the "Fv" region and constitute the antigen-binding site. A single chain Fv (scFv) includes a protein containing a $V_L$ domain and a $V_H$ domain on one polypeptide chain, wherein the N terminus of one domain and the C terminus of the other domain are joined by a flexible linker. A "Fab" region refers to the portion of the antibody including the $V_L$-$C_L$ (i.e., a light chain) and $V_H$-$C_H$ (also designated "Fd").

Present within each $V_L$ and $V_H$ domain of the Fv region of the antibody are eight framework regions (FR) and six total complementarity-determining regions (CDRs). Four FRs and three CDRs are found in each $V_L$ chain and the $V_H$ chain. The four FR regions (FR1, FR2, FR3, and FR4) are relatively conserved, while the CDR regions (CDR1, CDR2, and CDR3) represent the hypervariable portion of the antibody primarily responsible for the recognition and binding of the targeted epitope sequence. Typically, the FR and CDRs regions are arranged from $NH_2$ terminus to the COOH terminus of the antibody as follows: FR1, CDR1, FR2, CDR2, FR3, CDR3, FR4.

In certain aspects, the anti-PDGF-C antibodies of the present invention include isolated monoclonal antibodies 6B3, 11F5, 12F5, and 19C7, as defined herein, and the hybridomas that produce such antibodies. Antibodies of the present invention also include variants of the monoclonal antibodies 6B3, 11F5, 12F5, and 19C7, i.e. antibodies having one or a combination of peptide sequences from the antibodies 6B3, 11F5, 12F5, and 19C7. Two non-limiting examples of such a variant are the chimeric antibody ch6B3 and the humanized antibody hu6B3 having substantially homologous CDRs sequences to the 6B3 mAb.

The following Tables 1 and 2 provide the amino acid sequences of the variable light chains and variable heavy chains, respectively, of antibodies 6B3, 11F5, 12F5, 19C7, ch6B3 and hu6B3:

TABLE 1

Variable Light Chain Sequences

| | |
|---|---|
| 6B3 (IgG2aκ) | DIVMTQSPSSLAMSVGQKVTMSCKSSQSLLNSRNQKNYL AWYQQKPGQSPKLLVYFASTRESGVPDRFTGSGSGTDFT LTISSVQAEDLAVYYCQQHYSTPLTFGAGTKLELKR SEQ ID NO.: 4 |
| 11F5 (IgG2aκ) | DIVMTQSPSSLAMSVGQKVAVSCKSSQSLLNSSNQKNYL AWYQQKPGQSPKLLVYFASTRDSGVPDRFTGSGSGTDFT LTISSVQAEDLAVYYCQQHYSTPLTFGAGTKLELKR SEQ ID NO.: 5 |
| 12F5 (IgG2aκ) | DVVMTQTPLSLPVSLGDQASISCRSSQSIVHSNGNTYLH WYLQKPGQSPKLLIYRVSNRFSGVPDRFSGSGSGTDFTL KISRVEAEDMGVYYCFQGTHVPFTFGSGTKLEIKR SEQ ID NO.: 6 |
| 19C7 (IgG2aκ) | DIVMTQSPSSLAMSVGQKVTMSCKSSQSLLNSRNQKNYL AWYQQKPGQSPKLLVYFASTRESGVPDRFTGSGSGTDFT LTISSVQAEDLAVYYCQQHYSTPLTFGAGTKLELKR SEQ ID NO.: 7 |
| ch6B3 (IgG1κ) | DIVMTQSPSSLAMSVGQKVTMSCKSSQSLLNSRNQKNYL AWYQQKPGQSPKLLVYFASTRESGVPDRFTGSGSGTDFT LTISSVQAEDLAVYYCQQHYSTPLTFGAGTKLELKR SEQ ID NO.: 8 |
| hu6B3 (IgG1κ) | DIVMTQSPSSLAMSVGERATINCKSSQSLLNSRNQKNYL AWYQQKPGQPPKLLIYFASTRESGVPDRFSGSGSGTDFT LTISSVQAEDVAVYYCQQHYSTPLTFGGGTKVELKR SEQ ID NO.: 9 |

TABLE 2

Variable Heavy Chain Sequences

| | |
|---|---|
| 6B3 (IgG2aκ) | QVQLQQSGVEVARPGASVKLSCKASGYTFRSYGITWVRQ RTGQGLEWIGEIYPRSGKTYYNEKFKGKATLTADTSSST VYMELRSLTSEDSAVYFCAREGYGYDGGYFDYWGQGTTL TVSS SEQ ID NO.: 10 |
| 11F5 (IgG2aκ) | QVQLQQSGAELARPGASVKLSCKASGYIFISYGISWVKQ RTGQGLEWIGEIYPRSGKTYYNEKFKDKAALTADKSSSI AYMELRSLTSEDSAVYFCAREGYGYDGGYFDYWGQGTIL TVSS SEQ ID NO.: 11 |
| 12F5 (IgG2aκ) | EVKLEESGGGLVQPGGSRELSCEGSGFTFSGFWMSWVRQ TPGKTLEWIGDINSDGSAIIYAPSIKDRFTIFRDNDKST LYLQMNNVRSEDTATYFCMRWGY-YGSNYFDYWGQGTTL TVSS SEQ ID NO.: 12 |
| 19C7 (IgG2aκ) | QVQLQQSGVEVARPGASVKLSCKASGYTFRSYGITWVRQ RTGQGLEWIGEIYPRSGKTYYNEKFKGKATLTADTSSST VYMELRSLTSEDSAVYFCAREGYGYDGGYFDYWGQGTTL TVSS SEQ ID NO. : 13 |
| ch6B3 (IgG1κ) | QVQLQQSGVEVARPGASVKLSCKASGYTFGSYGITWVRQ RTGQGLEWIGEIYPRSGKTYYNEKFKGKATLTADTSSST VYMELRSLTSEDSAVYFCAREGYGYDGGYFDYWGQGTTL TVSS SEQ ID NO.: 14 |
| hu6B3 (IgG1κ) | QVQLVQSGAEVKKPGASVKVSCKASGYTFRSYGITWVRQ ATGQGLEWMGEIYPRSGKTGYAQKFQGRVTMTADTSTST VYMELRSLRSEDSAVYFCAREGYGYDGGYFDYWGQGTLV TVSS SEQ ID NO.: 15 |

The following Tables 3 and 4 provide the amino acid sequences of the variable light chain CDRs and the variable heavy chain CDRs, respectively, of antibodies 6B3, 11F5, 12F5, 19C7, ch6B3 and hu6B3:

TABLE 3

Variable Light Chain CDR Sequences

| | CDR1 | CDR2 | CDR3 |
|---|---|---|---|
| 6B3 (IgG2aκ) | KSSQSLLNSRNQKNYLA (SEQ ID NO: 16) | FASTRES (SEQ ID NO: 17) | QQHYSTPLT (SEQ ID NO: 18) |
| 11F5 (IgG2aκ) | KSSQSLLNSSNQKNYLA (SEQ ID NO: 19) | FASTRDS (SEQ ID NO: 20) | QQHYSTPLT SEQ ID NO: 21) |
| 12F5 (IgG2aκ) | RSSQSIVHSNGNTYLH (SEQ ID NO: 22) | RVSNRFS (SEQ ID NO: 23) | FQGTHVPFT (SEQ ID NO: 24) |
| 19C7 (IgG2aκ) | KSSQSLLNSRNQKNYLA (SEQ ID NO: 25) | FASTRES (SEQ ID NO: 26) | QQHYSTPLT (SEQ ID NO: 27) |
| ch6B3 (IgG1κ) | KSSQSLLNSRNQKNYLA (SEQ ID NO: 28) | FASTRES (SEQ ID NO: 29) | QQHYSTPLT (SEQ ID NO: 30) |
| hu6B3 (IgG1κ) | KSSQSLLNSRNQKNYLA (SEQ ID NO: 31) | FASTRES (SEQ ID NO: 32) | QQHYSTPLT (SEQ ID NO: 33) |

TABLE 4

Variable Heavy Chain CDR Sequences

| | CDR1 | CDR2 | CDR3 |
|---|---|---|---|
| 6B3 (IgG2aκ) | GYTFRSYGIT (SEQ ID NO: 34) | EIYPRSGKTYYNEKFKG (SEQ ID NO: 35) | EGYGYDGGYFDY (SEQ ID NO: 36) |
| 11F5 (IgG2aκ) | GYIFISYGIS (SEQ ID NO: 37) | EIYPRSGKTYYNEKFKD (SEQ ID NO: 38) | EGYGYDGGYFDY (SEQ ID NO: 39) |

TABLE 4-continued

Variable Heavy Chain CDR Sequences

| | CDR1 | CDR2 | CDR3 |
|---|---|---|---|
| 12F5 (IgG2aκ) | GFTFSGFWMS (SEQ ID NO: 40) | DINSDGSAIIYAPSIKD (SEQ ID NO: 41) | WGYYGSNYFDY (SEQ ID NO: 42) |
| 19C7 (IgG2aκ) | GYTFRSYGIT (SEQ ID NO: 43) | EIYPRSGKTYYNEKFKG (SEQ ID NO: 44) | EGYGYDGGYFDY (SEQ ID NO: 45) |
| ch6B3 (IgG1κ) | GYTFGSYGIT (SEQ ID NO: 46) | EIYPRSGKTYYNEKFKG (SEQ ID NO: 47) | EGYGYDGGYFDY (SEQ ID NO: 48) |
| hu6B3 (IgG1κ) | GYTFRSYGIT (SEQ ID NO: 49) | EIYPRSGKTGYAQKFQG (SEQ ID NO: 50) | EGYGYDGGYFDY (SEQ ID NO: 51) |

The anti-PDGF-C antibodies of the present invention, may include the foregoing variable light chain, variable heavy chain, and/or CDR peptide sequences exactly or may be sufficiently homologous or substantially the same as one of the foregoing sequences, so as to exhibit measurable binding affinity to the PDGF-C protein, including to one or more of the epitopes identified herein. Substantially the same amino acid sequence or sufficiently homologous is defined herein as a sequence with at least 70%, at least about 80%, at least about 90%, at least about 95% or at least about 99% homology or identity to a compared amino acid sequence, as determined by the FASTA search method in accordance with Pearson and Lipman, Proc. Natl. Acad. Sci. USA 85:2444-2448 (1988), the contents of which are incorporated herein by reference. Anti-PDGF-C antibodies of the present invention may be provided as naturally occurring antibodies, bivalent fragments such as (Fab')$_2$, monovalent fragments such as Fab, single chain antibodies, single chain Fv (scFv), single domain antibodies, multivalent single chain antibodies, diabodies, triabodies, and the like that bind with measurable affinity to the targeted antigen or epitopes.

Also included within the present invention are the isolated nucleic acid molecules encoding the amino acid sequences (or fragments thereof) above, which may include the $V_H$ and/or $V_L$ regions and/or CDRs of 6B3, 11F5, 12F5, 19C7 or the ch6B3 or hu6B3 antibodies. The Variable Light and Heavy Chain DNA sequences for 6B3, 11F5, 12F5, 19C7, ch6B3 and hu6B3 are as follows in Tables 5 and 6, with CDR regions of each being underlined.

TABLE 5

Variable Light Chain DNA Sequences

| | |
|---|---|
| 6B3 (IgG2aκ) - V$_L$ Chain Seq. | GATATTGTGATGACCCAGTCTCCATCCTCCCTGGCTATGTCAGTAGGACAGAAGGTCACTATGAGTT GC<u>AAGTCCAGTCAGAGCCTTTTAAATAGTAGAAATCAAAAGAACTATTTGGC</u>CTGGTACCAGCAGAA ACCAGGACAGTCTCCTAAACTTCTGGTATA<u>CTTTGCATCCACTAGGGAATCT</u>GGGGTCCCTGATCGC TTCACAGGCAGTGGATCTGGGACAGATTTCACTCTTACCATCAGCAGTGTGCAGGCTGAGGACCTGG CAGTTTATTACTGT<u>CAGCAACATTATAGCACTCCTCTCACG</u>TTCGGTGCTGGGACCAAGCTGGAGCT GAAACGG SEQ ID NO.: 52 |
| 11F5 (IgG2aκ) - V$_L$ Chain Seq. | GATATTGTGATGACCCAGTCTCCATCCTCCCTGGCTATGTCAGTAGGACAGAAGGTCGCTGTGAGCT GC<u>AAGTCCAGTCAGAGCCTTTTAAATAGTAGCAATCAAAAGAACTATTTGGC</u>CTGGTACCAGCAGAA ACCAGGACAGTCTCCTAAACTTCTTGTATA<u>CTTTGCATCCACTAGGGACTCT</u>GGGGTCCCTGATCGC TTCACAGGCAGTGGATCTGGGACAGATTTCACTCTTACCATCAGCAGTGTGCAGGCTGAAGACCTGG CAGTTTATTACTGT<u>CAGCAACATTATAGCACTCCTCTCACG</u>TTCGGTGCTGGGACCAAGCTGGAGCT GAAACGG SEQ ID NO.: 53 |
| 12F5 (IgG2aκ) - V$_L$ Chain Seq. | GATGTTGTGATGACCCAAACTCCACTCTCCCTGCCTGTCAGTCTTGGAGATCAAGCCTCCATCTCTT GC<u>AGATCTAGTCAGAGCATTGTACACAGTAATGGAAACACCTATTTACAT</u>TGGTACCTGCAGAAACC AGGCCAGTCTCCAAAGCTCCTGATCTAC<u>AGGGTTTCCAACCGATTTTCT</u>GGGGTCCCAGACAGGTTC AGTGGCAGTGGATCAGGGACAGATTTCACACTCAAGATCAGCAGAGTGGAGGCTGAGGATATGGGAG TTTATTACTGC<u>TTTCAAGGTACACATGTTCCATTCACG</u>TTCGGCTCGGGGACAAAGTTGGAAATAAA ACGG SEQ ID NO.: 54 |
| 19C7 (IgG2aκ) - V$_L$ Chain Seq. | GACATTGTGATGACCCAGTCTCCATCCTCCCTGGCTATGTCAGTAGGACAGAAGGTCACTATGAGTT GC<u>AAGTCCAGTCAGAGCCTTTTAAATAGTAGAAATCAAAAGAACTATTTGGC</u>CTGGTACCAGCAGAA ACCAGGACAGTCTCCTAAACTTCTGGTATA<u>CTTTGCATCCACTAGGGAATCT</u>GGGGTCCCTGATCGC TTCACAGGCAGTGGATCTGGGACAGATTTCACTCTTACCATCAGCAGTGTGCAGGCTGAGGACCTGG CAGTTTATTACTGT<u>CAGCAACATTATAGCACTCCTCTCACG</u>TTCGGTGCTGGGACCAAGCTGGAGCT GAAACGG SEQ ID NO.: 55 |
| ch6B3- - V$_L$ Chain Seq Chain Seq. (IgG1κ) | GACATCGTGATGACCCAGTCCCCCTCCTCCCTGGCCATGTCCGTGGGCCAGAAAGTGACCATGTCCT GC<u>AAGTCCTCCCAGTCCCTGCTGAACTCCCGGAACCAGAAGAACTACCTGG</u>CCTGGTATCAGCAGAA GCCCGGCCAGTCCCCCAAGCTGCTGGTGTAC<u>TTCGCCTCCACCCGCGAGTCC</u>GGCGTGCCCGATAGA TTCACCGGCTCCGGCAGCGGCACCGACTTCACCCTGACCATCTCCAGCGTGCAGGCCGAGGACCTGG CCGTGTACTACTGC<u>CAGCAGCACTACTCCACCCCCCTGACC</u>TTCGGCGCTGGCACCAAGCTGGAACT GAAGCGT SEQ ID NO.: 56 |

TABLE 5-continued

Variable Light Chain DNA Sequences

| hu6B3- - V<sub>L</sub> Chain Seq Chain Seq codon optimised for CHO cell production (IgG1κ) | GACATCGTGATGACCCAGTCCCCCTCCTCCCTGGCCATGTCCGTGGGCGAGCGGGCCACCATCAACT GC<u>AAGTCCTCCCAGTCCCTGCTGAACTCCCGGAACCAGAAGAACTACCTGGCC</u>TGGTATCAGCAGAA GCCCGGCCAGCCTCCCAAGCTGCTGATCTAC<u>TTCGCCTCCACCCGCGAGT</u>CCGGCGTGCCCGATAGA TTCTCCGGCTCCGGCAGCGGCACCGACTTCACCCTGACCATCTCCAGCGTGCAGGCCGAGGACGTGG CCGTGTACTACTGC<u>CAGCAGCACTACTCCACCCCCCTGACC</u>TTCGGCGGAGGCACCAAGGTGGAACT GAAGCGT SEQ ID NO.: 57 |

TABLE 6

Variable Heavy Chain DNA Sequences

| 6B3 (IgG2aκ) - V<sub>H</sub> Chain Seq. | CAGGTTCAGCTGCAGCAGTCTGGAGTTGAGGTGGCGAGGCCTGGGGCTTCAGTGAAGCTGTCCTGCAAG GCTTCT<u>GGCTACACCTTCAGAAGTTATGGTATAACC</u>TGGGTGAGGCAGAGAACTGGACAGGGCCTTGAG TGGATTGGA<u>GAGATTTATCCTAGAAGTGGTAAGACTTACTACAATGAGAAGTTCAAGGGC</u>AAGGCCACA CTGACTGCAGACACATCTTCCAGCACAGTGTACATGGAGCTCCGCAGCCTGACATCTGAGGACTCTGCG GTCTATTTCTGTGCAAGAGA<u>GGGGTATGGTTACGACGGCGGTTACTTTGACTAC</u>TGGGGCCAAGGCACC ACTCTCACAGTCTCCTCA SEQ ID NO. : 58 |
| 11F5 (IgG2aκ) - V<sub>H</sub> Chain Seq. | CAGGTTCAGCTGCAGCAGTCTGGAGCTGAGCTGGCGAGGCCTGGGGCTTCAGTGAAGCTGTCCTGCAAG GCTTCT<u>GGCTACATCTTCATAAGTTATGGTATAAGT</u>TGGGTGAAGCAGAGAACTGGACAGGGCCTTGAG TGGATTGGA<u>GAGATTTATCCTAGAAGTGGGAAAACTTACTACAATGAGAAGTTCAAGGAC</u>AAGGCCGCA CTGACTGCAGACAAATCCTCCAGCATAGCGTACATGGAGCTCCGCAGCCTGACATCTGAGGACTCTGCG GTCTATTTCTGTGCAAGAGA<u>GGGGTATGGTTACGACGGCGGTTACTTTGACTAC</u>TGGGGCCAAGGCACC ATACTCACAGTCTCCTCA SEQ ID NO. : 59 |
| 12F5 (IgG2aκ) - V<sub>H</sub> Chain Seq. | GAAGTCAAGCTGGAGGAGTCTGGAGGAGGCTTGGTGCAACCTGGGGGGTCACGGGAACTCTCTTGTGAA GGCTCA<u>GGGTTCACTTTTAGTGGCTTCTGGATGAGC</u>TGGGTTCGACAGACACCTGGGAAGACCCTGGAG TGGATTGGA<u>GACATTAATTCTGATGGCAGTGCAATAATCTACGCACC</u>ATCCATAAAGGATCGATTCACT ATCTTCAGAGACAATGACAAGAGTACCCTGTACCTGCAGATGAACAATGTGCGATCGGAGGACACAGCC ACGTATTTCTGTATGAGATGG<u>GGGTACTACGGTAGTAACTACTTT</u>GACTACTGGGGCCAAGGCACCACT CTCACAGTCTCCTCA SEQ ID NO.: 60 |
| 19C7 (IgG2aκ) - V<sub>H</sub> Chain Seq. | CAGGTTCAGCTGCAGCAGTCTGGAGTTGAGGTGGCGAGGCCTGGGGCTTCAGTGAAGCTGTCCTGCAAG GCTTCT<u>GGCTACACCTTCAGAAGTTATGGTATAACC</u>TGGGTGAGGCAGAGAACTGGACAGGGCCTTGAG TGGATTGGA<u>GAGATTTATCCTAGAAGTGGTAAGACTTACTACAATGAGAAGTTCAAGGGC</u>AAGGCCACA CTGACTGCAGACACATCTTCCAGCACAGTGTACATGGAGCTCCGCAGCCTGACATCTGAGGACTCTGCG GTCTATTTCTGTGCAAGAGA<u>GGGGTATGGTTACGACGGCGGTTACTTTGACTAC</u>TGGGGCCAAGGCACC ACTCTCACAGTCTCCTCA SEQ ID NO. : 61 |
| ch6B3 (IgG1κ) V<sub>H</sub> Chain Seq. | CAGGTGCAGCTGCAGCAGTCCGGCGTGGAAGTGGCCAGACCTGGCGCCTCCGTGAAGCTGTCCTGCAAG GCCTCC<u>GGCTACACCTTCGGCTCCTACGGCATCACC</u>TGGGTGCGACAGAGAGCGGCCAGGGCCTGGAAT GGATCGGC<u>GAGATCTACCCTCGGAGCGGCAAGACCTACTACAACGAGAAGTTCAAGGGC</u>AAGGCCACCCT GACCGCCGACACCTCCTCCTCCACCGTGTACATGGAACTGCGGTCCCTGACCTCCGAGGACTCCGCCGTG TACTTCTGCGCCAGA<u>GAGGGCTACGGCTACGACGGCGGCTACTTCGACTAC</u>TGGGGCCAGGGCACCACCC TGACAGTGTCCTCC SEQ ID NO. : 62 |
| hu6B3- V<sub>H</sub> Chain Seq codon optimized for CHO cells (IgG1κ) | CAGGTGCAGCTGGTGCAGTCCGGCGCCGAAGTGAAGAAGCCTGGCGCCTCCGTGAAGGTGTCCTGCAAGG CCTCC<u>GGCTACACCTTCAGATCCTACGGCATCACC</u>TGGGTGCGACAGGCCACCGGCCAGGGCCTGGAATG GATGGGC<u>GAAATCTACCCTCGGAGCGGCAAGACCGGCTACGCCCAGAAGTTCCAGGGC</u>AGAGTGACCATG ACCGCCGACACCTCCACCTCCACCGTGTACATGGAACTGCGGTCCCTGCGGTCCGAGGACTCCGCCGTGT ACTTCTGCGCCAGA<u>GAGGGCTACGGCTACGACGGCGGCTACTTCGACTAC</u>TGGGGCCAGGGCACCCTGGT GACAGTGTCCTCC SEQ ID NO.: 63 |

The DNA sequences for the Variable Light and Heavy Chain CDR sequences of 6B3, 11F5, 12F5, 19C7, ch6B3 and hu6B3 are as follows in Tables 7 and 8:

TABLE 7

Variable Light Chain CDR Sequences

| | CDR1 | CDR2 | CDR3 |
|---|---|---|---|
| 6B3 (IgG2aκ) | AAGTCCAGTCAGAGCCTTT TAAATAGTAGAAATCAAAA GAACTATTTGGCC (SEQ ID NO: 64) | TTTGCATCCACTAGGGAATCT (SEQ ID NO: 65) | CAGCAACATTATAGCA CTCCTCTCACG (SEQ ID NO: 66) |

TABLE 7-continued

Variable Light Chain CDR Sequences

| | CDR1 | CDR2 | CDR3 |
|---|---|---|---|
| 11F5 (IgG2aκ) | AAGTCCAGTCAGAGCCTTT TAAATAGTAGCAATCAAAA GAACTATTTGGCC (SEQ ID NO: 67) | TTTGCATCCACTAGGGACTCT (SEQ ID NO: 68) | CAGCAACATTATAGCA CTCCTCTC (SEQ ID NO: 69) |
| 12F5 (IgG2aκ) | AGATCTAGTCAGAGCATTG TACACAGTAATGGAAACAC CTATTTACAT (SEQ ID NO: 70) | AGGGTTTCCAACCGATTTTCT (SEQ ID NO: 71) | TTTCAAGGTACACATG TTCCATTCACG (SEQ ID NO: 72) |
| 19C7 (IgG2aκ) | AAGTCCAGTCAGAGCCTTT TAAATAGTAGAAATCAAAA GAACTATTTGGCC (SEQ ID NO: 73) | TTTGCATCCACTAGGGAATCT (SEQ ID NO: 74) | CAGCAACATTATAGCA CTCCTCTCACG (SEQ ID NO: 75) |
| ch6B3 (IgG1κ) | AAGTCCTCCCAGTCCCTGC TGAACTCCCGGAACCAGAA GAACTACCTGGCC (SEQ ID NO: 76) | TTCGCCTCCACCCGCGAGTCC (SEQ ID NO: 77) | CAGCAGCACTACTCCA CCCCCCTGACC SEQ ID NO: 78) |
| hu6B3-codon optimized for CHO cells (IgG1κ) | AAGTCCTCCCAGTCCCTGCTG AACTCCCGGAACCAGAAGAAC TACCTGGCC (SEQ ID NO: 79) | TTCGCCTCCACCCGCGAGTCC (SEQ ID NO: 80) | CAGCAGCACTACTCCACCCCC CTGACC (SEQ ID NO: 81) |

TABLE 8

Variable Heavy Chain CDR Sequences

| | CDR1 | CDR2 | CDR3 |
|---|---|---|---|
| 6B3 (IgG2aκ) | GGCTACACCTTCAGAAGTTA TGGTATAACC (SEQ ID NO: 82) | GAGATTTATCCTAGAAGTGGTA AGACTTACTACAATGAGAAGTT CAAGGGC (SEQ ID NO: 83) | GAGGGGTATGGTTACGACGGCGGT TACTTTGACTAC (SEQ ID NO: 84) |
| 11F5 (IgG2aκ) | GGCTACATCTTCATAAGTTA TGGTATAAGT (SEQ ID NO: 85) | GAGATTTATCCTAGAAGTGGGA AAACTTACTACAATGAGAAGTT CAAGGAC (SEQ ID NO: 86) | GAGGGGTATGGTTACGACGGCGGT TACTTTGACTAC (SEQ ID NO: 87) |
| 12F5 (IgG2aκ) | GGGTTCACTTTTAGTGGCTT CTGGATGAGC (SEQ ID NO: 88) | GACATTAATTCTGATGGCAGTG CAATAATCTACGCACCATCCAT AAAGGAT (SEQ ID NO: 89) | TGGGGGTACTACGGTAGTAACTAC TTTGACTAC (SEQ ID NO: 90) |
| 19C7 (IgG2aκ) | GGCTACACCTTCAGAAGTTA TGGTATAACC (SEQ ID NO: 91) | GAGATTTATCCTAGAAGTGGTA AGACTTACTACAATGAGAAGTT CAAGGGC (SEQ ID NO: 92) | GAGGGGTATGGTTACGACGGCGGT TACTTTGACTAC (SEQ ID NO: 93) |
| ch6B3 (IgG1κ) | GGCTACACCTTCGGCTCCTA CGGCATCACC (SEQ ID NO: 94) | GAGATCTACCCTCGGAGCGGCA AGACCTACTACAACGAGAAGTT CAAGGGC (SEQ ID NO: 95) | GAGGGCTACGGCTACGACGGCGGC TACTTCGACTAC (SEQ ID NO: 96) |
| hu6B3-codon optimized for CHO cells (IgG1κ) | GGCTACACCTTCAGATCCTA CGGCATCACC (SEQ ID NO: 97) | GAAATCTACCCTCGGAGCGGCA AGACCGGCTACGCCCAGAAGTT CCAGGGC (SEQ ID NO: 98) | GAGGGCTACGGCTACGACGGCGGC TACTTCGACTAC (SEQ ID NO: 99) |

The isolated nucleic acid molecule(s) (polynucleotides), encode a biologically relevant portion of 6B3, 11F5, 12F5, 19C7, ch6B3, hu6B3, or affinity matured version or otherwise mutated version of 6B3, 11F5, 12F5, 19C7, ch6B3, hu6B3, or other anti-PDGF-C antibodies discussed herein. To this end, the isolated nuclei acid molecules(s) may include one or more of the foregoing DNA sequences, a fragment of one or more of the foregoing sequences, or a nucleic acid sequence that at least 70% homologous, 80% homologous, 90% homologous or 99% homologous to one or more of the foregoing.

Variant antibodies also are included within the scope of the invention. Thus, variants of the sequences recited in the application also are included within the scope of the invention. Further variants of the antibody sequences having improved affinity can be obtained using methods known in the art and are included within the scope of the invention. For example, amino acid substitutions can be used to obtain antibodies with further improved affinity. Alternatively, codon optimization of the nucleotide sequence can be used to improve the efficiency of translation in expression systems for the production of the antibody.

In certain embodiments, an antibody of the invention comprises a heavy chain variable region comprising CDR1, CDR2 and CDR3 sequences, and a light chain variable region comprising CDR1, CDR2 and CDR3 sequences, wherein one or more of these CDR sequences comprise specified amino acid sequences based on the preferred antibodies described herein, or conservative modifications thereof, and wherein the antibodies retain the desired functional properties of binding to PDGF-C and/or PDGF-CC.

A conservative modification or functional equivalent of a peptide, polypeptide, or protein disclosed in this invention refers to a polypeptide derivative of the peptide, polypeptide, or protein, e.g., a protein having one or more point mutations, insertions, deletions, truncations, a fusion protein, or a combination thereof. It retains substantially the activity to of the parent peptide, polypeptide, or protein (such as those disclosed in this invention). In general, a conservative modification or functional equivalent is at least 70% (e.g., any number between 70% and 100%, inclusive, e.g., 70%, 80%, 85%, 90%, 95%, and 99%) identical to a parent (e.g., one of the sequences disclosed herein).

As used herein, the term "conservative modifications" refers to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine).

Thus, one or more amino acid residues within the CDR regions of an antibody of the invention can be replaced with other amino acid residues from the same side chain family and the altered antibody can be tested for retained function using the functional assays described herein.

Other modifications of the antibody are contemplated herein. For example, the antibody can be linked to one of a variety of nonproteinaceous polymers, for example, polyethylene glycol, polypropylene glycol, polyoxyalkylenes, or copolymers of polyethylene glycol and polypropylene glycol. The antibody also can be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in, for example, Remington's Pharmaceutical Sciences, 16th edition, Oslo, A., Ed., (1980).

Nucleic acids of the present invention may be substantially free from other nucleic acids. For most cloning purposes, DNA is a preferred, but non-limiting, nucleic acid. One or a combination of the foregoing DNA molecules may be subcloned into an expression vector and subsequently transfected into a host cell of choice wherein the recombinant host cell provides a source for substantial levels of a relevant portion of the 6B3, 11F5, 12F5, 19C7, ch6B3, hu6B3 or anti-PDGF-C antibody of the present invention, or the affinity matured version thereof. Such procedures may be used for a variety of utilities, such as generating scFvs or for co-expressing these $V_H$ and $V_L$ chains in a mammalian expression vector system which encodes human $C_H$ and $C_L$ regions, of for example, an IgG antibody. The degeneracy of the genetic code is such that, for all but two amino acids, more than a single codon encodes a particular amino acid. This allows for the construction of synthetic DNA that encodes an antibody of the present invention where the nucleotide sequence of the synthetic DNA differs significantly from the nucleotide sequences disclosed herein, but still encodes such an antibody. Such synthetic DNAs are intended to be within the scope of the present invention. If it is desired to express such synthetic DNAs in a particular host cell or organism, the codon usage of such synthetic DNAs can be adjusted to reflect the codon usage of that particular host, thus leading to higher levels of expression of the an antibody of the present invention. In other words, this redundancy in the various codons which code for specific amino acids is within the scope of the present invention. Therefore, this invention is also directed to those DNA sequences which encode RNA comprising alternative codons which code for the eventual translation of the identical amino acid, as shown below: A=Ala=Alanine: codons GCA, GCC, GCG, GCU; C=Cys=Cysteine: codons UGC, UGU; D=Asp=Aspartic acid: codons GAC, GAU E=Glu=Glutamic acid: codons GAA, GAG; F=Phe=Phenylalanine: codons UUC, UUU; G=Gly=Glycine: codons GGA, GGC, GGG, GGU; H=His=Histidine: codons CAC, CAU; I=Ile=Isoleucine: codons AUA, AUC; AUU; K=Lys=Lysine: codons AAA, AAG; L=Leu=Leucine: codons UUA, UUG, CUA, CUC, CUG, CUU; M=Met=Methionine: codon AUG; N=Asp=Asparagine: codons GAU, GAC; P=Pro=Proline: codons CCA, CCC, CCG, CCU; Q=Gln=Glutamine: codons CAA, CAG; R=Arg=Arginine: codons AGA, AGG, CGA, CGC, CGG, CGU; S=Ser=Serine: codons AGC, AGU, UCA, UCC, UCG, UCU; T=Thr=Threonine: codons ACA, ACC, ACG, ACU; V=Val=Valine: codons GUA, GUC, GUG, GUU; W=Trp=Tryptophan: codon UGG; Y=Tyr=Tyrosine: codons UAC, UAU. Such recombinant expression vectors may then be stably or transiently transfected into an appropriate cell line for the generation of alternative antibody form.

The present invention notes the existence of codon redundancy that may result in differing DNA molecules expressing an identical antibody or portion thereof (e.g., alternative nucleic acid molecules encoding an identical scFv or a $V_H$ and/or $V_L$ portion of an IgG). For purposes of this specification, a sequence bearing one or more replaced codons will be defined as a degenerate variation. Another source of sequence variation may occur through RNA editing. Such RNA editing may result in another form of codon redundancy, wherein a change in the open reading frame does not result in an altered amino acid residue in the expressed protein. Also included within the scope of this invention are mutations either in the DNA sequence or the translated antibody which improve the ultimate physical properties of the expressed antibody. To this end, the present invention relates to (i) affinity matured versions of anti-PDGF-C antibody, including but not limited to 6B3, 11F5, 12F5, 19C7, ch6B3 or hu6B3, and/or (ii) mutated forms of an anti-PDGF-C antibody, including but not limited to 6B3, 11F5, 12F5, 19C7, ch6B3, or hu6B3, including but not limited to one or more mutations in the CDR1, CDR2 and/or CDR3 regions as generated through known affinity maturation methodology and recombinant DNA techniques known for introducing site specific mutation. Such isolated or purified nucleic acid molecules will represent the $V_H$ and/or $V_L$ portions of the anti-PDGF-C antibody. These nucleic acids are substantially free from other nucleic acids and may be cloned in accordance with the foregoing.

The present invention also relates to recombinant vectors and recombinant hosts, both prokaryotic and eukaryotic, which contain nucleic acid molecules encoding the respective heavy and/or light regions (or fragments thereof) of an anti-PDGF-C antibody. These nucleic acid molecules, in whole or in part, can be linked with other DNA molecules (i.e., DNA molecules which encompass immunoglobulin genes used for generation of a recombinant human antibody) that are not naturally linked, to form "recombinant DNA molecules" which encode a respective human recombinant antibody. These vectors may be comprised of DNA or RNA. For most cloning purposes DNA vectors are preferred. Typical vectors include plasmids, modified viruses, bacteriophage, cosmids, yeast artificial chromosomes, and other forms of episomal or integrated DNA. It is within the purview of the skilled artisan to determine an appropriate vector for a particular gene transfer, generation of a recombinant human antibody or other use. Methods of subcloning nucleic acid molecules of interest into expression vectors, transforming or transfecting host cells containing the vectors, and methods of making substantially pure protein comprising the steps of introducing the respective expression vector into a host cell, and cultivating the host cell under appropriate conditions are well known. The antibody (such as an IgG recombinant human antibody) so produced may be harvested from the host cells in conventional ways. Any known expression vector may be utilized to practice this portion of the invention, including any vector containing a suitable promoter and other appropriate transcription regulatory elements. The resulting expression construct is transferred into a prokaryotic or eukaryotic host cell to produce recombinant protein. Expression vectors are defined herein as DNA sequences that are required for the transcription of cloned DNA and the translation of their mRNAs in an appropriate host. Such vectors can be used to express eukaryotic DNA in a variety of hosts such as bacteria, blue green algae, plant cells, insect cells and animal cells. Specifically designed vectors allow the shuttling of DNA between hosts such as bacteria-yeast or bacteria-animal cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Techniques for such manipulations can be found described in Sambrook, et al. (1989, Molecular Cloning. A Laboratory Manual; Cold Spring Harbor Laboratory, Cold Spring Harbor, N.Y.) are well known and available to the artisan of ordinary skill in the art. Expression vectors may include, but are not limited to, cloning vectors, modified cloning vectors, specifically designed plasmids or viruses. Commercially available mammalian expression vectors which may be suitable, include, but are not limited to, pcDNA3.neo (Invitrogen), pcDNA3.1 (Invitrogen), pCI-neo (Promega), pLITMUS28, pLITMUS29, pLITMUS38 and pLITMUS39 (New England Bioloabs), pcDNAI, pcDNAIanp (Invitrogen), pcDNA3 (Invitrogen), pMClneo (Stratagene), pXT1 (Stratagene), pSG5 (Stratagene), EBO pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and 1ZD35 (ATCC 37565). Also, a variety of bacterial expression vectors are available, including but not limited to pCR2.1 (Invitrogen), pET1 1a (Novagen), lambda gt1 1 (Invitrogen), and pKK223-3 (Pharmacia). In addition, a variety of fungal cell expression vectors may be used, including but not limited to pYES2 (Invitrogen) and Pichie expression vector (Invitrogen). Also, a variety of insect cell expression vectors may be used, including but are not limited to pBlueBacIII and pBlueBacHis2 (Invitrogen), and pAcG2T (Pharmingen).

Recombinant host cells may be prokaryotic or eukaryotic, including but not limited to, bacteria such as *E. coli*, fungal cells such as yeast, mammalian cells including, but not limited to, cell lines of bovine, porcine, monkey and rodent origin; and insect cells. Mammalian species which may be suitable, include but are not limited to, L cells L-M(TK-) (ATCC CCL1.3), L cells L-M (ATCC CCL 1.2), Saos-2 (ATCC HTB-85), 293 (ATCC CRL1573), Raji (ATCC CCL 86), CV-1 (ATCC CCL 70), COS-1 (ATCC CRL1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26), MRC-5 (ATCC CCL171) and CPAE (ATCC CCL 209).

The antibodies of the present invention may also be adapted or specifically engineered to form variants of the foregoing, including, but not limited to, a polyclonal, alternative monoclonal, chimeric, and/or humanized antibodies. Isolated or variant antibodies of the invention may include single variable domains (sVDs) and antigen binding proteins that comprise sVDs. sVD binding sites can be obtained from antigen specific Fv regions (which comprise both $V_H$ and $V_L$ domains). Often, it can be shown that the binding affinity and specificity of an Fv region is contributed primarily by one of the variable domains. Alternatively, the scFv can be obtained directly. Direct sources of sVDs include mammals (e.g., camelids) that naturally express antibodies containing only $V_H$ domain. Further, phage display libraries can be constructed to express only a single variable domain. For example, a human domain antibody phage display library is commercially available from Domantis (Cambridge, UK).

Chimeric antibodies, such as ch6B3, may generally comprise variable domains of one antibody and constant domains of a different antibody. Typically, to minimize host immune responses against the antibody and to enhance host responses against the antibody target by retaining antibody effector functions, the constant domains of a chimeric antibody are taken from the same species to which the chimeric antibody will be administered.

Humanized antibodies such as hu6B3 are a form of a chimeric protein that are constructed such that the variable domains include one or more complementarity determining regions (CDRs) of non-human origin that are grafted to human framework regions. To this end, and in certain embodiments, is may be generated by various means of recombinant DNA technology and non-human transgenics that are well known in the art. Such methodology is utilized to generate an antibody from one or the following origins: (i) a scFv or alternative antibody isolated from a combinatorial human antibody library; (ii) a partial or complete antibody generated from a respective expression vector stably or transiently transfected into a host cell, preferably a mammalian host cell (e.g., subcloning nucleotide sequences encoding $V_H$ and $V_L$ chains into an expression vector in conjunction with respective $C_H$ and $C_L$ nucleotide sequences, so as to promote expression of a predetermined form of antibody showing specificity to PDGF-CC); and/or (iii) an antibody isolated from a non-human transgenic animal which contains human immunoglobulin genes, or by any other known methodology which relies of the recombinant 'mixing and matching' of human immunoglobulin gene sequences to other DNA sequences in order to generate the human recombinant antibody of interest.

A humanized construct is valuable for elimination of adverse immunogenic characteristics, for example, where an antigen binding domain from a non-human source is desired to be used for treatment in a human. Variable domains have a high degree of structural homology, allowing easy identification of amino acid residues within variable domains which correspond to CDRs and FRs.

Methods have been developed to preserve or to enhance affinity for such variant antibodies, particularly, though not exclusively, the chimeric and/or humanized forms. One way is to include in the recipient variable domain the foreign framework residues that influence the conformation of the CDR regions. A second way is to graft the foreign CDRs onto human variable domains with the closest homology to the foreign variable region. CDRs are most easily grafted onto different framework regions by first amplifying individual FR sequences using overlapping primers which include desired CDR sequences, and joining the resulting gene segments in subsequent amplification reactions. Grafting of a CDR onto a different variable domain can further involve the substitution of amino acid residues which are adjacent to the CDR in the amino acid sequence or packed against the CDR in the folded variable domain structure which affect the conformation of the CDR. Humanized variable domains of the invention therefore include human domains which comprise one or more non-human CDRs as well as such domains in which additional substitutions or replacements have been made to preserve or enhance binding characteristics.

Antibodies of the present invention may also employ variable domains that have been made less immunogenic by replacing surface-exposed residues so as to make the antibody appear as self to the immune system. Antibodies have been modified by this process with no loss of affinity. Because the internal packing of amino acid residues in the vicinity of the antigen binding site remains unchanged, affinity is preserved. Substitution of surface-exposed residues according to the invention for the purpose of reduced immunogenicity does not mean substitution of CDR residues or adjacent residues which influence binding characteristics.

In any of the foregoing embodiments, the variable regions, CDRs, and constant regions incorporated into antibodies can be subject to in vitro or in vivo mutation and screening procedures in order to modify affinity and/or specificity. Thus, binding domains of the invention include those for which binding characteristics have been improved by mutating CDRs and/or FR regions by direct mutation, methods of affinity maturation, or chain shuffling. It is understood that amino acid residues that are primary determinants of binding of single domain antibodies can be within Kabat defined CDRs, but may include other residues as well. For sVDs, residues important for antigen binding can also potentially include amino acids that would otherwise be located at the interface of a $V_H$-$V_L$ heterodimer. Typically, phage display is used to screen such mutants to identify those having the desired binding characteristics (see, e.g., Yang et al., J. Mol. Biol., 254: 392-403 (1995)). Mutations can be made in a variety of ways. One way is to randomize individual residues or combinations of residues so that in a population of otherwise identical sequences, all twenty amino acids or a subset thereof are found at particular positions. Alternatively, mutations may be induced over a range of CDR residues by error prone PCR methods (see, e.g., Hawkins et al., J. Mol. Biol., 226: 889-896 (1992)). For example, phage display vectors containing heavy and light chain variable region genes may be propagated in mutator strains of E. coli (see, e.g., Low et al., J. Mol. Biol., 250: 359-368 (1996)). These methods of mutagenesis are illustrative of the many methods known to one of skill in the art.

Although the invention has been described with reference to certain embodiments, it will be understood by those skilled in the art that various changes may be made and equivalents may be substituted for elements thereof without departing from the scope of the invention. In addition, many modifications may be made to adapt to a particular situation or material to the teachings of the invention without departing from the essential scope thereof. Therefore, it is intended that the invention not be limited to the particular embodiments disclosed, but that the invention will include all embodiments falling within the scope of the appended claims or any claims later added.

In addition to the foregoing, the anti-PDGF-C antibodies of the present invention may be used alone or within compositions for a wide array uses. In certain aspects, antibodies and compositions containing antibodies of the present invention may be used for treating a patient diagnosed with a PDGF-C expressing cell type, diagnosis of a PDGF-C expressing cell or carcinoma, detection of PDGF-C expression in a cell, screening for and selecting alternative PDGF-C binding compounds, or the like. The following elaborates on such uses, but is not to be considered limiting to the uses of the anti-PDGF-C antibodies of the present invention. To this end, one of skill in the art will readily appreciate that the antibodies of the present invention may be provided with any use otherwise known in the art.

Treatment Methods and Pharmaceutical Formulations

In certain aspects, the anti-PDGF-C antibodies of the present invention may be administered to a subject for preventing angiogenesis in the subject or for reducing the size of a solid tumor in the subject by binding to and inhibiting the activity of PDGF-CC. For example, the anti-PDGF-C antibodies of the present invention can be administered to reduce PDGF-CC-mediated activities within a cell or to reduce autocrine and/or paracrine signaling of the cell/tumor or to reduce PDGF-CC signaling in the blood-brain barrier. Many tumor cells, for example, use PDGF-CC autocrine and/or paracrine signaling to effectuate vascularization, stromal support, or other tumor effects that ultimately contribute to tumor cell viability and/or tumor growth. The anti-PDGF-C antibodies of the present invention may be administered to a patient with a PDGF-C expressing carcinoma to reduce, inhibit, or prevent PDGF-CC mediated signaling, ultimately, resulting in a reduction of vascularization, stromal support, etc. and a reduction of tumor size and/or cell viability.

Non-limiting examples of PDGF-C expressing cell types include cancers of the head, neck, eye, mouth, throat, esophagus, bronchus, larynx, pharynx, chest, bone, lung, colon, rectum, stomach, prostate, urinary bladder, uterine, cervix, breast, ovaries, testicles or other reproductive organs, skin, thyroid, blood, lymph nodes, kidney, liver, pancreas, and brain or central nervous system. In certain non-limiting aspects, such cell types include Bladder Transitional cell carcinoma (TCC), Breast Invasive Ductal Carcinoma (IDC), Breast Invasive Lobular Carcinoma (ILC), Colorectal Adenocarcinoma, Glioblastoma Multiforme, Gliosarcoma, Hepatocellular Carcinoma, Lung Adenocarcinoma, Lung Squamous Cell Carcinoma (SqCC), Metastatic Melanoma, Mesothelioma, Ovarian Adenocarcinoma, Pancreatic Adenocarcinoma, Prostate Adenocarcinoma, Renal Cell Cancer, Uterine Adenocarcinoma, and the like. The use of the antibodies of the present invention, however, is not necessarily limited to the treatment of cancer cell types and such antibodies also may be administered to treat any PDGF-CC-associated disease-state and/or condition, by inhibiting the activity of PDGF-CC in or secreted from a cell. Non-limiting examples of such conditions include modulation of the integrity of the blood-brain barrier (BBB) of the central nervous system (CNS) (brain, spinal cord and retina of the eye), atherosclerosis and fibrosis.

In other aspects, the anti-PDGF-C antibodies of the present invention may be administered to a subject for treating disorders or conditions associated with compromised BBB. Accordingly, the methods and compositions of the present invention can be used to treat CNS disease such as brain edema, stroke, ischemic retinopathies, diabetic retinopathy, Alzheimer's disease, multiple sclerosis, and tumors of the CNS. The method of the present invention is especially suitable for treating cerebral edema, pulmonary embolism, cardiovascular diseases, head trauma, infection, neurological diseases, or other diseases where edema is a significant clinical problem. In a particularly preferred embodiment, the present invention is used for the treatment of cerebral edema. The method of the present invention may also be used for treating localized or restricted edema, such as edema ascites, hydrothorax, hydropericardium, cerebral edema, hydrocephalus, glaucoma, or acute pulmonary edema, as well as generalized or systemic, such as anasarca or hydrops.

Cerebral or brain edemas that may benefit from anti-PDGF-CC treatment of the present invention additionally may include but are not limited to ischemic brain edema due to cerebral malaria infection, which kills many children in developing countries (see Penet et al., Imaging experimental cerebral malaria in vivo: significant role of ischemic brain edema. J. Neurosci. 2005; 25:7352-8); brain edema in acute hepatic failure (see Vaquero et al., Brain edema in acute liver failure. A window to the pathogenesis of hepatic encephalopathy. Ann. Hepatol. 2003 2:12-22); edema resulted from brain surgery, which in many aspects resembles brain trauma; edema caused by intracranial tumors (see Papadopoulos et al., Molecular mechanisms of brain tumor edema. Neuroscience. 2004; 129:1011-20; and high altitude cerebral edema (see Hackett and Roach. High altitude cerebral edema. High. Alt. Med. Biol. 2004 5:136-46).

Preferably, an anti-PDGF-C antibody or a pharmaceutical composition comprising the antibody is delivered to the edema sites, for example by direct injection into the cerebrospinal fluid (CSF) in the case of cerebral edema, or via intravascular administration or even intranasal delivery which has been demonstrated to successfully reach the BBB.

In a preferred embodiment, administration is intravenously, intrathecally or via nasal administration (intranasally). Particularly, for the treatment of cerebral edema or in combination therapy of ischemic stroke, preferred administration modes for delivery to vascular bed in the area of the blood brain barrier, is intrathecal or intranasal administration. As used herein, the term "intrathecal administration" includes delivering a PDGF-C antibody in a pharmaceutical formulation directly into the cerebrospinal fluid of a subject, by techniques including lateral cerebroventricular injection through a burrhole or cisternal into the cisterna magna or lumbar puncture into the lumbar regions or the like, as described, for example, in Lazorthes et al., Advances in Drug Delivery Systems and Applications in Neurosurgery, 143-192, and Omaya et al., Cancer Drug Delivery, 1: 169-179). The term "lumbar region" is intended to include the area between the third and fourth lumbar (lower back) vertebrae. The term "cisterna magna" is intended to include the area where the skull ends and the spinal cord begins at the back of the head. The term "cerebral ventricle" means the cavities in the brain that are continuous with the central canal of the spinal cord. Administration of a PDGF-C antibody to any of the above mentioned sites can be achieved by direct injection of the antibody or by the use of infusion pumps. See, e.g., U.S. Pat. Nos. 8,765,671 and 8,147,828, the contents of which are incorporated by reference.

For treating disorders or conditions associated with compromised BBB, a PDGF-C antibody disclosed herein can be used in combination with other therapeutics, such as tPA, in the manner described in U.S. Pat. Nos. 8,765,671 and 8,147,828, the contents of which are incorporated by reference.

The term "treatment" refers to both therapeutic and prophylactic measures. Those in need of treatment include those already afflicted with the disease or disorder as well as those in which the disease or disorder is to be prevented. The subject to be treated may have been diagnosed as having the disease or disorder or may be predisposed or susceptible to the disease.

Administration of the anti-PDGF-C antibodies may be alone or in combination with existing therapeutic regimens. With carcinomas, for example, the additional therapeutic regimens can include one or a plurality of chemotherapeutic agents otherwise known in the art. Those skilled in the art are readily able to determine standard dosages and scheduling for each of these regimens.

In conjunction with one or more of the foregoing treatment regimes, a pharmaceutical composition comprising an effective amount one more of the anti-PDGF-C antibodies of the present invention, or an affinity matured version thereof, may be administered to provide a prophylactic or therapeutic treatment by inhibiting PDGF-CC activity. The antibody-based pharmaceutical composition of the present invention may be formulated by any number of strategies known in the art (e.g., see McGoff and Scher, 2000, *Solution Formulation of Proteins/Peptides*: In McNally, E. J., ed. *Protein Formulation and Delivery*. New York, N.Y.: Marcel Dekker; pp. 139-158; Akers and Defilippis, 2000, *Peptides and Proteins* as *Parenteral Solutions*. In: *Pharmaceutical Formulation Development of Peptides and Proteins*. Philadelphia, Pa.: Talyor and Francis; pp. 145-177; Akers, et al., 2002, *Pharm. Biotechnol.* 14:47-127). A pharmaceutically acceptable composition suitable for patient administration will contain an effective amount of the antibody in a formulation which both retains biological activity while also promoting maximal stability during storage within an acceptable temperature range. The pharmaceutical compositions can also include, depending on the formulation desired, pharmaceutically acceptable diluents, pharmaceutically acceptable carriers and/or pharmaceutically acceptable excipients, or any such vehicle commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution or the like. The amount of an excipient that is useful in the pharmaceutical composition or formulation of this invention is an amount that serves to uniformly distribute the antibody throughout the composition so that it can be uniformly dispersed when it is to be delivered to a subject in need thereof. It may serve to dilute the antibody to a concentration that provides the desired beneficial palliative or curative results while at the same time minimizing any adverse side effects that might occur from too high a concentration. It may also have a preservative effect. Thus, for the antibody having a high physiological activity, more of the excipient will be employed. On the other hand, for any active ingredient(s) that exhibit a lower physiological activity, a lesser quantity of the excipient will be employed. In general, the amount of excipient in the composition will be between about 50% weight (w) and 99.9% wt of the total composition. If the antibody exhibits a particularly low physiological activity, the amount of excipient could be as little as 1% wt. On the other hand, for an antibody that has a particularly high physiological activity, the amount of excipient may be between about 98.0% and about 99.9% wt. In addition, the antibody or antibodies may be administered in the form of a "chemical derivative" (a molecule that contains additional chemical moieties which are not normally a part of the base molecule). Such moieties may improve the solubility, half-life, absorption, etc. of the biological agent. Alternatively, these moieties may attenuate undesirable side effects of the antibody.

Pharmaceutical compositions can also include large, slowly metabolized macromolecules such as proteins, polysaccharides, polylactic acids, polyglycolic acids and copolymers (such as latex functionalized sepharose, agarose, cellulose, and the like), polymeric amino acids, amino acid copolymers, and lipid aggregates (such as oil droplets or liposomes). Additionally, these carriers can function as immunostimulating agents (i. e., adjuvants). For parenteral administration, agents of the invention can be administered as injectable dosages of a solution or suspension of the substance in a physiologically acceptable diluent with a pharmaceutical carrier which can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions.

The antibody formulation may be in liquid form or solid form. A solid formulation is generally lyophilized and brought into solution prior to administration for either single or multiple dosing. The formulations should not be exposed to extreme temperature or pH so as to avoid thermal denaturation. Thus, it is essential to formulate an antibody composition of the present invention within a biologically relevant pH range. A solution buffered to maintain a proper pH range during storage is indicated, especially for liquid formulations stored for longer periods of time between formulation and administration. To date, both liquid and solid formulations require storage at lower temperatures (usually 2-8° C.) in order to retain stability for longer periods. Formulated antibody compositions, especially liquid formulations, may contain a bacteriostat to prevent or minimize proteolysis during storage, including but not limited to effective concentrations (usually <1% w/v) of benzyl alcohol, phenol, m-cresol, chlorobutanol, methylparaben, and/or propylparaben. A bacteriostat may be contraindicated for some patients. Therefore, a lyophilized formulation may be reconstituted in a solution either containing or not containing such a component. Additional components may be added to either a buffered liquid or solid antibody formulation, including but not limited to sugars as a cryoprotectant (including but not necessarily limited to polyhydroxy hydrocarbons such as sorbitol, mannitol, glycerol and dulcitol and/or disaccharides such as sucrose, lactose, maltose or trehalose) and, in some instances, a relevant salt (including but not limited to NaCl, KCl or LiCl). Such antibody formulations, especially liquid formulations slated for long term storage, will rely on a useful range of total osmolarity to both promote long term stability at temperature of 2-8° C., or higher, while also making the formulation useful for parenteral injection. An effective range of total osmolarity (the total number of molecules in solution) is from about 200 mOs/L to about 800 mOs/L. It will be apparent that the amount of a cyroprotectant, such as sucrose or sorbitol, will depend upon the amount of salt in the formulation in order for the total osmolarity of the solution to remain within an appropriate range. Therefore a salt free formulation may contain from about 5% to about 25% sucrose, with a preferred range of sucrose from about 7% to about 15%, with an especially preferred sucrose concentration in a salt free formulation being from 10% to 12%. Alternatively, a salt free sorbitol-based formulation may contain sorbitol within a range from about 3% to about 12%, with a preferred range from about 4% to 7%, and an especially preferred range is from about 5% to about 6% sorbitol in a salt-free formulation. Salt-free formulations will of course warrant increased ranges of the respective cryoprotectant in order to maintain effective osmolarity levels. These formulation may also contain a divalent cation (including but not necessarily limited to $MgCl_2$, $CaCl_2$) and $MnCl_2$); and a non-32 ionic surfactant (including but not necessarily limited to Polysorbate-80 (Tween 80®), Polysorbate-60 (Tween 60®), Polysorbate-40 (Tween 40®) and Polysorbate-20 (Tween 20®), polyoxyethylene alkyl ethers, including but not limited to Brij 58®, Brij 35®, as well as others such as Triton X-100®, Triton X 114®, NP40®, Span 85 and the Pluronic series of non-ionic surfactants (e.g., Pluronic 121)). Any combination of such components, including probable inclusion of a bacteriostat, may be useful to fill the antibody-containing formulations of the present invention.

Numerous examples of various other carriers, diluents, excipients and the such are known in the art and are disclosed in references cited herein, as well as *Remington's Pharmaceutical Sciences* (18th ed.; Mack Publishing Company, Easton, Pa., 1990), the contents of which are incorporated herein by reference. Briefly, it will be appreciated that suitable carriers, excipients, and other agents may be incorporated to formulate the pharmaceutical compositions to provide improved transfer, delivery, tolerance, and the like. The methods of incorporating the biological agent and/or additional active ingredient(s) into the carrier are known to a person of ordinary skill in the art and depend on the nature of the biological agent and the nature of the carrier selected by a person practicing the current invention. Ionic binding, gel encapsulation or physical trapping inside the carrier, iontophoresis and soaking the carrier in a solution of the biological agent are suitable examples contemplated in formulating a pharmaceutical composition to be used to practice of the disclosed treatment methods. Alternatively, the carrier may be little more than a diluent for the biological agent. These formulations may include for example, powders, pastes, ointments, jelly, waxes, oils, lipids, anhydrous absorption bases, oil-in-water or water-in-oil emulsions, emulsions carbowax (polyethylene glycols of a variety of molecular weights), semi-solid gels, and semi-solid mixtures containing carbowax. The dosage regimen utilizing the compounds of the present invention is selected in accordance with a variety of factors including type, species, age, weight, sex and medical condition of the patient; the severity of the condition to be treated; the route of administration; the renal, hepatic and cardiovascular function of the patient; and the particular biological agent thereof employed. A physician or veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug. Any of the foregoing formulations may be appropriate in treatments and therapies in accordance with the present invention, provided that the active ingredient in the formulation is not inactivated by the formulation and the formulation is physiologically compatible.

The pharmaceutical compositions of the present invention may be administered to the host in any manner, strategy and/or combination available in the art in amounts sufficient to offer a therapeutic treatment by inhibiting PDGF-CC activity, i.e. reduction of tumor size, decrease of angiogenesis, etc. These compositions may be provided to the individual by a variety of routes known in the art, especially parenteral routes, including but in no way limited to parenteral routes such as intravenous (IV), intramuscular (IM); or subcutaneous (SC) administration, with IV administration being the norm within the art of therapeutic antibody administration. These compositions may be administered as separate or multiple doses (i.e., administration of the antibody at staggered times by maintaining the sterile condition of the formulation through the treatment regime). The dosage regimen utilizing the compounds of the present invention is selected in accordance with a variety of factors including type, species, age, weight, sex and medical condition of the patient (such as a human patient); the severity of the condition to be treated; the route of administration; the renal, hepatic and cardiovascular function of the patient; and the particular antibody thereof employed. A physician or veterinarian of ordinary skill can readily determine and prescribe the effective therapeutic amount of the antibody. Optimal precision in achieving concentrations of antibody within the range that yields efficacy without toxicity requires a regimen based on the kinetics of the drug's availability to target sites. This involves a consideration of the distribution, equilibrium, and elimination of a drug. Antibodies described herein may be used alone at appropriate dosages. Alternatively, co-administration or sequential administration of other agents may be desirable. It will be possible to present a therapeutic dosing regimen for the antibodies of the present invention in conjunction with administration of alternative prophylactic or therapeutic regimes. An effective dosage regime will vary depending upon many different factors, including means of administration, target site, physiological state of the patient, whether the patient is human or an animal, other medications administered, and whether treatment is prophylactic or therapeutic. For administration of an anti-PDGF-C antibody, the dosage ranges from about 0.0001 to 100 mg/kg, and more usually 0.01 to 5 mg/kg of the host body weight.

Another aspect regarding delivery and dosage regimes for an anti-PDGF-C antibody composition of the present invention relates to drug delivery via parenteral routes, which may include non-injectable and injectable devices. Typically, injectable compositions are prepared as either liquid solutions or suspensions; solid forms suitable for solution in, or suspension in, liquid vehicles prior to injection can also be prepared. The preparation also can be emulsified or encapsulated in liposomes or microparticles such as polylactide, polyglycolide, or copolymer for enhanced adjuvant effect, as discussed above (see Langer, 1990, *Science* 249: 1527-1523; and Hanes, 1997, *Advanced Drug Delivery Reviews* 28: 97-119). The agents of this invention can be administered in the form of a depot injection or implant preparation which can be formulated in such a manner as to permit a sustained or pulsatile release of the active ingredient.

PDGF-C/PDGF-CC Detection/Diagnosis Assays

The anti-PDGF-C antibodies described herein may be used as the basic reagents in a number of different immunoassays to determine the presence of a PDGF-C and PDGF-CC form in a tissue sample and/or diagnose the presence of a PDGF-C expressing cell type, such as a PDGF-C expressing carcinoma, CNS tissue, blood, serum, plasma and cerebrospinal fluid. Generally speaking, the antibodies can be employed in any type of immunoassay, whether qualitative or quantitative. This includes both the two-site sandwich assay and the single site immunoassay of the non-competitive type, as well as in traditional competitive binding assays. One embodiment of interest, for ease of detection, and its quantitative nature, is the sandwich or double antibody assay, of which a number of variations exist, all of which are intended to be encompassed by this portion of the present invention. For example, in a typical forward sandwich assay, unlabeled antibody (e.g. a first anti-PDGF-C antibody) is immobilized on a solid substrate, e.g., microtiter plate wells, and the sample to be tested is brought into contact with the bound molecule. After a suitable period of incubation, for a period of time sufficient to allow formation of an antibody-antigen binary complex, a second antibody (e.g. a second PDGF-C antibody with a different target epitope than the first), labeled with a reporter molecule capable of inducing a detectable signal, is then added and incubation is continued allowing sufficient time for binding with the antigen at a different site and the formation of a ternary complex of antibody-antigen-labeled antibody. Any unreacted material is washed away, and the presence of the antigen is determined by observation of a signal, which may be quantitated by comparison with a control sample containing known amounts of antigen. Variations on the forward sandwich assay include the simultaneous assay, in which both sample and antibody are added simultaneously to the bound antibody, or a reverse sandwich assay in which the labeled antibody and sample to be tested are first combined, incubated and added to the unlabeled surface bound antibody. These techniques are well known to those skilled in the art, and the possibility of minor variations will be readily apparent. As used herein, "sandwich assay" is intended to encompass all variations on the basic two-site technique.

For the sandwich assays of the present invention, the assays can be conducted using two antibodies have different or same binding specificities for the PDGF-CC protein given its dimeric nature. Thus, a number of possible combinations are possible. As a more specific example, in a typical forward sandwich assay, a primary antibody is either covalently or passively bound to a solid support. The solid surface is usually glass or a polymer, the most commonly used polymers being cellulose, polyacrylamide, nylon, polystyrene, polyvinyl chloride or polypropylene. The solid supports may be in the form of tubes, beads, discs or microplates, or any other surfaces suitable for conducting an immunoassay. The binding processes are well known in the art. Following binding, the solid phase-antibody complex is washed in preparation for the test sample. An aliquot of the body fluid to be tested is then added to the solid phase complex and incubated at 25° C. for a period of time sufficient to allow binding of any PDGF-CC protein present to the antibody. The second antibody is then added to the solid phase complex and incubated at 25° C. for an additional period of time sufficient to allow the second antibody to bind to the primary antibody-antigen solid phase complex. The second antibody is linked to a reporter molecule, the visible signal of which is used to indicate the binding of the second antibody to any antigen in the sample. By "reporter molecule," as used in the present specification is meant a molecule which by its chemical nature, provides an analytically detectable signal which allows the detection of antigen-bound antibody. Detection must be at least relatively quantifiable, to allow determination of the amount of antigen in the sample, this may be calculated in absolute terms, or may be done in comparison with a standard (or series of standards) containing a known normal level of antigen.

The most commonly used reporter molecules in this type of assay are either enzymes or fluorophores. In the case of an enzyme immunoassay an enzyme is conjugated to the second antibody, often by means of glutaraldehyde or periodate. As will be readily recognized, however, a wide variety of different conjugation techniques exist, which are well known to the skilled artisan. Commonly used enzymes include horseradish peroxidase, glucose oxidase, beta-galactosidase and alkaline phosphatase, among others. The substrates to be used with the specific enzymes are generally chosen for the production, upon hydrolysis by the corresponding enzyme, of a detectable color change. For example, p-nitrophenyl phosphate is suitable for use with alkaline phosphatase conjugates; for peroxidase conjugates, 1,2-phenylenediamine or toluidine are commonly used. It is also possible to employ fluorogenic substrates, which yield a fluorescent product rather than the chromogenic substrates noted above. In all cases, the enzyme-labeled antibody is added to the first antibody-PDGF-CC protein complex and allowed to bind to the complex, and then the excess reagent is washed away. A solution containing the appropriate substrate is then added to the tertiary complex of antibody-antigen-labeled antibody. The substrate reacts with the enzyme linked to the second antibody, giving a qualitative visual signal, which may be further quantitated, usually spectrophotometrically, to give an evaluation of the amount of antigen that is present in the serum sample.

Additionally, fluorescent compounds, such as fluorescein or rhodamine, may be chemically coupled to antibodies without altering their binding capacity. When activated by illumination with light of a particular wavelength, the fluorochrome-labeled antibody absorbs the light energy, inducing a state of excitability in the molecule, followed by emission of the light at a characteristic longer wavelength. The emission appears as a characteristic color visually detectable with a light microscope or another suitable detection device. As in the enzyme immunoassay (EIA), the fluorescent-labeled antibody is allowed to bind to the first antibody-PDGF-C protein complex. After washing the unbound reagent, the remaining ternary complex is then exposed to light of the appropriate wavelength, and the fluorescence observed indicates the presence of the antigen. Immunofluorescence and EIA techniques are both very well established in the art and are particularly preferred for the present method. However, other reporter molecules, such as radioisotopes, chemiluminescent or bioluminescent molecules may also be employed. It will be readily apparent to the skilled artisan how to vary the procedure to suit the required use.

In another embodiment, the sample to be tested may be used in a single site immunoassay wherein it is adhered to a solid substrate either covalently or non-covalently. An unlabeled anti-PDGF-C antibody of the present invention is brought into contact with the sample bound on the solid substrate. After a suitable period of incubation, for a period of time sufficient to allow formation of an antibody-antigen binary complex a second antibody, labeled with a reporter molecule capable of inducing a detectable signal, is then added and incubation is continued allowing sufficient time for the formation of a ternary complex of antigen-antibody-labeled antibody. For the single site immunoassay, the second antibody may be a general antibody (i.e., zenogeneic antibody to immunoglobulin, particularly anti-(IgM and IgG) linked to a reporter molecule) that is capable of binding an antibody that is specific for PDGF-C/PDGF-CC.

Kits

The invention encompasses kits and diagnostic systems for conducting the above-described assays. To that end, one or more of the reaction components for the methods disclosed herein can be supplied in the form of a kit for use in the enrichment and detection of a target molecule. In such a kit, an appropriate amount of one or more reaction components is provided in one or more containers or held on a substrate (e.g., by electrostatic interactions, covalent bonding, or non-covalent bonding).

In one embodiment, a kit may comprise a target-specific antibody (e.g., anti-PDGF-C/PDGF-CC antibody), and one or more reagents for detecting binding of the target-specific antibody to the target. Reagents may include, for example, fluorescent tags, enzymatic tags, or other detectable tags. The reagents may also include secondary or tertiary antibodies or reagents for enzymatic reactions, wherein the enzymatic reactions produce a product that may be visualized. In one embodiment, the present invention provides a diagnostic kit comprising one or more target-specific antibodies of the present invention in labeled or unlabeled form in suitable container(s), reagents for the incubations for an indirect assay, and substrates or derivatizing agents for detection in such an assay, depending on the nature of the label. Control reagent(s) and instructions for use also may be included. The kit may also include one or more of the following components: supports, terminating, modifying or digestion reagents, osmolytes, an apparatus for detecting a detection tag, and buffers (in 1× or concentrated forms).

Diagnostic kits may also be supplied for use with a target-specific antibody, such as a labeled target-specific antibody, for the detection of the presence of the target in a tissue sample or host. In such diagnostic kits, as well as in kits for therapeutic uses described elsewhere herein, a target-specific antibody typically may be provided in a lyophilized form in a container, either alone or in conjunction with additional antibodies specific for a target cell or peptide. Typically, a pharmaceutically acceptable carrier (e.g., an inert diluent) and/or components thereof, such as a Tris, phosphate, or carbonate buffer, stabilizers, preservatives, biocides, inert proteins, e.g., serum albumin, or the like, also are included (typically in a separate container for mixing) and additional reagents (also typically in separate container(s)). In certain kits, a secondary antibody capable of binding to the target-specific antibody, which typically is present in a separate container, is also included. The second antibody is typically conjugated to a label and formulated in a manner similar to the target-specific antibody of the present invention. Using the methods described above and elsewhere herein, target-specific antibodies may be used to define subsets of patients in need of treatment and characterize such cells and related tissues.

A kit or system may contain, in an amount sufficient for at least one assay, any combination of the components described herein, and may further include instructions recorded in a tangible form for use of the components. In some applications, one or more reaction components may be provided in pre-measured single use amounts in individual, typically disposable, tubes or equivalent containers. With such an arrangement, the sample to be tested for the presence of a target antigen can be added to the individual tubes and amplification carried out directly. The amount of a component supplied in the kit can be any appropriate amount, and may depend on the target market to which the product is directed. General guidelines for determining appropriate amounts may be found in, for example, Joseph Sambrook and David W. Russell, Molecular Cloning: A Laboratory Manual, 3rd edition, Cold Spring Harbor Laboratory Press, 2001; and Frederick M. Ausubel, Current Protocols in Molecular Biology, John Wiley & Sons, 2003.

The container(s) in which the components are supplied can be any conventional container that is capable of holding the supplied form, for instance, microfuge tubes, ampoules, bottles, or integral testing devices, such as fluidic devices, cartridges, lateral flow, or other similar devices. In some embodiments, the kits can further include instructions to use the components in any of the methods described herein. Typical packaging materials for such kits and systems include solid matrices (e.g., glass, plastic, paper, foil, microparticles and the like) that hold the reaction components or detection probes in any of a variety of configurations (e.g., in a vial, microtiter plate well, microarray, and the like).

A system, in addition to containing kit components, may further include instrumentation for conducting an assay, e.g. a luminometer for detecting a signal from a labeled molecule. Instructions, such as written directions or videotaped demonstrations detailing the use of the kits or system of the present invention, are optionally provided with the kit or systems. Optionally, the kits or systems of the invention can further include software to expedite the generation, analysis and/or storage of data, and to facilitate access to databases. The software includes logical instructions, instructions sets, or suitable computer programs that can be used in the collection, storage and/or analysis of the data. Comparative and relational analysis of the data is possible using the software provided.

Drug Screening Assay

In further embodiments, the anti-PDGF antibodies of the present invention may be used in methods of screening for and selecting compounds that may act as an inhibitor of PDGF-CC activity in a cell. Such methodology comprises utilizing an antibody with anti-PDGF-C affinity in various antibody/peptide/test compound interaction assays in order to select a compound that modulates PDGF-CC activity. The compound may be a non-proteinaceous organic or inorganic molecule, a peptide (e.g., as a potential prophylactic or therapeutic peptide vaccine), a protein, DNA (single or double stranded) or RNA (such as siRNA or shRNA). It will become evident upon review of the disclosure and teachings of this specification that any such peptide or small molecule which effectively competes with an anti-PDGF-C antibody of the present invention for binding to the epitope of the PDGF-C, represents a possible lead compound relating to prophylactic or therapeutic treatment of a disease state characterized by PDGF-C expression or overexpression, particularly PDGF-C expressing carcinomas. To this end, interaction assays may be utilized for the purpose of high throughput screening to identify compounds that occupy or interact with the PDGF-C epitopes and displace the antibody.

Various antibody/antigen-based assays known in the art may be used in accordance with the foregoing, including, but not limited to, an ELISA assay, a radioimmune assay, a Western blot analysis, any homogenous assay relying on a detectable biological interaction not requiring separation or wash steps (e.g., see AlphaScreen from PerkinElmer) and/or SPR-based technology (e.g., see BIACore)). Compounds and/or peptide vaccine candidates identified through use of an anti-PDGF-C antibody may be detected by a variety of assays. The assay may be a simple "yes/no" assay to determine whether there is a change in the ability to form the known antibody/antigen complex, or may be made quantitative in nature by utilizing an assay such as an ELISA based assay, a homogenous assay, or an SPR-based assay. To this end, the present invention relates to any such assay, regardless of the known methodology employed, which measures the ability of a test compound to compete with an anti-PDGF-C antibody of the present invention.

The following are examples supporting the foregoing invention. They are not to be construed as limiting to the invention.

EXAMPLES

Example 1—Generation of Monoclonal Antibodies to Human PDGF-CC

Monoclonal antibodies were generated against human PDGF-CC active core domain protein. The purified PDGF-CC core domain fragment (RhPC) that was employed in the immunization protocol consisted of residues 230-345 (SEQ ID NO: 2) of the PDGF-CC protein (SEQ ID NO: 1) with a terminal histidine tag. It was produced and purified from baculovirus-infected insect Sf9 cells as previously described (Li X, et al. Nat Cell Biol. 2000 May 2(5):302-309, the contents of which are incorporated herein by reference). The core domain of PDGF-C has a 53% identity with a homologous region in PDGF-D (the human protein with which PDGF-C shares the most homology). There are sufficient areas of non-identity to generate an antibody specific to PDGF-CC.

Commercially available recombinant purified human PDGF-AA, PDGF-BB and PDGF-DD was purchased. Control polyclonal blocking antibodies to active PDGF-CC were affinity-purified rabbit IgG isolated from rabbit 615 as previously described (Li X, et al. Nat Cell Biol. 2000 May 2(5):302-309).

COS-1 cells were initially maintained in DMEM media. Both media were supplemented with 10% FCS, 2 mM glutamine, 100 U/ml penicillin and 100 mg/ml streptomycin. Cells were cultured at 37° C. in a humidified 5% CO2 atmosphere. Conditioned serum-free medium and precipitated proteins were collected with trichloroacetic acid. Growth factors PDGF-DD or PDGF-CC and penta Hispeptide were trichloroacetic acid (TCA)-precipitated and proteins separated by sodium dodecyl sulfate polyacrylamide gel electrophoresis (SDS-PAGE).

To produce the mouse PDGF-CC protein, COS-1 cells were transfected with mouse PDGF-C core plasmid constructed in expression vector pCDNA3.1 (Invitrogen). Transfection using lipofectamine plus reagent (Invitrogen) was performed according to the manufacturer's instructions. Transfected cells were cultured in serum free media. At 24 hours post-transfection, culture supernatant (COSmPCcoremedia) was collected and 30 µl sample was loaded on SDS-PAGE together with human PDGF-C core protein (0.1 µg RhPcc) and proteins separated by SDS-PAGE. Protein was then isolated using standard means.

Following immunisation of mice and splenic fusions by standard procedures, the supernatant of 16 hybridomas were initially assessed for PDGF-CC binding specificity by ELISA and Western analysis. A sensitive ELISA assay was employed to explore this using commercially available PDGF-AA, PDGF-BB, PDGF-DD and recombinant PDGF-CC. Specifically, antigen immobilization of purified recombinant human PDGF ligands, PDGF-AA, BB, CC and DD diluted in 100 mM NaHCO$_3$ at the concentration of 1 µg/ml, was performed overnight at +4° C. Thereafter, all incubations were done at room temperature 1.5-2 hours and washes carried out with PBS. In triplicate, hybridoma supernatants were applied at a dilution of 1:2 in PBS/1% bovine serum albumin (BSA), or purified monoclonal antibody (mAbs) was added (1.5 µg/ml in 3% BSA). A rabbit polyclonal IgG-purified antibody was used as positive control (4 µg/ml). Binding was detected with an anti-mouse (or anti-rabbit in control) alkaline phosphatase-conjugated secondary antibody and visualized by incubation with alkaline phosphatase yellow (pNPP) liquid substrate system for ELISA (Sigma-Aldrich). Absorbance was read at 405 nm.

Figure 2A:
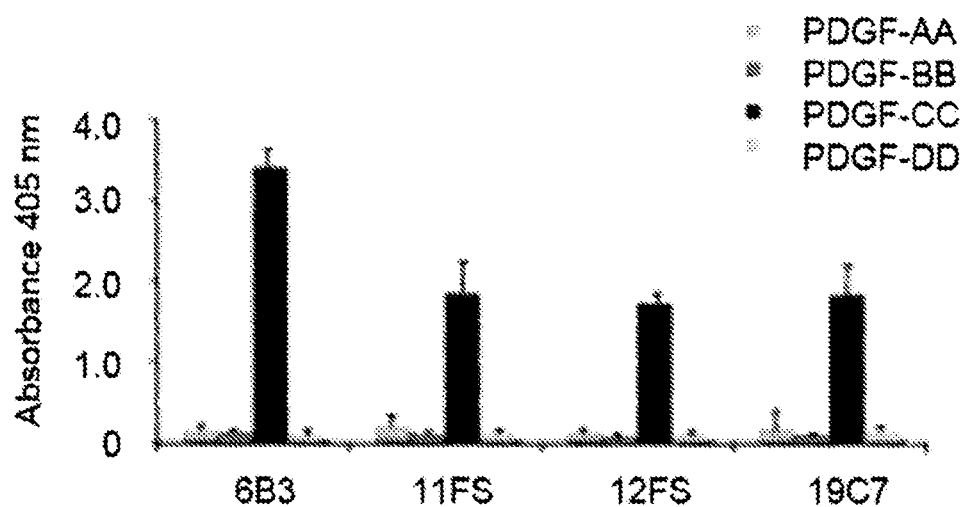
FIG. 2A illustrates that antibodies react only with human PDGF-CC and FIG. 2B illustrates 12F5 but not 6B3 recognize mouse PDGF-C core protein, both antibodies recognize RhPCc.
Figure 2B:
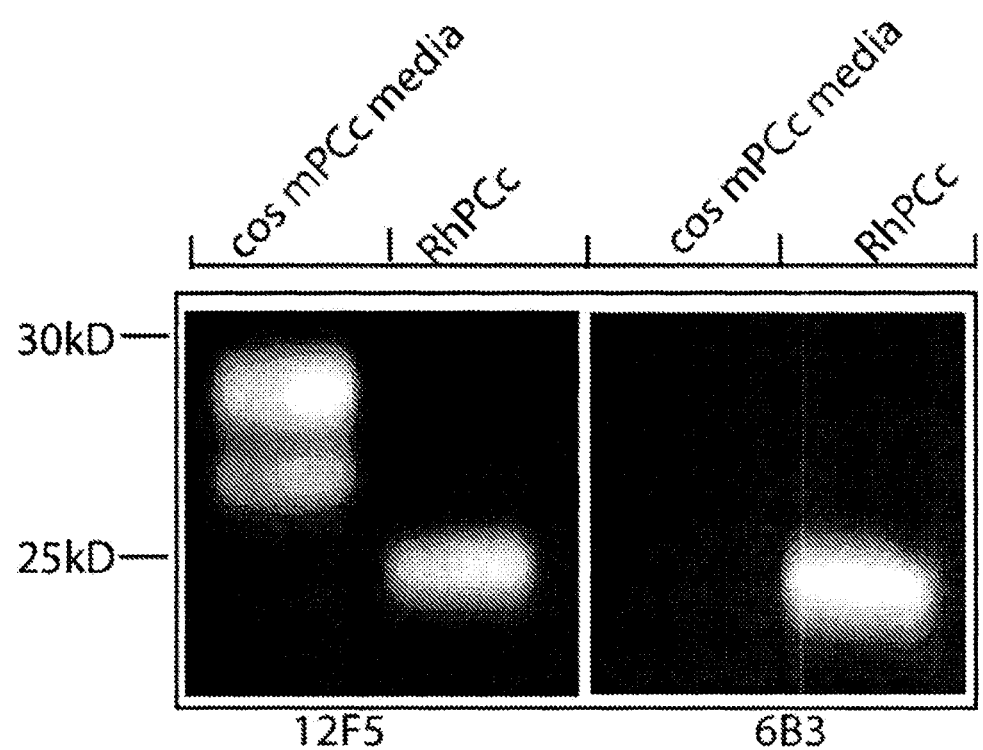
Figure 6:
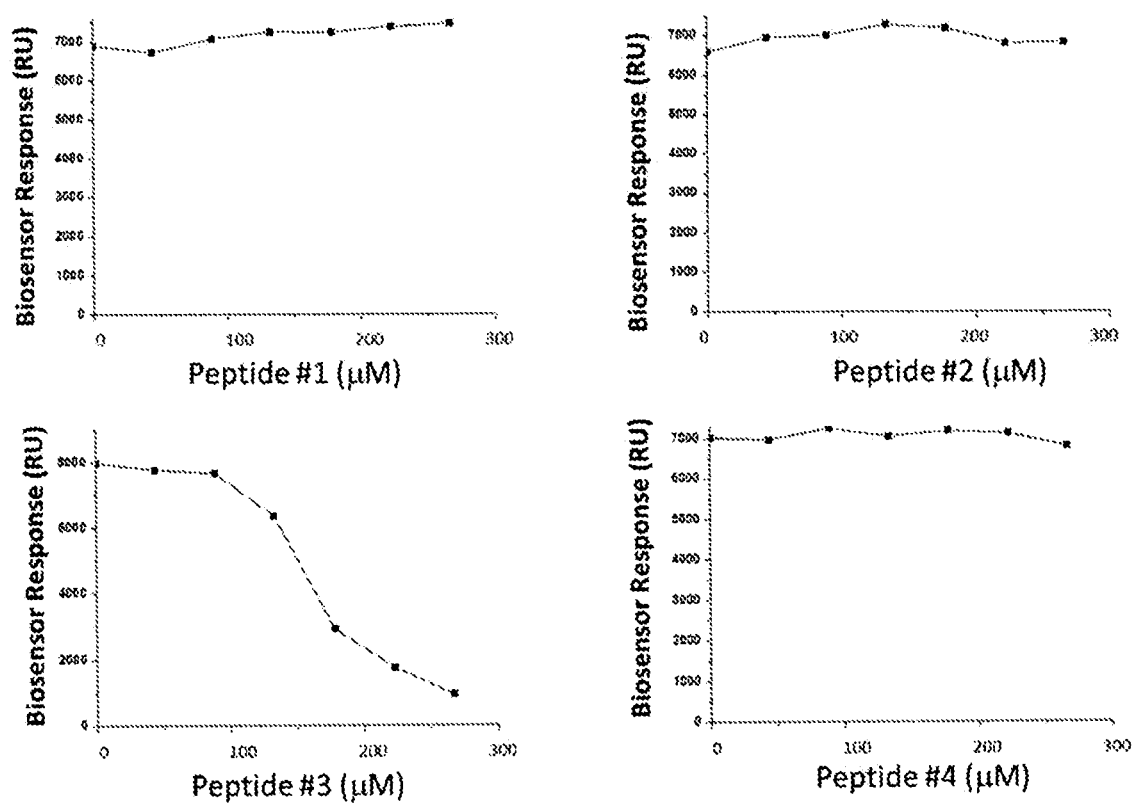
FIG. 6 illustrates biosensor analysis of maximum Biacore response observed for binding of 6B3 antibody (333 nM) to immobilized recombinant PDGF-CC core protein in the presence of varying concentrations (44.6-267.6 µM) of A) peptide 1 (DVALEHHEECDC, SEQ ID NO: 100); B) peptide 2 (LLTEEVR, SEQ ID NO: 101); C) peptide 3 (SVSIREELKRTDTIFWPGC, SEQ ID NO: 3) and D) peptide 4 (VTKKYHEVL, SEQ ID NO: 102). Decreased 6B3 binding to PDGF-CC was observed only in the presence of peptide 3 only, suggesting a specific inhibition.
Figure 7A:
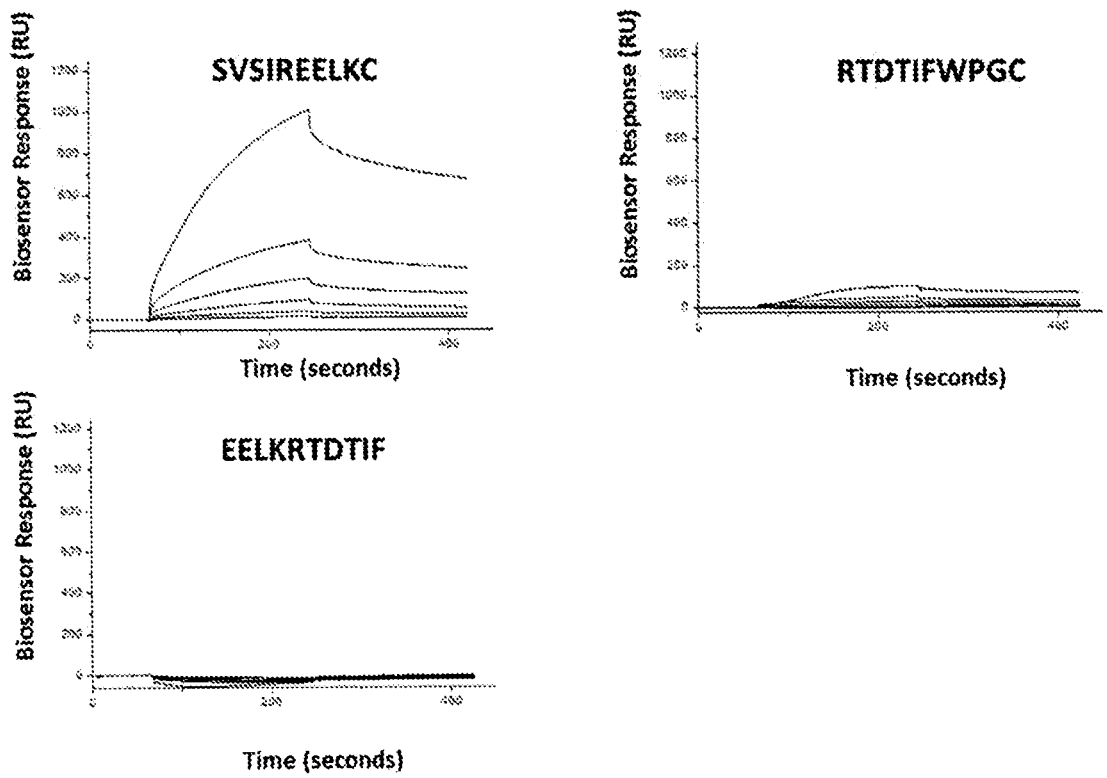
FIG. 7A illustrates sensorgrams from biosensor analysis of antibody 6B3 (concentration range 20.8 nM-667 nM) binding to immobilized PDGFC peptides (SVSIREELKC, RTDTIFWPGC and EELKRTDTIFC, SEQ ID NOs: 105-107) (FIG. 7A) and antibody 6B3 (1.334 µM) binding to immobilized PDGF-C peptide epitope SVSIREELKC (SEQ ID NO: 105) and the corresponding PDC F-D peptide SVNIREELKC, (SEQ ID NO: 108) that differs from the PDGF-C peptide by one amino acid (FIG. 7B). Peptides were synthesized with a C-terminal cysteine for defined orientation on the sensor chip using thiol immobilization.
Figure 7B:
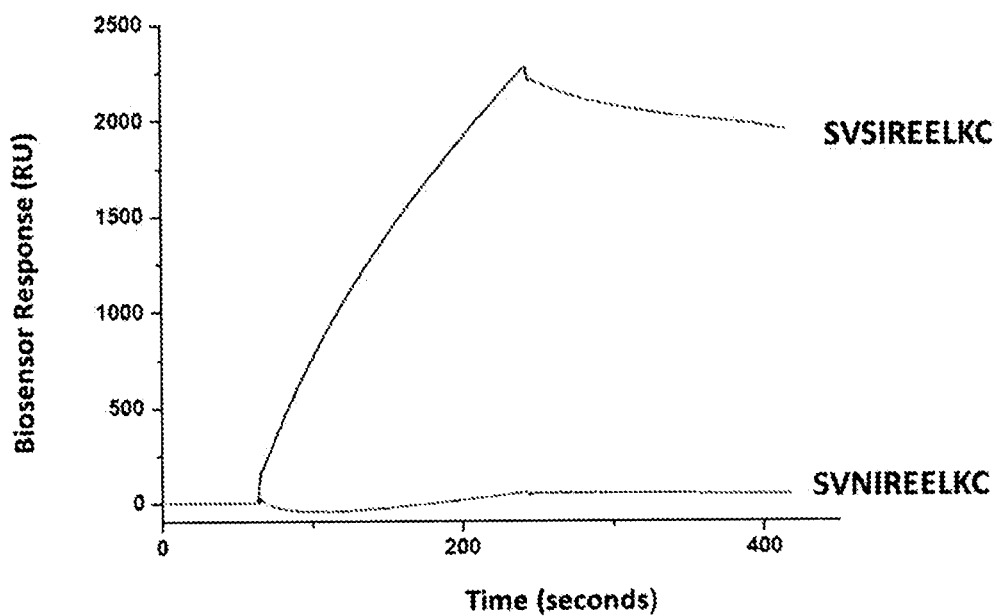
Figure 9:
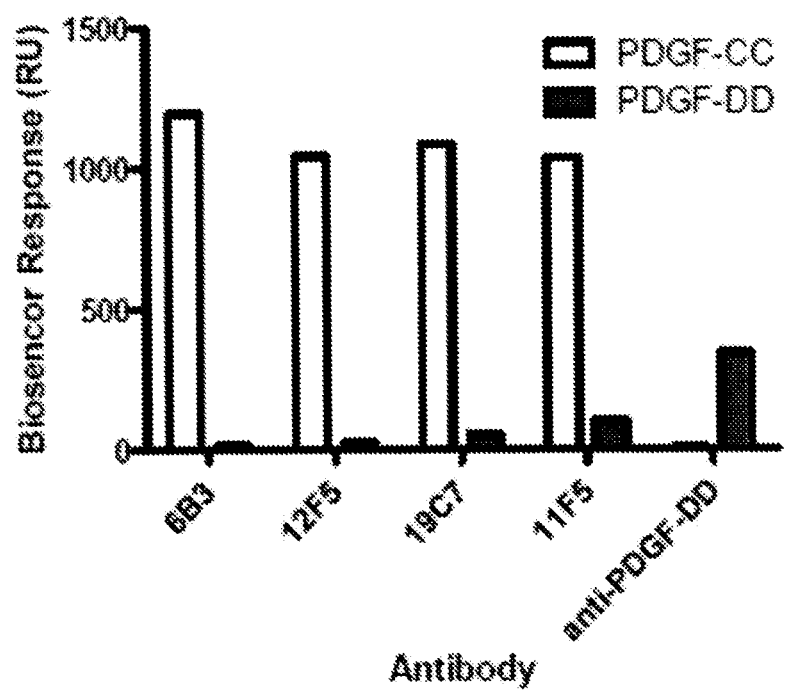
FIG. 9 provides graphic illustration of the biosensor analysis of the specificity of binding of the antibodies 6B3, 11F5, 12F5, and 19C7 to PDGF-CC and not PDGF-DD.
Figure 10:
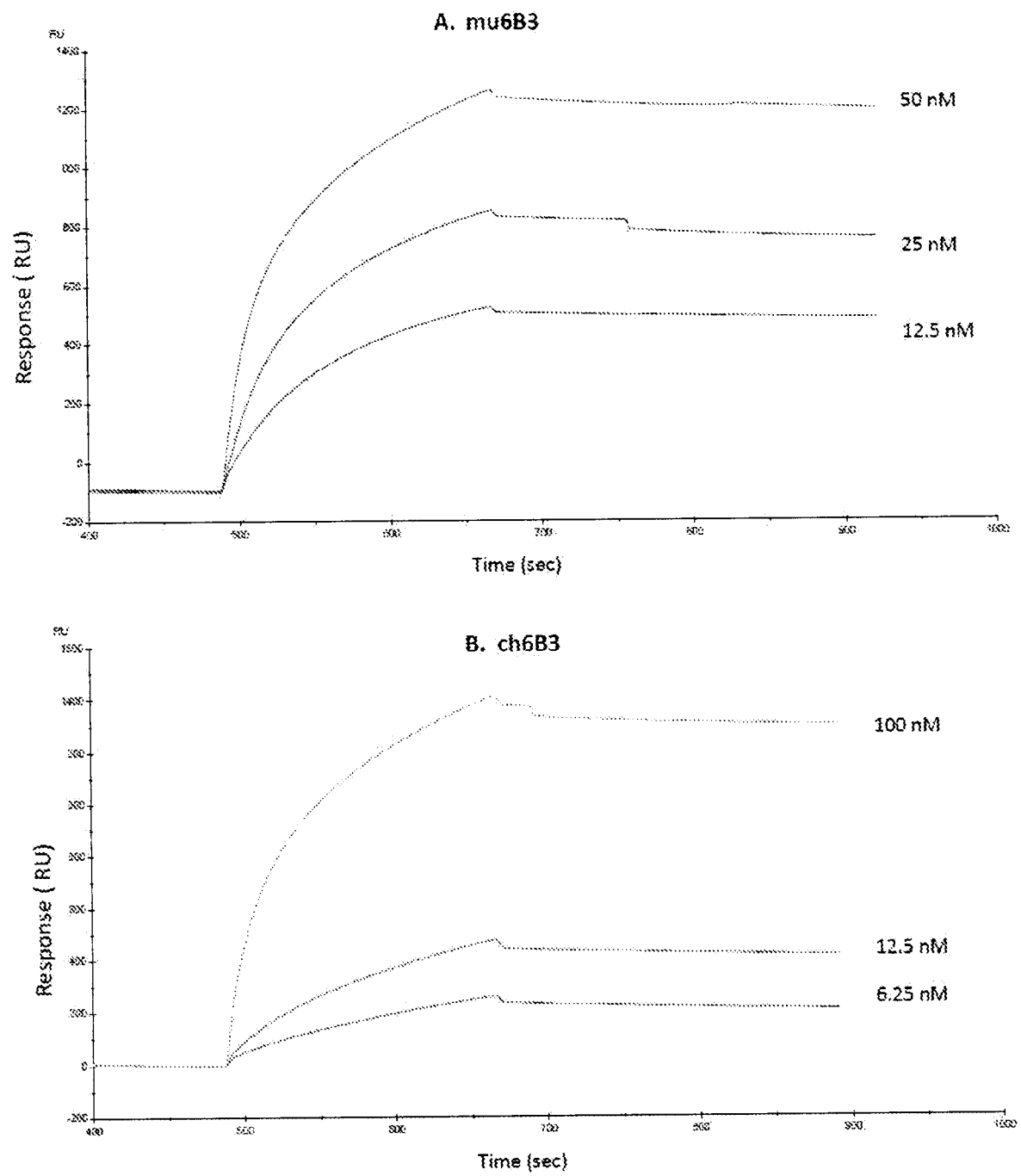
FIG. 10 illustrates representative binding curves for murine 6B3 (10A) and chimeric 6B3 (10B), which were fitted to a 1:1 Langmuir binding model.

Newly generated monoclonal antibodies showing the expected reactivity pattern and prevention of PDGFR-α phosphorylation were selected. Results of immunoblotting analysis showing binding of hybridomas supernatant specifically to PDGF-CC are shown in FIG. 1. There is a 53% amino acid identity between the core domain of PDGF-C and a homologous region in PDGF-D (the human protein with which PDGF-C shares the most homology). None of the clones showed strong positive immunoreactivity against PDGF-DD or poly-histidine (his6). A representative ELISA analysis with purified samples of antibodies 6B3, 11F5, 12F5 and 19C7 is shown in FIG. 2A. Antibodies 6B3, 11F5, 12F5 and 19C7 specifically bound human PDGF-CC but not PDGF-DD or PDGF-AA. Further immunoblotting analysis observed that purified antibody 12F5, but not 6B3, demonstrated binding to mouse PDGF-CC as well as human PDGF-CC (FIG. 2B). Antibody 6B3 demonstrated binding only to human PDGF-CC.

Example 2—Amino Acid Sequence of Antibodies

Figure 4:
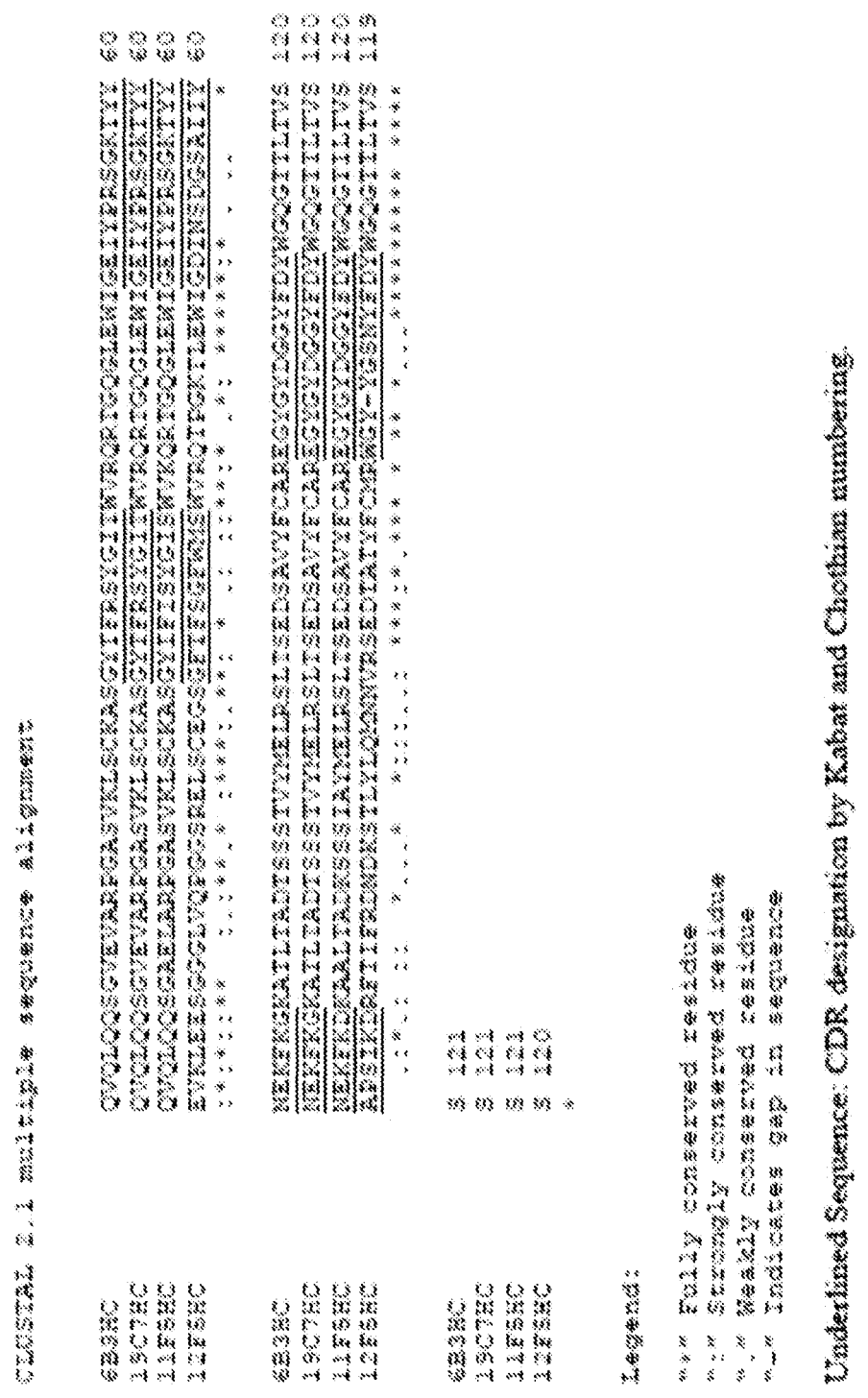

The amino acid sequence of the variable heavy and light chains for 6B3, 19C7, 11F5 and 12F5 was determined by standard procedures. Complete variable light chain and variable heavy chain sequences are presented in FIGS. 3 and 4, respectively. Interestingly, 19C7 and 6B3 sequences were identical. The antibodies were determined to all be isotype IgG2a with kappa light chain. The complementarity determining regions (CDRs) and isotypes of 6B3, 11F5 and 12F5 antibodies are presented in Tables 3 and 4 above and CDRs are the underlined sequences in FIGS. 3 and 4.

Example 3—Generation of Chimeric Anti-PDGF-CC Antibody 6B3 (ch6B3)

The cDNA sequences of murine monoclonal antibodies 11F5, 12F5, 19C7 and 6B3 were determined using standard laboratory techniques. Based upon in vitro and in vivo characteristics, below, 6B3 was selected as a candidate for the generation of a mouse-human chimeric antibody and for humanization.

Murine variable regions of the Heavy Chain (HC) and Light Chain (LC) clone 6B3 PDGF CC antibody were synthesized by GeneArt and cloned upstream of human IgG1 heavy and light chain kappa constant regions in pEE6.4 and pEE14.4 glutamine synthetase (GS) expression vectors (Lonza Biologics) respectively.

Following DNA sequence verification, the pEE6.4ch6B3HC and pEE14.4ch6B3LC vectors were digested with NotI/SalI restriction enzymes and the HC cassette from pEE6.4ch6B3HC was cloned into the pEE14.4ch6B3LC plasmid to make the double gene vector pDGVch6B3 final construct. Expression using the GS system in both transient (Freestyle 293) and stable (CHO) cells was conducted and the ch6B3 antibody product's PDGF-CC binding assessed using ELISA and Biacore and PDGF-CC neutralization activity were assessed in vitro as described below for the murine monoclonal antibodies.

The sequence alignment of chimeric (ch) and murine (mu) 6B3 antibodies is presented in FIG. 5. The complementarity determining regions (CDRs) and isotype of ch6B3, is presented in Tables 3 and 4 above and CDRs are the underlined sequences in FIG. 5.

Example 4—Identification of the 6B3 Binding Epitope on PDGF-C

The 6B3 antibody variable domains binding epitopes located on PDGF-CC core antigen were computationally predicted from 3D structures of the antibody Fv domains and a model of the PDGF-CC core domain dimer using the methods previously described (Zhang W., et. al. *J Comput Aided Mol Des.* 27(6):539-50, 2013).

Four putative peptides that formed part of the 6B3 antibody binding epitope on the PDGF-CC core protein were identified and then synthesized for Biosensor analyses aimed at refining the 6B3 binding epitope (Table 9).

TABLE 9

| | | |
|---|---|---|
| Peptide 1: | DVALEHHEECDC | SEQ ID No: 100 |
| Peptide 2: | LLTEEVR | SEQ ID No: 101 |
| Peptide 3: | SVSIREELKRTDTIFWPGC | SEQ ID No: 3 |
| Peptide 4: | VTKKYHEVL | SEQ ID No: 102 |

Binding of 6B3 Antibody to Immobilized PDGF-CC Core Domain and in the Absence and Presence of Potential Peptide Epitope:

Biosensor analyses were performed on a BIAcore 2000 biosensor using a carboxymethyldextran-coated sensor chip (Xantec CMD). The chip was derivatised on channel 2 with the PDGF-CC core antigen (60 µg/mL) using standard amine coupling chemistry (0.05M NHS/0.2M EDC). Channel 1 was derivatised with ethanolamine and used as a blank control channel for correction of refractive index effects.

Samples of 6B3 antibody (333 nM) was injected (304, at 10 µL/min) in HBS buffer (10 mM HEPES, pH 7.4; 150 mM NaCl, 3.4 mM EDTA, 0.005% Tween-20) over immobilized PDGFC antigen in the absence or presence of the individual PDGF-C peptides: peptide 1 (142 µM), peptide 2 116 µM, peptide 3 (89 µM) and peptide 4 (179 µM). After the injection phase, the dissociation was monitored by flowing HBS buffer over the chip surface for 360 s. Bound antibody was eluted and the chip surface regenerated between samples by injection of 30 µl of 10 mM Glycine pH 2.0

A change in 6B3 binding kinetics was observed in the presence of peptide 3 (SVSIREELKRTDTIFWPGC, SEQ ID NO: 3). Further biosensor analyses ascertained that this inhibition of 6B3 binding to PDGF-CC was peptide 3 concentration dependent indicating a specific inhibition. No 6B3 (333 nM) binding inhibition was observed with excess concentrations (up to 267 μM) of peptides 1, 2 or 4 (FIG. 6).

Binding of 6B3 Antibody to Immobilized PDGFC Peptide 3 (SVSIREELKRTDTIFWPGC, SEQ ID NO: 3):

Peptide 3 was immobilized on channel 4 of the carboxymethyldextran-coated sensor chip using thiol chemistry. Briefly, the chip was activated on channel 4 using standard amine coupling chemistry (0.05M NHS/0.2M EDC) followed by 80 mM (2-(2-pyridinyldithio)ethane amine (PDEA) in 1M borate PH 8.2. Peptide 3 (100 nM in 10 mM sodium acetate pH 4.5) was conjugated via its C-terminal cysteine to PDEA. The chip was then blocked using 40 mM L-cysteine in 10 mM sodium acetate pH 4.0 and 1 M ethanolamine pH 8.2. A blank derivatised channel was used as the control channel.

Samples of antibody 6B3 (20.8 nM-667 nM) were injected (304, at 10 μL/min) in HBS buffer over immobilized peptide 3. Specific binding was observed as compared to the blank channel and then investigated further with smaller overlapping peptide sequences (data not shown).

Determination of Specific PDGFC Peptide Sequence Bound by Antibody 6B3:

Three overlapping 10 amino acid peptides, encompassing the putative epitope region of SVSIREELKRTDTIFWPGC (SEQ ID NO: 3) within the PDGFC core domain were synthesized to further reline the 6B3 epitope. These peptides were: SVSIREELKC, RTDTIFWPGC and EELKRTDTIFC (SEQ ID NOs: 105-107). The peptides were synthesised with a C-terminal cysteine for defined orientation on the sensor chip using thiol immobilisation.

Samples of 6B3 antibody (1.334 μM) was injected (304, at 10 μL/min) in HBS buffer over the immobilized peptides. The results are shown in FIG. 7A and indicate 6B3 binds to the SVSIREELKC (SEQ ID NO: 105) peptide and that the SVSIR sequence is essential for 6B3 binding as no binding was observed to overlapping peptide EELKRTDTIFC (SEQ ID NO: 107), or to alternate peptide SVNIREELKC (SEQ ID NO: 108) as shown in FIG. 7B.

Accordingly the prediction of putative 6B3 epitopes by homology modeling and subsequent determination by biosensor analyses determined that the specific 6B3 epitope within the PDGFC core domain sequence is $_{256}$SVSIR$_{260}$ within the sequence SVSIREELKRTDTIFWPGC (SEQ ID NO: 3).

PDGFC Specificity of Antibody 6B3 Epitope:

As our prior Western blot and cell based analyses had determined that 6B3 does not bind PDGF-D polypeptide, further biosensor binding analyses examined the binding of 6B3 to the PDGF-C peptide epitope SVSIREELKC (SEQ ID NO: 105) and the corresponding PDGF-D peptide SVNIREELKC (SEQ ID NO: 108) that differs by one amino acid. The peptides were synthesised with a C-terminal cysteine for defined orientation on the sensor chip using thiol immobilisation.

Samples of antibody 6B3 (667 nM) was injected (304, at 10 μL/min) in HBS buffer over immobilized SVSIREELKC (SEQ ID NO: 105) and SVNIREELKC (SEQ ID NO: 108) peptides. Specific binding to SVSIREELKC (PDGFC epitope peptide, SEQ ID NO: 105) was observed as compared to SVNIREELKC (corresponding PDGFD epitope peptide, SEQ ID NO: 108) and to the blank control channel (FIG. 7B).

The PDGF-C sequence SVSIR differs by only one amino acid (serine) from the corresponding PDGF-D sequence (FIG. 8).

Example 5—Biosensor Confirmation of Human PDGF-CC Specificity

A. Affinity Estimation

Biosensor analyses were performed on a BIAcore 2000 biosensor using an NTA sensor chip. Briefly, a NTA sensor chip was loaded with Ni 2+ and used to immobilize histidine tagged PDGF-CC ligand. The PDGF-CC antibodies were passed over the chip at varying concentrations in order to determine apparent affinity ($K_D$). Chips were regenerated with EGTA. The chip was re-equilibrated by washing with HBS (containing no EDTA) before further analyses. Using BIAevaluation software, a 1:1 Langmuir binding analysis model was used to estimate the apparent association (ka) and disassociation (kd) rate constants for each set of antibody experiments.

Anti-PDGF-CC mAbs (6B3, 12F5, 19C7 and 11F5) at a concentration of 330 nM were injected over immobilized PDGF-CC and PDGF-DD (R&D). Results shown in FIG. 9 demonstrate specificity of binding to PDGF-CC compared to the closely related sequence of PDGF-DD, and these observations were in agreement with ELISA analyses (FIG. 2A). The chimeric 6B3 construct also demonstrated low nanomolar apparent binding affinity and no loss of apparent binding affinity, as compared to the 6B3 murine antibody. Representative binding curves for murine and chimeric 6B3 are shown in FIG. 10. These curves were fitted to a 1:1 Langmuir binding model.

Dose dependent binding was observed for each of the antibodies examined. The apparent on-rate ($k_a$), off-rate ($k_d$) and dissociation constants are reported in Table 10. The calculated dissociation constants for each antibody were in the low nanomolar range, indicating that all five antibodies had a high affinity for the PDGF-CC ligand. As expected, 6B3 and 19C7 demonstrated highly comparable apparent binding affinities.

TABLE 10

Biosensor analysis. Apparent binding parameters anti-PDGF-CC antibodies determined using 1/1 Langmuir analysis

| Antibody | $k_a \times 10^{-5}$ $(M^{-1}s^{-1})$ | $k_d \times 10^4$ $(s^{-1})$ | $K_D$ $(M^{-1})$ |
|---|---|---|---|
| 6B3 | 18 | 15 | $0.9 \times 10^9$ |
| 19C7 | 22 | 16 | $0.7 \times 10^9$ |
| 11F5 | 6.4 | 5.8 | $1.05 \times 10^9$ |
| 12F5 | 0.9 | 2.0 | $2.2 \times 10^9$ |
| ch6B3 | 6.0 | 4.1 | $0.7 \times 10^9$ |

B. Specificity of Binding

Competitive binding analyses were similarly conducted for the panel of 4 anti-PDGF-CC candidate mAbs using immobilized PDGF-CC. The PDGF-CC antigen was covalently coupled to a CM5 Sensor Chip via primary amine groups (NHS/EDC chemistry) using standard conditions. Anti-PDGF-CC mAbs (6B3, 12F5, 19C7 and 11F5) and a control anti-PDGF-DD mAbs were injected over immobilized antigens. Monoclonal antibodies directed against separate epitopes will bind independently of each other, whereas antibodies directed against closely related epitopes will interfere with each other's binding. Pairwise binding studies were performed by injection of the first antibody (504, at 100 µl/mL) until surface saturation where all the available binding sites were occupied. Binding of the second antibody to PDGF-CC was then assessed following injection (504, at 100 µl/mL).

Each analysis cycle was terminated by removing bound material from the sensor chip surface using 10 mM Glycine pH 2.1. Mapping was performed by analyzing reciprocal duplicates of the same antibodies in reversed order. To further examine the nature of the binding to PDGF-CC and the potential for involvement of disulfide bonds within PDGF-CC, monoclonal antibody binding was performed using non-reduced and reduced/alkylated antigen. Reduction and alkylation were performed on immobilized PDGF-CC by successive injection of dithiothreitol (200 µL, at 50 mM) and iodoacetamide (30 mM at 200 µL).

The effectiveness of the mAbs to cross compete for binding to immobilized PDGF-CC ligand is tabulated below (Table 11). The code comprises: Empty, Binding antibodies (Different epitopes); X: Competing antibodies (Similar epitope); O, Antibodies that interfere with binding.

TABLE 11

Biosensor Analysis-antibody cross competition for binding immobilized PDGF-CC

|  | 6B3 | 19C7 | 12F5 | 11F5 |
|---|---|---|---|---|
| 6B3 | X | X | | |
| 19C7 | X | X | | |
| 12F5 | | | X | |
| 11F5 | O | O | | X |

As expected each antibody competed with itself, and the identical variable domain mAbs 6B3 and 19C7 also competed for binding. MAbs 12F5 and 11F5 have different epitopes to 6B3 and 19C7 and to each other. Some interference of binding was observed for 11F5 with 6B3 and 19C7, suggesting an overlap of epitope or steric hindrance.

The epitope groups for the 4 antibodies as determined from the Biacore data is presented diagrammatically below.

Epitope groups determined from Biacore data

No apparent change of binding reactivity was observed when PDGF-CC antigen was reduced and alkylated suggesting that all epitopes appeared to be disulfide independent.

Example 6—PDGF-Ligand Induced Receptor Activation and Cell Proliferation

Porcine aortic endothelial cells (PAE) over-expressing PDGF receptor α (PDGFR-α) were utilized to characterize the mAbs for neutralizing activity of PDGF-CC-induced PDGFR-α activation. The cells were stimulated for 1 hour on ice with 60 ng/ml activated recombinant human PDGF-ligand only, or with PDGF-ligand pre-incubated with the purified mAbs (5 µg/ml). Positive control for PDGF-BB activation of PDGFR-α and negative control of full length PDGF-CC (Control) or unstimulated cells were included in the assay. Cells were thereafter washed in cold PBS, mildly centrifuged and lysed in lysis buffer (20 mM Tris-HCl pH 7.5, 150 mM NaCl, 5 mM EDTA, 0.5% deoxycholic acid, 200 µM orthovanadate and complete protease inhibitor). Released proteins were then analyzed by immunoblotting using a mouse monoclonal antibody recognizing phosphotyrosine PY99 and a rabbit polyclonal antibody detecting C-terminal PDGFR, CED used as loading control.

Figure 11A:
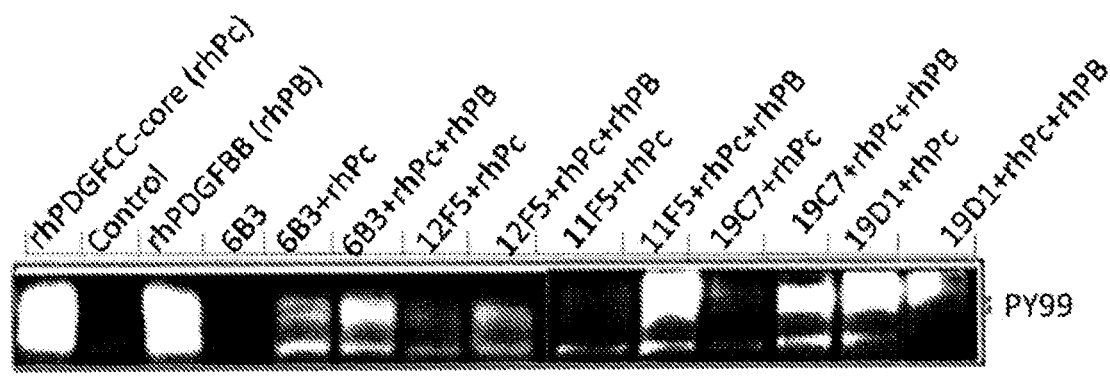
FIG. 11 illustrates inhibition of PDGF-CC activity, with FIG. 11A providing SDS-PAGE gel and immunoblotting analysis showing inhibition of PAE-PDGFRα phosphorylation and FIG. 11B providing an SDS-PAGE gel and immunoblotting analysis showing inhibition of PDGF-CC induced PAE-PDGFR alpha phosphorylation. PB: Positive Control for PDGF-BB activation of PDGFR alpha; Control: negative control of full length PDGF-C. RhPC: recombinant human PDGF-CC core domain.
Figure 11B:
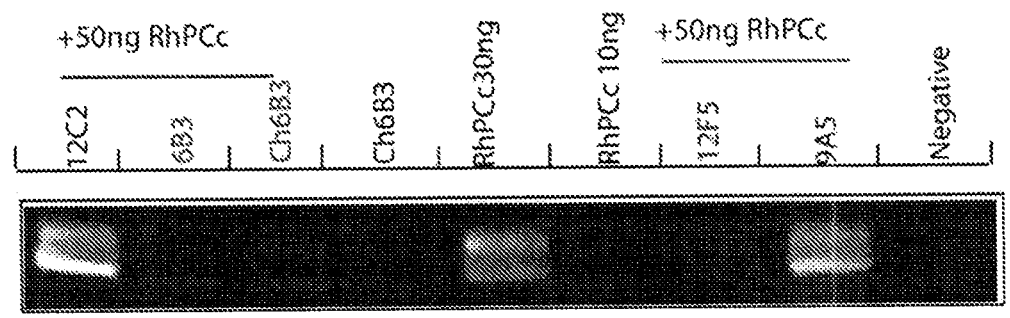

The core domain of human PDGF-CC efficiently induced tyrosine phosphorylation of PDGFR-α, as did PDGF-BB (FIG. 11A). PDGFR-α from unstimulated cells or from cells stimulated with full-length PDGF-CC showed only background levels of activation. Subsequent probing of the filters with antibodies against PDGFR-α confirmed that equal amounts of PDGFR-α were present in all lanes (data not shown). It was observed that antibodies 6B3, 11F5, 19C7 and 12F5 blocked PDGF-CC-induced, but not PDGF-BB induced phosphorylation of PDGFR-α in PAE cells. Thus these antibodies are neutralizing monoclonal antibodies to human PDGF-CC. In vitro analyses also demonstrated that mouse-human chimeric antibody 6B3 is a neutralizing antibody as effective as parental murine mAb 6B3 in inhibiting PDGF-CC induced PDGFR-α activation (FIG. 11B). Anti-PDGF-CC mAb 12F5, but not 12C2 or 9A5, was also neutralizing.

Figure 12A:
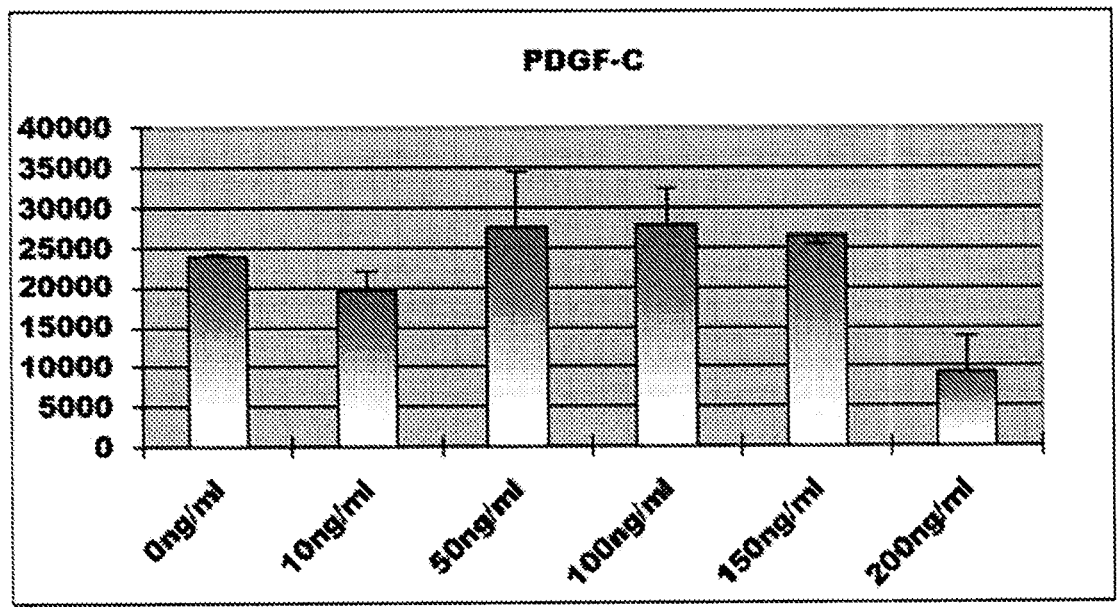
FIGS. 12A and B demonstrate that 6B3 inhibits PDGF-CC induced PAEα cells proliferation in a dosage dependent manner.

PAE (porcine aortic endothelial cells) over-expressing PDGFR-α were similarly utilized to assess 6B3 as an example of these antibodies for ability to inhibit proliferation by PDGF-CC-induced PDGFR-α activation. PAE-α cells were seeded in 6-well plates ($2 \times 10^5$ cells/well), and starved in serum-free media overnight. The cells were then either treated with human PDGF-CC core-domain protein (RhPCC) (FIG. 12A), or with 6B3 (0-6 µg/ml) and 50 ng/ml RhPCC (FIG. 12B) for 24 hours. The cell numbers were determined after 24 hours with a cell counter.

Figure 12B:
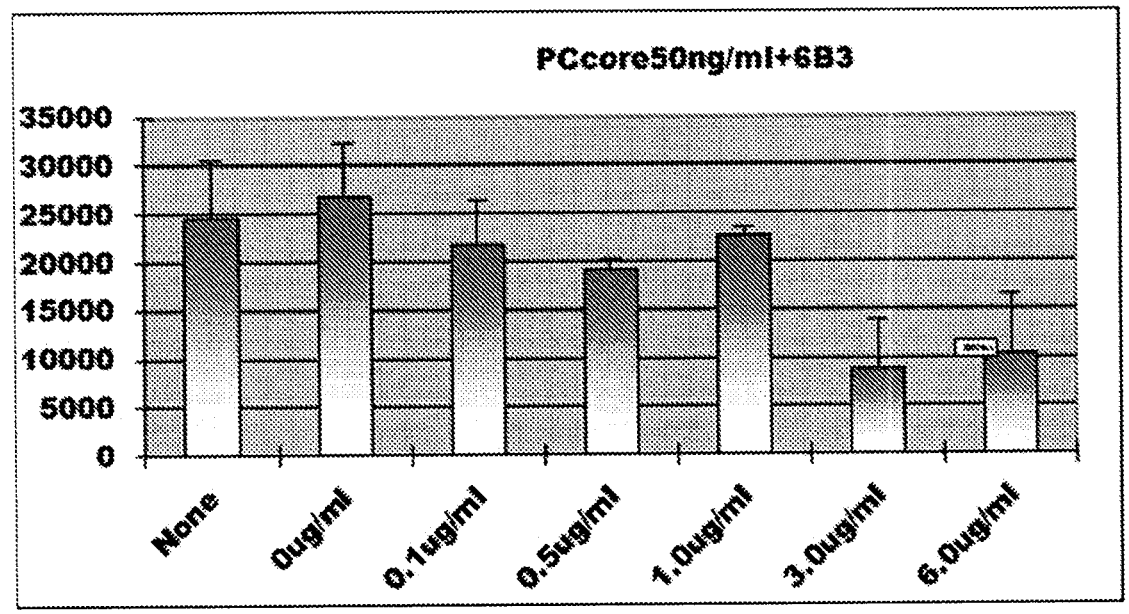

FIG. 12 demonstrates that 6B3 inhibits PDGF-CC induced PAEα cells proliferation in a dosage dependent manner. In the presence of 3 µg/ml 6B3 maximal inhibition of PAEα cell proliferation induced by 50 ng/ml PDGF-CC core domain was observed (FIG. 12B).

Example 7—Immunohistochemistry—Tissue Screens

A. Materials and Methods

The immunohistochemical analysis of 6B3, 11F5, 12F5 and 19C7 and other clones reactivity were initially explored on breast cancer tissue. Further immunohistochemical characterization of clone 6B3 as an example of these antibodies was conducted on a panel of formalin fixed, paraffin embedded human normal tissues and tumor.

Human tissues were provided by the Victorian Cancer Biobank and Austin Hospital Tissue Bank (Melbourne, Australia). Paraffin-embedded sections were deparaffinized followed by quenching of endogenous peroxidase activity with 3% hydrogen peroxide for 10 min at room temperature. Antigen retrieval was by boiling in 10 mmol/L citric acid pH 6.0 for 30 min. Antibodies and dilutions used were, or 6B3 (1.5 μg/ml), isotype control mIgG1 (Southern Biotechnologies; 1.5 μg/ml,) CD34 (0.5 μg/mL; Dako). Antibody binding was detected using Dako-Envision+ anti-mouse-HRP conjugated secondary antibody followed by DAB chromogen.

Positive control sample consisted of the human lung carcinoma cell line A549 (ATCC) and a known positive squamous cell lung carcinoma tissue. Assay controls comprised replacing the primary antibody with an isotype control, or omission of the primary antibody.

Test tissue was reported positive if a signal was present in the tissue incubated with antibody and there was an absence of signal in sections incubated with the isotype control and/or sections incubated in the absence of primary antibody.

A further analysis of the specificity of staining with the positive control tissues involved competition with the PDGF-CC ligand or the related growth factor VEGF-B. Murine 6B3 antibody (1.5 μg/ml) was incubated with 6.7× excess of PDGF-CC His$_6$ antigen (10 μg/ml) or an excess of VEGF-B antigen (10 μg/ml) one hour prior to application of mixture to a section of A549 cells or human placental tissue. Detection of the staining was carried out as per the standard 6B3 immunohistochemistry protocol.

Slides were digitized using an Aperio ScanScope XT instrument (Aperio Technologies, Inc, Vista, Calif.) and viewed using ImageScope software (Aperio Technologies, Inc, Vista, Calif.).

Test tissue was reported positive if a signal was present in the tissue incubated with antibody and there was no or minimal signal in sections incubated with the isotype control or sections incubated without primary antibody.

The antibody CD34 was applied to adjacent sections to assist with the identification and staining frequency of blood vessels.

The 6B3 staining was reported by three parameters:
1) Intensity of positive staining: − or neg or −ve negative; +, weak staining; ++, moderate staining; +++, intense staining; and +ve, positive staining where intensity not recorded
2) Percentage of positive cell staining, which was provided as a range:
   Neg,
   <5%
   6-25%
   26-50%
   51-75%
   >75%
3) Frequency of positive tissues i.e. positive tissues (numerator) compared to total number of tissues evaluated (denominator).

A modified H-score was determined for each individual tissue sample based on the intensity of the stain and the percentage of positively stained cells. This score was determined by multiplying the fraction of positive cells (range 0-5 [neg=0; <5%=1; 6-25%=2; 26-50%=3; 51-75%=4; >75%=5]) by the intensity of staining (neg=0; +=1; ++=2; +++=3). Using the modified H-score t-tests were conducted was used for each tissue type to determine statistical significance between 6B3 reactivity in Normal and Tumor specimens. A P value <0.05 was significant.

B. Results

The results of immunohistochemical staining of normal and tumor tissues are shown in Tables 12 and 13, respectively. The isotype and negative controls were devoid of staining, indicating that staining with the 6B3 antibody was specific. Representative images of normal tissue and tumor tissue staining patterns are presented in FIGS. 13 and 14, respectively.

i. Normal Tissues

Northern blot analysis has previously revealed abundant expression of PDGF-C transcripts in human heart, liver, kidney, pancreas and ovary, smaller levels of mRNA transcripts in most other tissues. In agreement with this prior mRNA analysis, widespread expression of PDGF-CC protein was observed in human heart, liver, kidney, pancreas, uterus, ovary and prostate.

Figure 13:
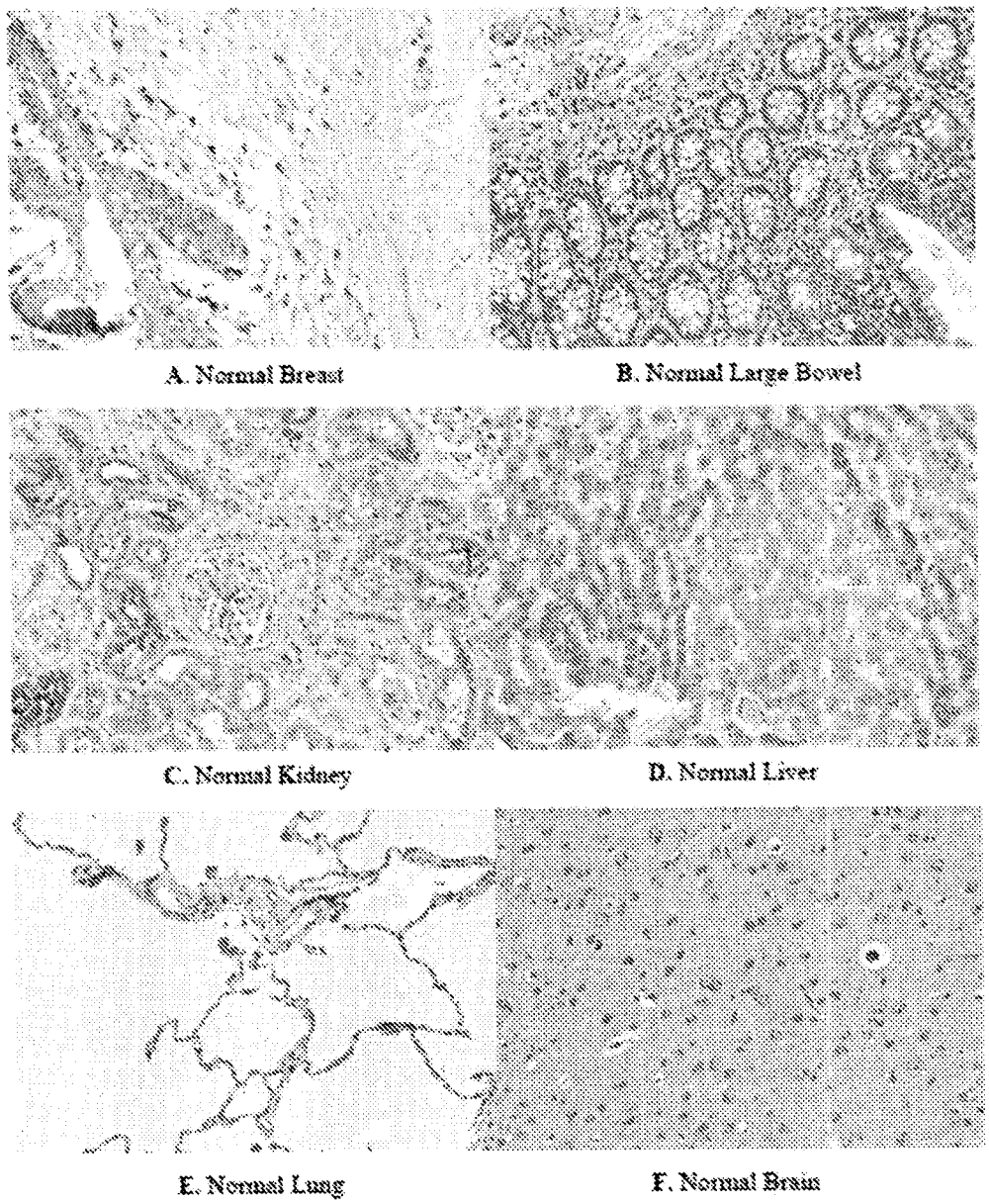
FIG. 13A-F illustrates the immunohistochemical 6B3 staining pattern in normal human tissues, magnified at 200×.

In normal tissues, the staining pattern for 6B3 was mainly observed in the cytoplasm of the epithelial cells, and where noted the cytoplasm of stromal cells, the exception being ovary, where a membranous pattern is also seen. Staining of endothelial cells was also observed (FIG. 13). The frequency of staining of vessels and stroma tended to be less than the staining frequency of the epithelial components of the normal tissues, with the exceptions of bowel, ovary, uterus and placenta where the stromal and vascular staining showed a similar frequency of positive staining.

The adrenal cortical cells exhibited weak to moderate cytoplasmic staining. Only the cortical immunohistochemical staining of the adrenal gland was able to be reported as no medulla was sampled in the tissue cores. Widespread weak to moderate neuronal and glial cell staining was observed in the brain. The predominant pattern of staining in breast tissue was to the myoepithelial cells, however, the ductal cells were also positively stained. Fat showed weak positivity (data not shown). In kidney, there was widespread staining of the epithelial cells of the tubules and staining of the parietal cells in the glomeruli. High kidney PDGF-CC mRNA levels and staining of the parietal epithelial cells of Bowman's capsule, tubular epithelial cells (loops of Henle, distal tubules, collecting ducts), and in arterial endothelial cells has also been previously described using a polyclonal antibody. In large bowel, the glands and epithelium generally showed a weak to moderate intensity of staining, however, the lamina propria exhibited an increased staining intensity. Weak staining of the heart myocardium and low frequency of positively staining vessels was observed suggesting that although high levels of mRNA for the latent growth factor were previously reported for human heart, active PDGF-CC is not normally present. Moderate to strong staining intensity was observed for liver hepatocytes in agreement with prior mRNA analysis, however, the bile ducts, whilst mostly positive, had a weaker intensity. A similar pattern was observed in normal pancreas where the acini exhibited a widespread staining pattern with moderate to strong intensity, however the ducts stained weakly and less frequently.

ii. Tumor Tissues

Immunostaining of PDGF-CC protein was observed in the cytoplasm and membrane of tumor cells, often showing a strong peri-nuclear staining pattern. Expression of 6B3 was also seen in endothelial cells of the blood vessels and wherever evaluable, the cytoplasm of stromal components of the tumors examined.

Figure 14:
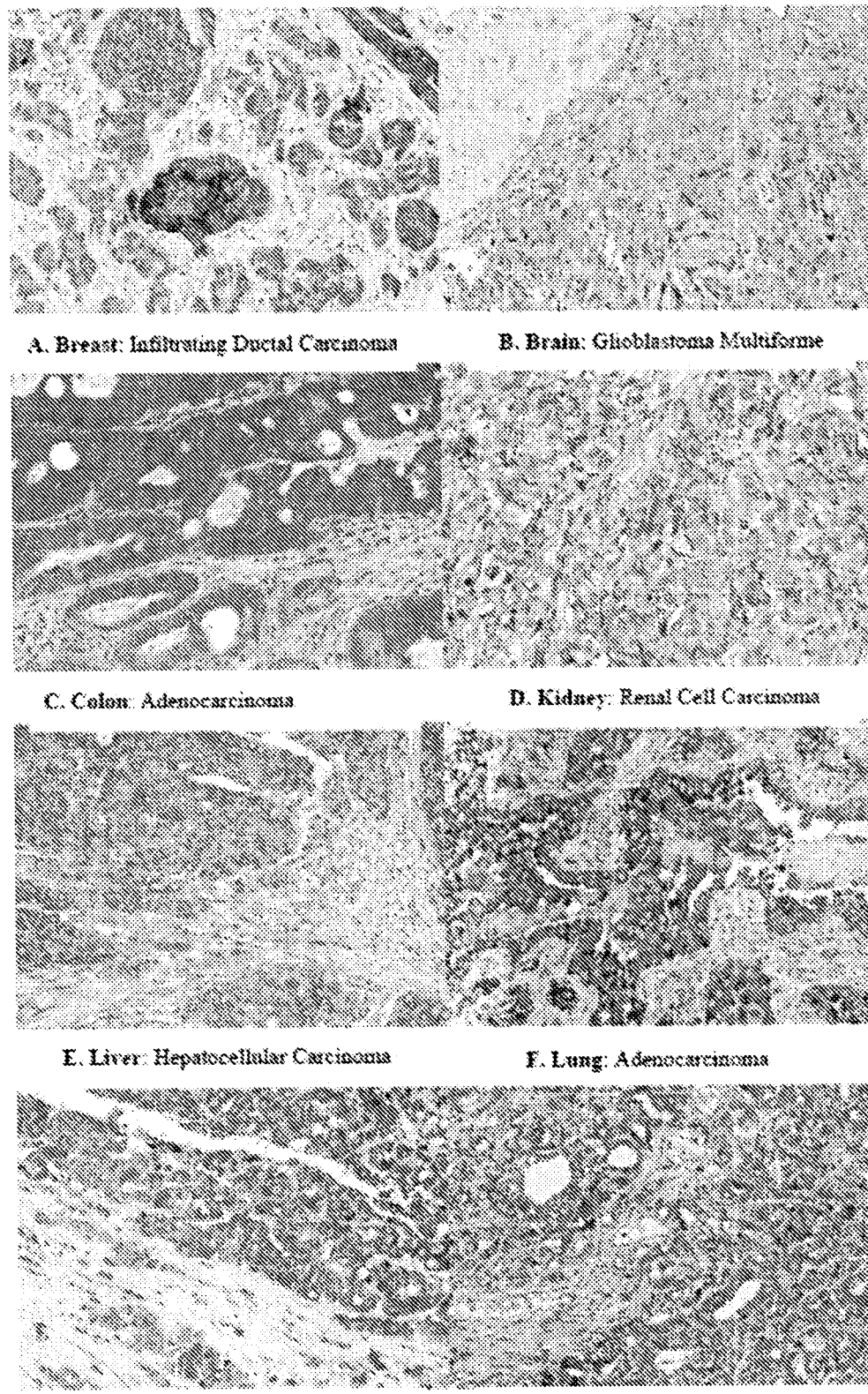
FIG. 14A-H illustrates the immunohistochemical 6B3 staining pattern in human tumor tissues, magnified at 200×.

The tumor cell staining was widespread for all the tumor tissues studied, where generally greater than 75% of the tumor cells expressed a moderate to strong intensity of staining, with the exceptions of glioblastomas, infiltrating lobular carcinomas and prostate adenocarcinomas, where a more heterogenous staining pattern was seen (FIG. 14). Furthermore, there were no differences between the frequency nor intensity of staining across different grades of tumor differentiation.

iii. Comparison Between Tumor and Normal Tissues

Generally, normal tissue parenchyma showed a markedly decreased intensity of staining when compared to the respective tumor cell staining intensity. The exceptions to this were liver tissue where the difference in intensity between normal hepatocytes and the primary liver tumor cells, and uterine tissue where the difference in staining intensity between normal glandular epithelium and uterine tumor cells were not obvious.

Furthermore, the frequency of positively stained cells was lower for normal tissues when compared the tumor tissues. The exceptions to this are again liver and uterine tissue and in addition, kidney, ovary and brain where no obvious differences were evident.

Collectively, the results indicated lower PDGF-CC expression in normal tissues compared to their respective tumor tissues, with some exceptions.

In order to explore the apparent differences between normal and tumor 6B3 staining patterns, a modified H-Score system was utilized to enable statistical analyses of results where the percentage of positive cell staining was reported as a range rather than a discrete number.

Based on an analysis of the modified H-Scores, the 6B3 staining of PDGF-CC in tumor cells was significantly increased compared to their respective normal epithelial tissues of bladder ($P=0.039$), brain gliosarcoma ($P<0.001$), breast infiltrating ductal carcinoma ($P=0.006$), bowel ($P<0.001$), kidney ($P=0.008$), pancreas ($P<0.001$) and prostate ($P=0.001$). However, there was no significant difference between tumor cell staining and their respective normal epithelium for brain glioblastomas ($P=0.26$), and breast infiltrating lobular carcinomas ($P=0.87$) which both displayed a very heterogenous staining pattern, nor for hepatocellular carcinoma ($P=0.26$) and uterine adenocarcinoma ($P=0.59$) where PDGF-C staining was also strongly positive in their respective normal epithelial tissues.

Infiltrating lobular carcinomas tend to be slower growing and less aggressive than IDC and patients with ILC tend to have a better prognosis than those with IDC. The inference that PDGF-C expression may be decreased in less aggressive tumors was not apparent for brain and glioblastoma, a very aggressive brain tumor. A further analysis with a greater number of tumors together with relevant clinical information would need to be undertaken to explore this hypothesis.

It was previously demonstrated that over-expression of PDGF-C results in liver fibrosis, steatosis and hepatocellular carcinoma in a PDGF-C transgenic mouse model. Most of the normal livers used in the current immunohistochemical study exhibited fibrosis or steatosis. These conditions may account for the high expression of PDGF-CC observed in the 'normal' livers and their lack of any statistical difference with the PDGF-CC expression levels in hepatocellular carcinomas.

The stromal staining comparison was not able to be evaluated in many of the tissue types examined due to lack of stroma (Tables 12 and 13). There was a significantly higher stromal staining in both the infiltrating ductal ($P=0.039$) and lobular carcinoma tumors ($P=0.006$) compared to stromal staining in normal breast tissue. There was no statistically significant difference in the staining seen between the stromal components of the normal and tumor prostate tissue ($P=0.08$). A significant decrease in the staining of uterine tumor stromal cells ($P=0.011$) was observed, compared to stromal cell staining in normal uterus.

A highly significant difference ($P<0.0001$) between the vessel staining of normal and respective tumor tissues was observed for bladder, brain, breast, bowel, kidney, pancreas and prostate. PDGF-C is implicated to have a role in tumor angiogenesis and the observed higher staining in tumor vessels compared to normal vessels would support this. There was no statistically significant difference in the staining pattern observed between the vessel staining in the normal and tumor liver ($P=0.39$) or uterus ($P=0.20$).

In conclusion, PDGF-CC as detected by the 6B3 antibody was widely expressed across a range of human normal and tumor tissues. The pattern of 6B3 staining in tumor tissue was observed in the cytoplasm and membrane of tumor cells, endothelial cells of vessels and where evaluable the cytoplasm of stromal cells. Overall, a significantly increased level of 6B3 staining in tumor tissue compared to normal tumor tissue was observed.

TABLE 12

PDGF-CC Immunoreactivity of antibody 6B3 on Normal Human Tissue Panel

| | Total | Epithelial cells | Stroma | Vessels | Comments |
|---|---|---|---|---|---|
| NORMAL | | | | | |
| Adrenal | 11/11 | + to ++ | n/e | − to +++ | adrenal medulla not sampled |
| Bladder, urinary | 10/10 | + to +++ | + to +++ | + to +++ | urothelium |
| Bowel, large | 12/12 | −/+ to ++ | + to +++ | ++ to +++ | incl. surface epithelium; lymphocytes within lamina propria |
| Brain | 13/13 | + to +++ | n/e | + to ++ | neurons/glia |
| Breast | 7/7 | + to ++ | − to + | + to ++ | myopeithelial cells |
| Kidney | 12/12 | + to +++ | n/e | + to ++ | parietal cells and endothelial cells in glomeruli (9/9) |

TABLE 12-continued

PDGF-CC Immunoreactivity of antibody 6B3 on Normal Human Tissue Panel

| | Total | Epithelial cells | Stroma | Vessels | Comments |
|---|---|---|---|---|---|
| Heart | 11/11 | + | n/e | + to ++ | myocardium |
| Liver | 13/13 | ++ to +++ | – | – to ++ | hepatocytes and bile ducts (11/11) |
| Lung | 14/14 | + to ++ | n/e | + to ++ | Type I and II pneumocytes |
| Ovary | 10/10 | '+ to +++ | '++ to +++ | '+ to +++ | follicular cysts and corpus luteum |
| Pancreas | 12/12 | + to +++ | n/e | + to ++ | Acini and Islets of Langerhan's; Ducts (8/11) |
| Placenta | 6/6 | + to ++ | – | +++ | trophoblasts |
| Prostate | 12/12 | + to +++ | + to +++ | + to +++ | epithelial cells |
| Spleen | 11/11 | + to +++ | n/e | + to +++ | mainly positive staining in red pulp; stroma difficult to interpret |
| Thyroid | 11/11 | ++ to +++ | – | – to ++ | follicular epithelium |
| Tonsil | 12/12 | + to ++ | n/e | ++ to +++ | germinal centres and lymphocytes |
| Uterus | 3/3 | ++ to +++ | +++ | + to ++ | endometrial glands |

TABLE 13

PDGF-CC Immunoreactivity of antibody 6B3 on Human Tumor Tissue Panel

| | Total | Tumor | Stroma | Vessels |
|---|---|---|---|---|
| TUMOR | | | | |
| Bladder TCC | 10/10 | ++ to +++ | n/e | ++ to +++ |
| Breast IDC | 15/15 | + to +++ | – to +++ | + to +++ |
| Breast ILC | 12/14 | – to +++ | ++ | ++ to +++ |
| Colorectal Adenocarcinoma | 27/28 | – to +++ | + to +++ | + to +++ |
| Glioblastoma Multiforme | 11/11 | + to +++ | n/e | ++ to +++ |
| Gliosarcoma | 9/9 | ++ to +++ | n/e | ++ to +++ |
| Hepatocellular Carcinoma | 16/16 | ++ to +++ | n/e | + to ++ |
| Lung Adenocarcinoma | 13/13 | ++ to +++ | + to ++ | + to +++ |
| Lung SqCC | 19/19 | ++ to +++ | + to +++ | ++ to +++ |
| Metastatic Melanoma | 19/19 | + to +++ | n/e | + to +++ |
| Mesothelioma | 11/11 | + to +++ | + to ++ | + to +++ |
| Ovarian Adenocarcinoma | 2/2 | +++ | n/e | ++ to +++ |
| Pancreatic Adenocarcinoma | 8/8 | + to +++ | ++ to +++ | ++ to +++ |
| Prostate Adenocarcinoma | 13/13 | ++ to +++ | + to ++ | + to +++ |
| Renal Cell Cancer | 24/24 | ++ to +++ | Neg | + to +++ |
| Uterine Adenocarcinoma | 8/8 | ++ to +++ | + to +++ | + to +++ |

Example 8—In Vivo Therapy Studies

A. Colon Carcinoma Xenografts

To investigate the in vivo effects of PDGF-CC expression in colon tumors several cell lines were screened by cell surface and intracellular fluorescent activated cell sorting (FACS) analyses. The human colorecatal carcinoma cell line Colo205 demonstrated intracellular expression of PDGF-CC using 6B3 and 12F5 antibodies, and cell surface PDGFRα expression and was selected for use in vivo tumor xenografts therapy studies.

In vivo investigations were performed in 6-7 week old female athymic BALB/c nude mice, homozygous for the nu/nu allele bred by the Animal Research Centre, WA, Australia. Mice were maintained in autoclaved microisolator cages and housed in a positive pressure containment rack using an individually vented caging system (Techniplast IVC System, Italy). To establish xenografts mice were inoculated subcutaneously into the left flank with $2 \times 10^6$ HT-29 or Colo205 colon carcinoma cells. These cell lines were assessed by FACS analysis and confirmed positive for PDGF-Ra cell surface expression and intracellular PDGF-CC expression (Data not shown).

Treatment with 12F5, 6B3 or PBS as control commenced on Day 0 once tumors had reached a mean volume of 50-100 mm$^3$. Groups of ten mice received intra-peritoneal (i.p.) injections of PBS vehicle control, or antibody at doses of 100 μg, 300 μg or 1.0 mg for a total of 9 doses, 3 times per week for 3 or 4 weeks. Tumor volume was determined using the formula (length×width$^2$)/2, where length was the longest axis and width the measurement at right angles to the length. Mice were euthanized for ethical reasons when tumor volume reached 1000 mm$^3$. Data was expressed as mean tumor volume±SE for each treatment.

Animals (n=1 or 2) were sacrificed from each group on Day 0 and at 1, 2, 3 or 4 weeks post therapy commencement. Tumor xenografts were removed surgically from mice, bisected and either snap frozen or fixed in 10% (v/v) formalin overnight for morphology and pharmacodynamic assessments of proliferation, cell structure, vessel structure and number.

Figure 15:
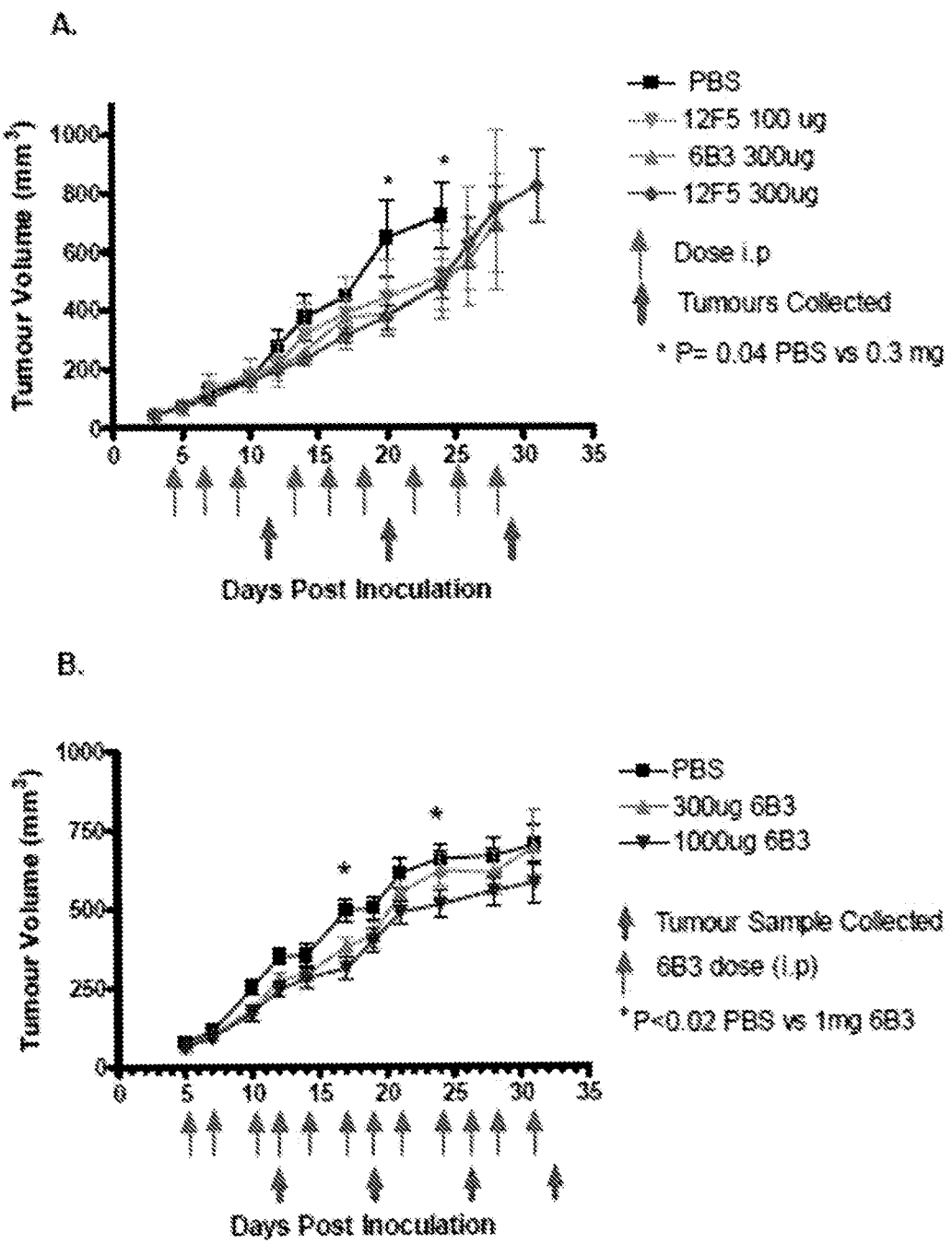
FIG. 15 illustrates the results of colon carcinoma xenografts in mice treated with 300 μs anti-PDGF-C 12F5 or 6B3 three times a week for 3 weeks (15A) and 6B3 therapy at 300 μg and 1 mg doses three times weekly for a longer period of 4 weeks (15B).

The results of colon carcinoma xenografts in mice treated with 300 μg anti-PDGF-C 12F5 or 6B3 three times a week for 3 weeks are shown in FIG. 15A. Both antibodies significantly inhibited tumor growth after 2 weeks of therapy at day 21 and 24 (P=0.04; paired t test). The PBS control arm was culled at Day 25 for ethical tumor burden concerns preventing further efficacy assessments. In a second experiment using the same COLO205 colon carcinoma xenograft model, 6B3 therapy at 300 μg and 1 mg doses was administered three times weekly for a longer period of 4 weeks. Results are shown in FIG. 15B. A dose response was not apparent, however again after 2 and 3 weeks of anti-PDGF-CC therapy a significant difference was observed between PBS control and 1 mg 6B3 (P<0.02 Day 17, Day 24).

B. Colo205 Xenograft Pharmacodynamic Assessments—Tissue Preparation, Histology, and Immunostaining After paraffin embedding, 4 μm Colo205 Xenograft sections were cut and mounted. Sections were deparaffinised in a 60° C. oven followed by washes in xylene and ethanol. Tissue peroxidise activity was quenched by incubation in 3% (v/v) hydrogen peroxide in distilled water for 20 min at room temperature. Sections were treated using 10% citrate buffer, pH 6.0 (Labvision) using a 100° C. boiling water bath for 30 min to 'retrieve' antigens. After cooling, non-specific binding was blocked using Maxitage protein blocking agent (Thermo Fisher) at room temperature for 30 min. Slides were subsequently transferred into slide racks (Thermo Shandon) and developed using the appropriate primary antibodies as follows:

Cell Proliferation by Ki-67 Staining

Sections were incubated with 1/100 rabbit anti-human Ki-67 (Thermo Scientific, RM-9106) for 2 hours at room temperature, washed with PBS and incubated with anti-rabbit IgG-HRP (Dako, K4003) for 30 min. Staining was visualised following development with AEC for 20 min and Mayer's haematoxylin staining.

Blood Vessel Assessments Through Podocalyxin Staining

Sections were incubated with 1 µg goat anti-human podocalyxin (R & D, AF1556) antibody for 2 hours at room temperature. Following washing with PBS, sections were incubated with biotinylated anti-goat secondary and visualized using the Vectastain ABC kit (Vector Laboratories) according to manufacturer's instructions.

All images were captured using the Aperio ImageScope slide scanning and analysis system. Images analyses were performed to determine vessel number and density within tumor samples, and vessel perimeter.

Results

Figure 16:
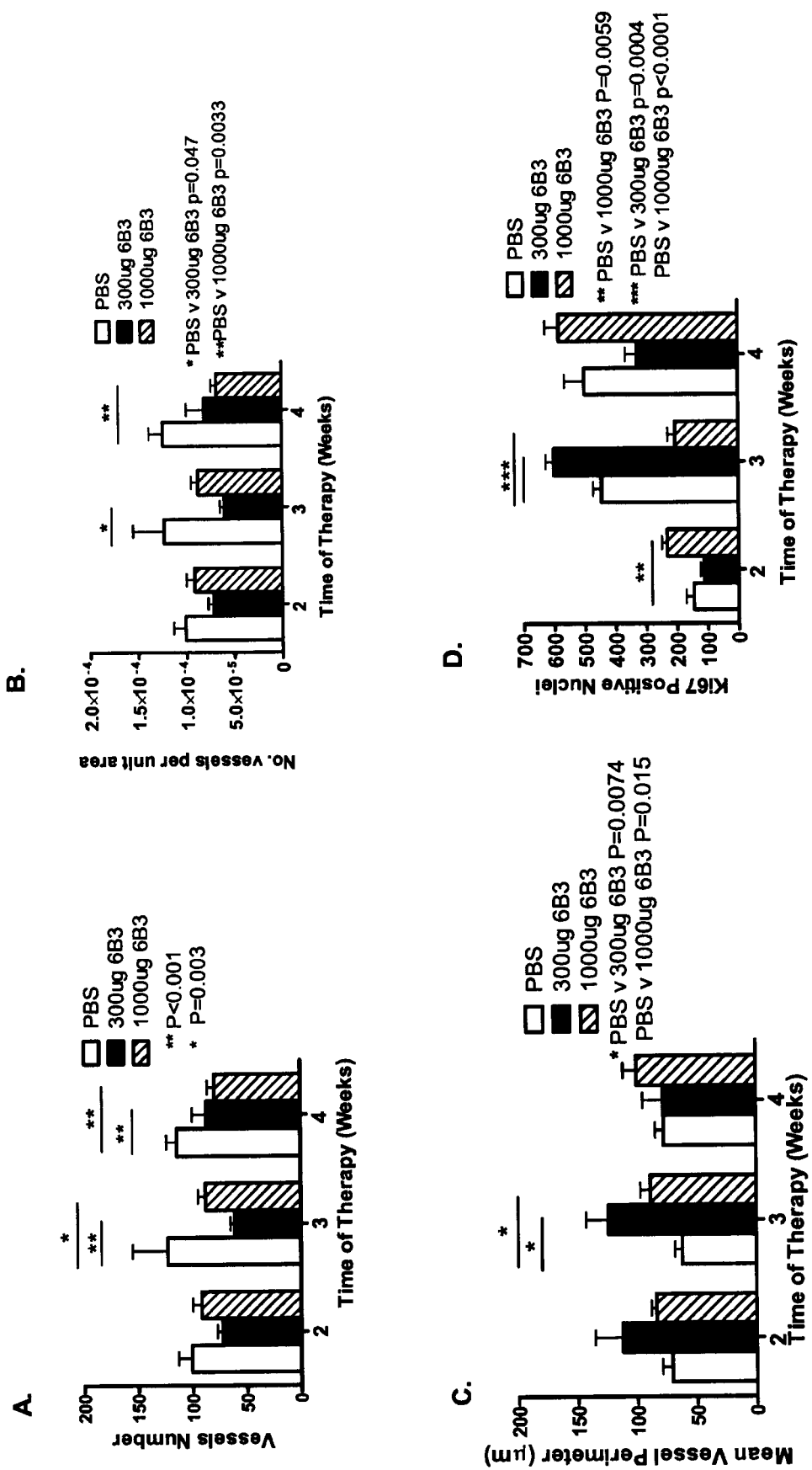
FIG. 16 illustrates immunohistochemical analysis of blood vessels with Podocalyxin staining of Colo205 xenograft sections where panel A demonstrates the change in vessel number, panel B demonstrates the change in number of vessels per unit area, panel C demonstrates the change in vessel perimeter, and panel D demonstrates the change in cell proliferation.

Immunohistochemical identification of blood vessels with Podocalyxin staining of Colo205 xenograft sections was performed and results of analyses for vessel number, perimeter and vessel area are presented in FIG. 16 (A)-(C). The analysis demonstrated that the number and size of the blood vessels within xenografts significantly decreased following 3 and 4 weeks of 6B3 anti-PDGF-CC treatment and the pattern of blood vessels also changed in treated groups compared with PBS control xenografts. These results are again suggestive of anti-angiogenic activity of the anti-PDGF-CC therapy.

Cell proliferation was assessed using the Ki-67 marker. Positive cells were counted using the Aperio ImageScope nuclear staining algorithm. Significant differences in cellular proliferation rates as assessed by Ki67 staining were apparent between PBS control and 6B3 treated xenografts (FIG. 16D) a significant decrease in proliferation was observed after 3 weeks 1 mg 6B3 anti-PDGF-CC treatment. This observation is in agreement with the retarded tumor growth observed (FIG. 15) and in agreement with the in vitro observations of cellular proliferation inhibition (FIG. 12).

C. MDA-MB-231 Breast Carcinoma Xenografts

Human breast tumor cell lines MDA-MB-231, MDA-MB-435 and MCF-7 were cultured at normal conditions in DMEM supplemented with 10% FBS, 100 units/ml penicillin, 100 µg/ml streptomycin, and 2 mM glutamine. RNA (1.25 m) was reverse transcribed according to the manufacturer's instructions (SuperScript VILO cDNA Synthesis Kit, Invitrogen). Real-Time quantitive PCR was performed using KAPA SYBR FAST qPCR Kit Master Mix (2×) Universal (KAPA Biosystems) and in Rotor-Gene Q (Qiagen) Real-Time PCR thermal cycler according to the manufacturer's instruction, totally 40 cycles. PDGF-C(Cat: QT00088935 QuantiTect Primer Assay, Qiagen), B2M (Cat:QT00026551 QuantiTect Primer Assay, Qiagen, reference gene).

For further analysis MDA-MB-231 cells were selected, which were an acknowledged model of breast cancer and also exhibit high PDGF-C mRNA levels. To generate the orthotopic tumor model, $2\times10^6$ MDA-MB-231 cells were injected orthotopically into the $4^{th}$ mammary gland in female 6- to 8-week-old CB17/Icr-Prkdc scid/Crl mice (Charles River). 6B3 Ig and isotype matched control Ig was administrated intraperitoneally twice per week (300 µg/mouse/dose) after the tumors were clearly palpable, defined as the longest diameter measuring over 3 mm. Treatment was continued 7 times. Tumor size was measured twice weekly, and tumor volume was calculated as $width^2 \times length \times \pi/6$. At the end of the experiment, mice were euthanized with 2.5% Avertin (Sigma-Aldrich) and heart perfused with 10 ml PBS followed by 10 ml 2% PFA where after the tumor was removed and processed for sectioning as previously described. The blood vessel staining was performed using goat-anti-mouse podocalyxin (1:100) (R & D Systems). The density of the vessels was manually counted as number of vessel structures/40× field in 10 evenly distributed fields of vision.

A significant reduction in tumor volume following orthotopic injection of MDA-MB-231 cells was observed in 6B3-treated mice compared to control Ig treated animals after the sixth treatment. Overall, treatment with 6B3 Ig caused a significant reduction in tumor size of about 30% after the sixth treatment or three weeks (FIG. 17A), which is in agreement with observations with the colon carcinoma xenografts model. Notably, 6B3 only neutralizes human PDGF-CC, demonstrating the functional importance of paracrine signaling between tumor cells and the adjacent stroma. Staining of sections from the tumors revealed that PDGFRα was only found on tumor stromal cells, presumably invading mouse fibroblasts (data not shown). In sections from tumors treated with 6B3 Ig, the PDGFRα expressing stromal cells were small, and non-stretched while in control Ig treated tumors, these cells were more elongated and visualized of the typical pattern of fibroblasts (data now shown).

Figure 17:
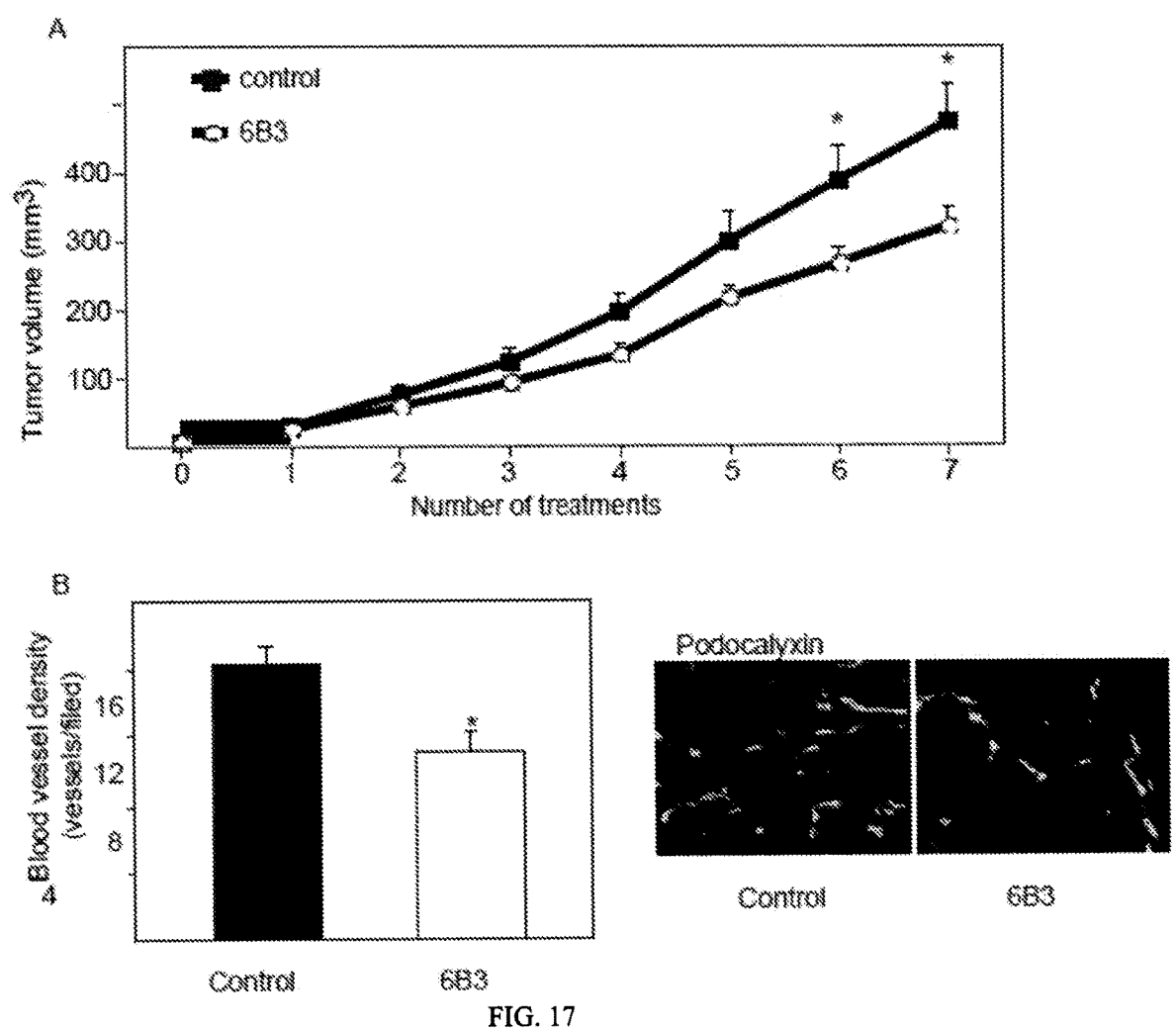
FIG. 17 A-B illustrates that anti-PDGF-CC treatment diminished orthotopic tumor growth via decreased angiogenesis.

Measuring the microvascular density using podocalyxin in 6B3 and control Ig treated tumors revealed that inhibition of PDGF-CC signaling in the tumors reduced the microvascular density by approximately 30% (p<0.05) (FIG. 17B). These results revealed that restriction of PDGF-CC signaling in this mouse model of breast cancer, in a significant way, reduced the growth of the tumor, presumably by reducing the number of tumor blood vessels.

Example 9—Modulation of PDGF-CC Mediated Opening of the Blood-Brain Barrier by Anti-PDGF-C Antibody 6B3

In order to demonstrate the ability of anti-PDGF-C monoclonal antibody 6B3 to target PDGF-CC mediated opening of the blood-brain barrier in the brain, 400 µg of the anti-PDGF-C monoclonal antibody 6B3 or control antibody BM4, both separately diluted in PBS to a total volume of 500 µl were injected intraperitoneally in C57B1/6 mice. After 3-4 hours, injected mice were subsequently anesthetized by isoflurane and mounted in a stereotactic frame. Following skin surgery to expose the scull, a 2 mm hole was drilled in the scull bone at medio-lateral (ML) 0 and anterio-posterior (AP) −2 from bregma. 1.5 µg of highly purified PDGF-CC core domain protein diluted in 3 µl of PBS was injected at a rate of 1 µl/min using a microinjection robot (Neurostar) into the $3^{rd}$ ventricle at ML 0; AP −2 and dorso-ventral (DV) 2.6 from bregma (PDGF-CC ICV). Injection of 3 µl of PBS served as the control (PBS ICV). The wounds were closed with wound clips. Following these procedures, 100 µl of filtered Evans Blue solution was injected into the tail vein of each mouse and allowed to circulate for 2 hours before extensive perfusion with PBS. The time point given in the figure refers to the time after the PDGF-CC ICV injections (3 h, 3.5 h and 4 h). Dissected brains were photographed and extravasated Evans Blue was seen as the remaining blue dye in the brains (FIG. 18A). For quantification of extravasated Evans Blue, the brains were separately homogenized and extracted in 500 µl N,N-dimethylformamide per hemisphere. Evans Blue dye present in the organic N,N-dimethylformamide phase of the samples was quantified using a photometer as described in Yepes M, Sandkvist M, Moore E G, Bugge T H, Strickland D K, Lawrence D A Tissue-type plasminogen activator induces opening of the blood-brain barrier via the LDL receptor-related protein. J Clin Invest. 112:1533-40, 2003, hereby incorporated as reference (FIG. 18B). Briefly, Evans blue levels in were determined from the formula: $(A_{620nm} ((A_{500nm}+A_{740nm})/2))/\text{mg}$ wet weight. The results show that PDGF-CC mediated opening of the blood-brain barrier and extravasation of Evans Blue was significantly reduced when the mice were treated with the anti-PDGF-C antibody (PDGF-CC ICV+6B3) compared to the control antibody BM4 (PDGF-CC ICV+BM4). The results showed that systemic administration of the anti-PDGF-C antibody 6B3 efficiently closes the blood-brain barrier opening upon PDGF-CC induced opening of the same. The results also showed that the antibody preferably has to be administrated intravenously since an i.p. injection at least 4 hours prior to the PDGF-CC mediated signaling to open the blood-brain barrier was required in order to achieve a maximal effect on closing the blood-brain barrier using the anti-PDGF-C antibody 6B3 and prevent extravasation of Evans Blue. The quantification of extravasated Evans Blue from isolated brain demonstrating the closure of the PDGF-CC induced opening of the blood-brain barrier by the anti-PDGF-C antibody 6B3 leading to a significant reduction in Evans Blue extravasation upon the antibody administration. The quantifications of Evans Blue extravasation were measured using injected brains following 3-4.5 hours injection of anti-PDGF-C antibody 6B3, and control antibody BM4 before PDGF-CC ICV.

Example 10. Therapeutic Use of 6B3 (Anti-PDGFC) During Experimental Stroke

A. Materials and Methods

Animals, HFD and antibody treatment. Male or female C57BL/6NTac-Pdgfc$^{tm3633(K242T, K246R, R299S, K318R, N342S, A343T)Arte}$ mice (referred to as PDGF-CC$^{hum}$) were fed with 60% high fat diet (HFD, Research Diets) from weaning (3 weeks after birth) for 16 weeks (19 weeks after birth). PDGFC$^{hum}$ mice were either prophylactically or therapeutically treated with anti-PDGFC (6B3). The mice were injected intraperitoneally with 400 µg of either 6B3, or isotype-matched control antibody (BM4).

Mouse Model of Ischemic Stroke

PDGFC$^{hum}$ mice were anesthetized with 3% isoflurane and maintained on a mask. Mice were then placed securely under a dissecting microscope (Nikon SMZ-2T). The left middle cerebral artery (MCA) was exposed as described before (see Nagai et al., J. Thromb. Haemost. 3, 1379-1384 (2005)), and a laser Doppler flow probe (Type N (18 gauge), Transonic Systems) was placed on the surface of the cerebral cortex located 1.5 mm dorsal median from the bifurcation of MCA. The probe was connected to a flowmeter (Transonic model BLF21) and relative tissue perfusion units (TPU) data was recorded with a continuous data acquisition program (Windaq, DATAQ Instruments). Rose Bengal (Fisher Scientific) was diluted to 10 mg/ml in PBS and then injected into the tail vein with the final dose of 50 mg/kg. A 3.5-mW green light laser (540 nm, Melles Griot) was directed at the MCA from a distance of 6 cm at the onset of the injection, and the TPU of the cerebral cortex was recorded. Total occlusion was achieved when the TPU dropped to less than 30% of pre-occlusion levels.

Assessment of Stroke Volume and Hemorrhage Score

The assessment of stroke volume by TTC was performed essentially as described (see Li et al., Neurology 54, 689-696 (2000)). Briefly, animals were anesthetized with 3% isoflurane and euthanized by decapitation. The brains were then removed and cut into 2-mm-thick coronal sections in a matrix (Harvard Apparatus) and stained with 4% 2,3,5-triphenyltetrazolium chloride (TTC) in PBS for 30 min at RT. Infarcted tissue showed no reaction to TTC while healthy tissue turned a brick red color. Images of the four central sections of each brain were recorded with an Axio Cam Mrc5 (Zeiss) color camera attached to a Zeiss Lumar stereomicroscope, and the captured images were analyzed with an image analysis system (NIH Image J) to calculate the percent hemispheric lesion volume with the following formula:

$$V\% \text{ stroke}=\Sigma(\text{Areas of lesion})/\Sigma(\text{Areas of ipsilateral hemisphere})*100.$$

To assess the hemorrhage score the images of the four central sections were then quantified by using a heme scoring system: 0=no hemorrhage, 1=1-3 petechial, 2=4-6 petechial, 3=greater than 6 petechial, 4=large area of hemorrhage. Scores from 8 images of each brain were totaled and the average score/group was calculated.

B. Results

Since intraventricular injection of active PDGF-CC protein is sufficient to induce BBB opening (see Su et al., Nat Med 14(7), 731-737 (2008)) and its inhibition has been shown to minimize BBB dysfunction in both acute and progressive experimental neuropathology models (see Su et al., Nat Med 14(7), 731-737 (2008), Abrams et al., PLoS One 7(6), e38760 (2012), Adzemovic et al., PLoS One 8(2), e56586 (2013), Fredriksson et al., Ann Clin Transl Neurol 2(7), 722-738 (2015), Lewandowski et al., Acta Neuropathol 131(3), 453-464 (2016), Su et al., Front Cell Neurosci 9, 385 (2015)), we aimed to interfere with the platelet-derived growth factor (PDGF)-CC signaling pathway during experimental stroke. To analyze whether blocking PDGF-CC could ameliorate middle cerebral artery occlusion (MCAO), an animal model of stroke, namely a humanized mouse model was generated. The humanized mouse strain partly contained a genomic DNA that encodes the human PDGF-CC amino acid sequence instead of mouse PDGF-CC amino acid sequence (FIG. 19), allowing for the neutralization of PDGF-CC signaling in vivo with the anti-human PDGFC monoclonal antibody (6B3).

Figure 21:
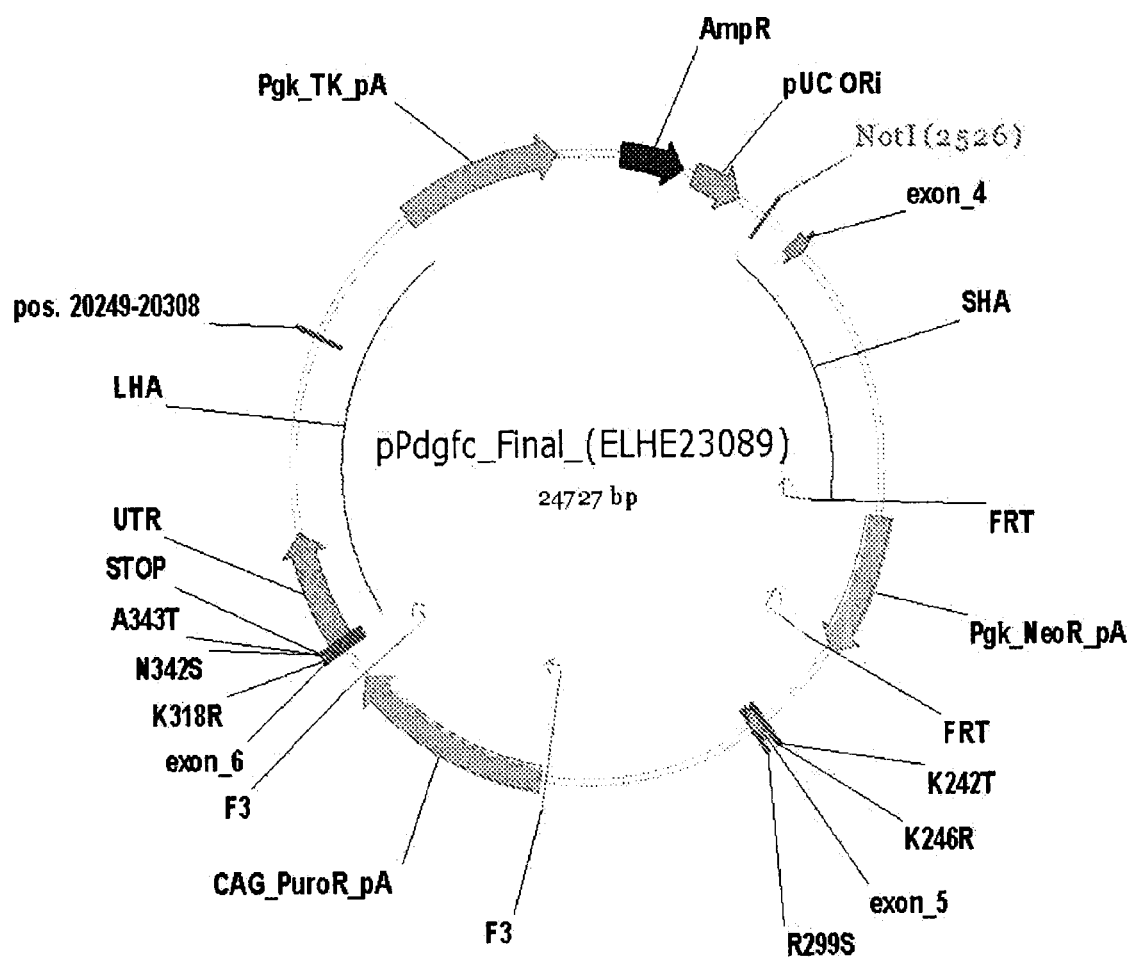
FIG. 21 illustrates the targeting vector for the generation of a humanized mouse model for stroke.
Figure 22:
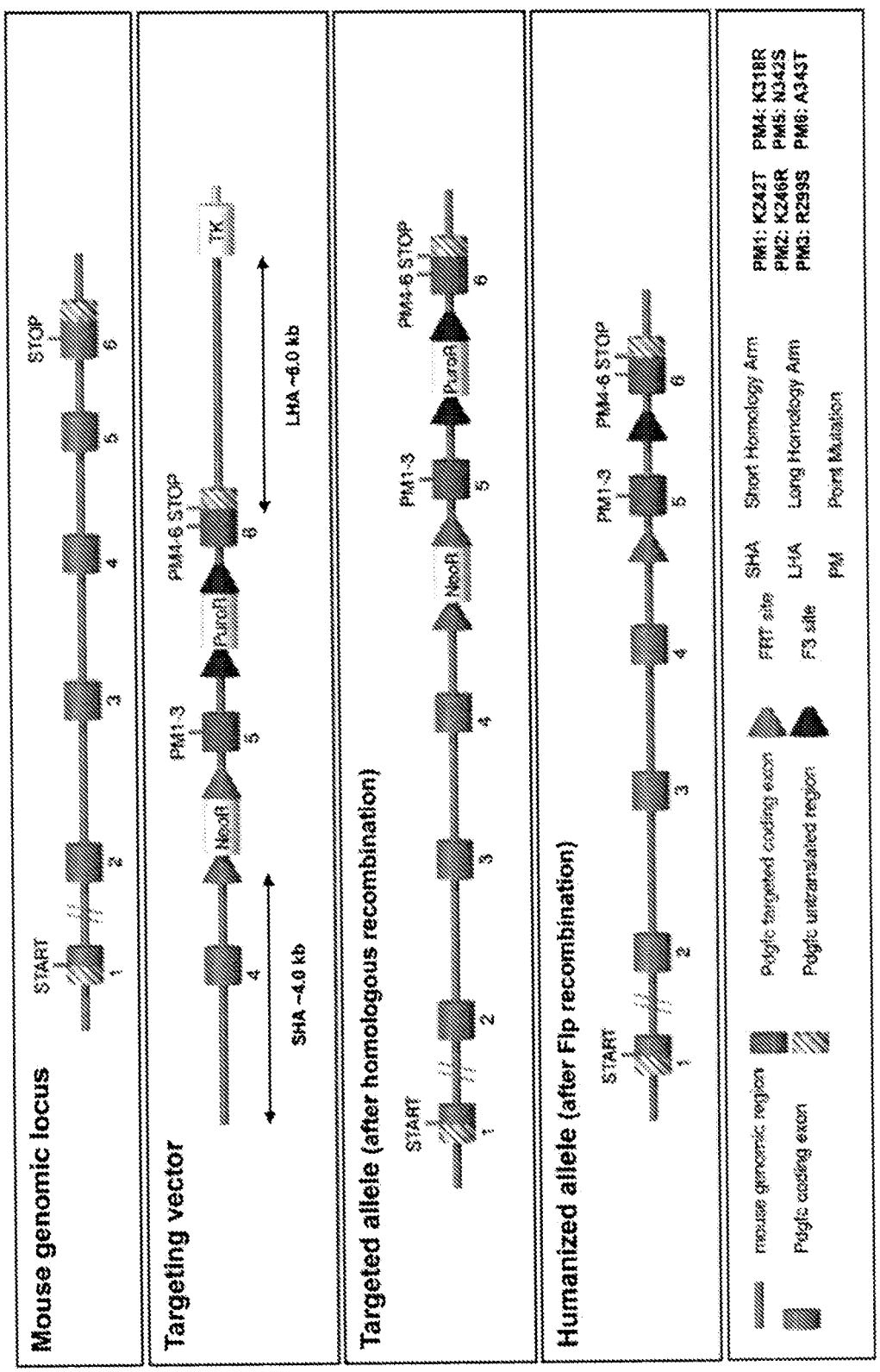
FIG. 22 illustrates the PDGF-CC mouse genomic locus, the targeting vector for the generation of a humanized mouse model for stroke, the targeted PDGF-CC allele after homologous recombination, and the humanized PGCF-CC allele after Flp recombination.

The targeting strategy for replacing mouse PDFG-CC with human PDGF-CC was based on NCBI transcript NM_019971_2 (FIG. 20). Exon 1 contained the translation initiation codon. The K242T, K246R and R299S mutations were introduced into exon 5. The K318R, N342S and A343T mutations were introduced into exon 6. These mutations correspond to the human amino acid sequence. Mouse genomic fragments (obtained from the C57BL/6J RPCIB-731 BAC library) and selected features (such as recombination sites and selection markers, as indicated on the vector map, FIG. 21) were assembled into a targeting vector. If necessary, additional fragments were amplified by qPCR and subcloned. The confirmed sequence of the final targeting vector is shown in FIG. 21. Positive selection markers were flanked by FRT (Neomycin resistance—NeoR) and F3 (Puromycin resistance—PuroR) sites and were inserted into intron 4 and intron 5, respectively. The targeting vector was generated using BAC clones from the C57BL/6J RPCIB-731 BAC library and was transfected into the TaconicArtemis C57BL/6N Tac ES cell line. Homologous recombinant clones were isolated using double positive (NeoR and PuroR) and negative (Thymidine kinase—Tk) selections. The constitutive humanized allele was obtained after in vitro Flp-mediated removal of the selection marker. This allele expressed the mutated Pdgfc K242T, K246R, R299S, K318R, N342S, A343T protein. The remaining recombination sites were located in non-conserved regions of the genome (FIG. 22). Shown below are a wild type mouse PDGF-C protein sequence and mutated version, where the $^{242}$K to $^{242}$T, $^{246}$K to $^{246}$R, $^{299}$R to $^{299}$S, $^{318}$K to $^{318}$R, $^{342}$N to $^{342}$S and $^{343}$A to $^{343}$T mutations are underlined.

```
Original wild type mouse PDGF-C protein sequence
                                       (SEQ ID NO: 104)
MLLLGLLLLT SALAGQRTGT RAESNLSSKL QLSSDKEQNG

VQDPRHERVV TISGNGSIHS PKFPHTYPRN MVLVWRLVAV

DENVRIQLTF DERFGLEDPE DDICKYDFVE VEEPSDGSVL

GRWCGSGTVP GKQTSKGNHI RIRFVSDEYF PSEPGFCIHY

SIIMPQVTET TSPSVLPPSS LSLDLLNNAV TAFSTLEELI

RYLEPDRWQV DLDSLYKPTW QLLGKAFLYG KKSKVVNLNL

LKEEVKLYSC TPRNFSVSIR EELKRTDTIF WPGCLLVKRC

GGNCACCLHN CNECQCVPRK VTKKYHEVLQ LRPKTGVKGL

HKSLTDVALE HHEECDCVCR GNAGG

Humanized PDGF-C protein sequence
                                       (SEQ ID NO: 103)
MLLLGLLLLT SALAGQRTGT RAESNLSSKL QLSSDKEQNG

VQDPRHERVV TISGNGSIHS PKFPHTYPRN MVLVWRLVAV

DENVRIQLTF DERFGLEDPE DDICKYDFVE VEEPSDGSVL

GRWCGSGTVP GKQTSKGNHI RIRFVSDEYF PSEPGFCIHY

SIIMPQVTET TSPSVLPPSS LSLDLLNNAV TAFSTLEELI

RYLEPDRWQV DLDSLYKPTW QLLGKAFLYG KKSKVVNLNL

LTEEVRLYSC TPRNFSVSIR EELKRTDTIF WPGCLLVKRC

GGNCACCLHN CNECQCVPSK VTKKYHEVLQ LRPKTGVRGL

HKSLTDVALE HHEECDCVCR GSTGG
```

6B3 Treatment Before MCAO (Prophylactic Treatment)

Figure 23:
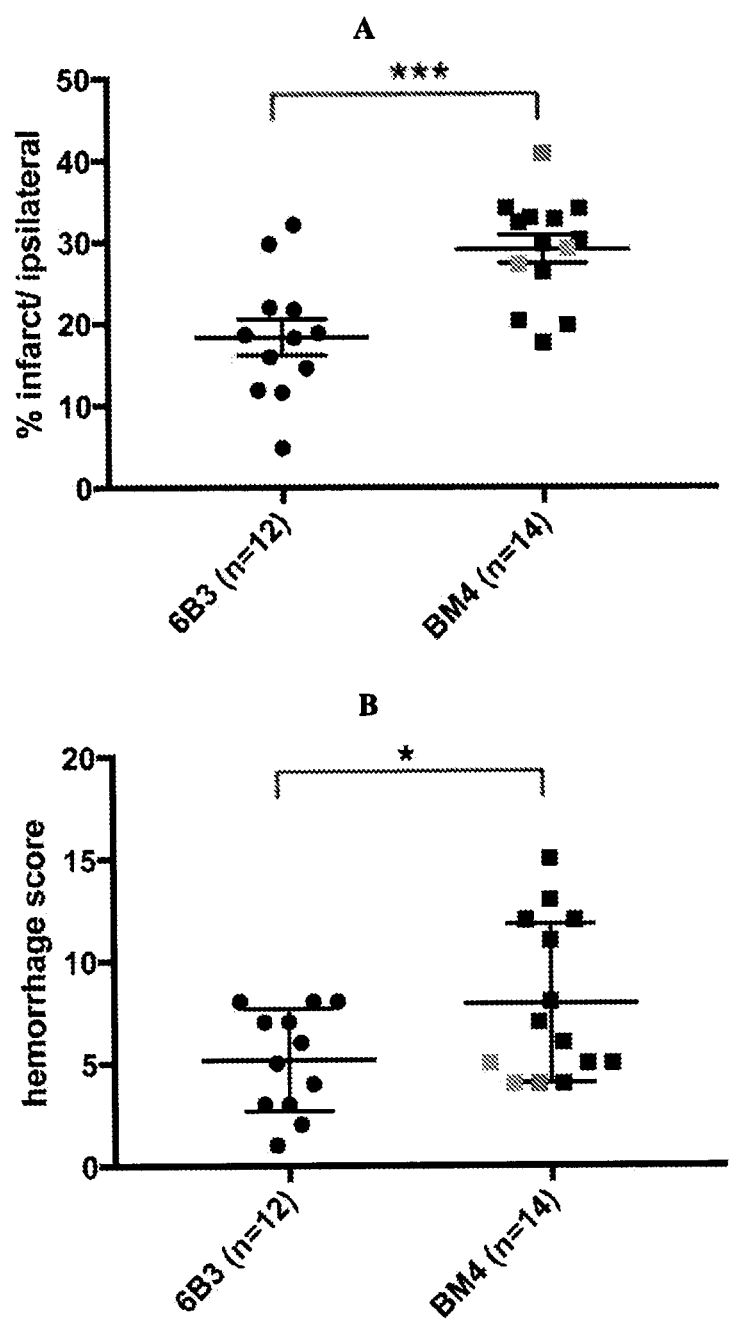
FIG. 23 illustrates the effect of 6B3 treatment before MCAO (prophylactic treatment) on the stroke volume (FIG. 23A) and hemorrhage score (FIG. 23B).

To test if blocking of PDGF-CC with 6B3 before induction of MCAO would significantly reduce stroke volume and hemorrhage score, PDGF-CC$^{hum}$ were fed with HFD for 16 weeks and subsequently MCAO was induced. 24 h before MCAO induction mice were either treated with 6B3 (n=12) or BM4 (n=14). 72 h post MCAO mice were sacrificed and stroke volume was measured using the TTC method. 6B3 treated mice had a stroke volume of 18.35%+/−2.2% and BM4 treated mice 29.21+/−1.72% (average+/−SEM). The p value using unpaired t test was 0.0006. The orange and red dots indicate that these mice had to be sacrificed 24 h or 48 h post MCAO respectively due to worsening of their general health condition (FIG. 23A). 6B3 treated PDGF-CC$^{hum}$ had a hemorrhage score of 5.17+/−0.73 and BM4 treated mice 7.93+/−1.04 (average+/−SEM). The p value using unpaired t test was 0.045. The orange and red dots indicate that these mice had to be sacrificed 24 h or 48 h post MCAO respectively due to worsening of their general health condition (FIG. 23B).

In summary, blocking PDGF-CC with 6B3 before induction of MCAO significantly reduced stroke volume and hemorrhage score.

6B3 Treatment Post MCAO (Therapeutic Treatment)

Figure 24:
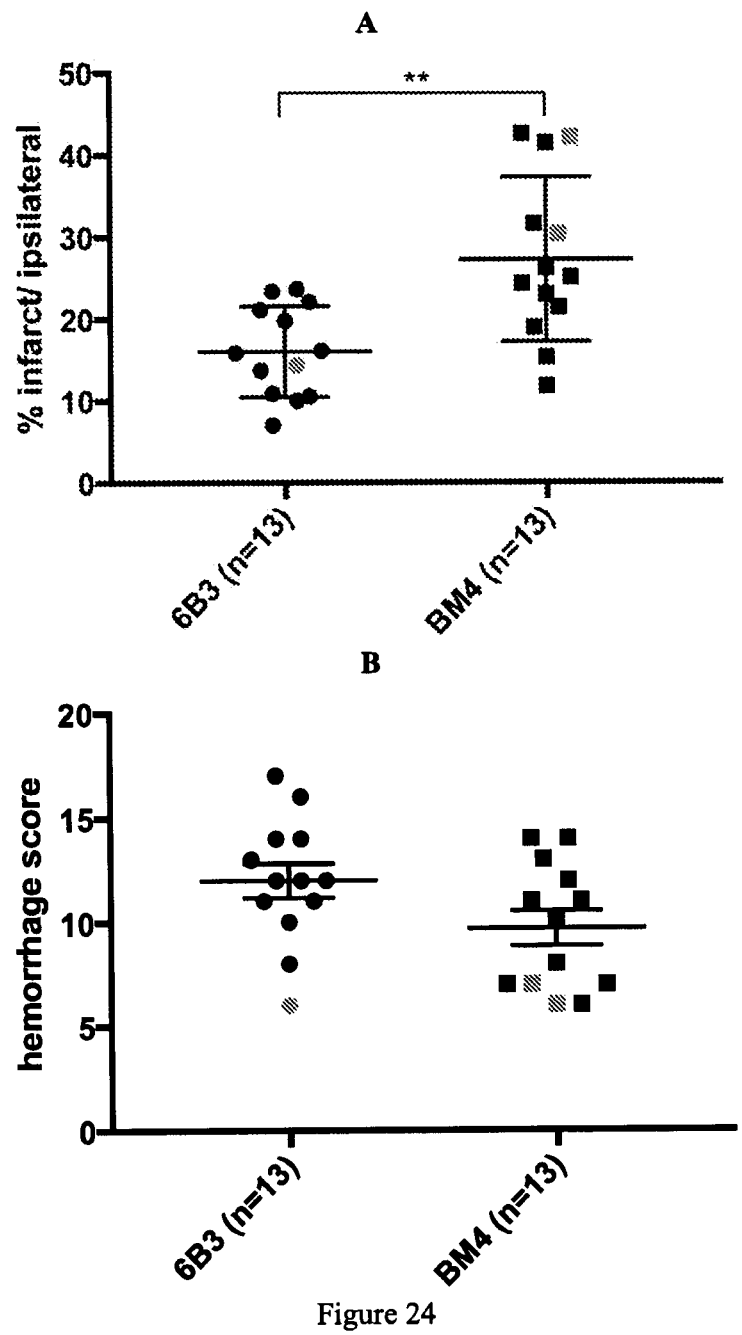
FIG. 24 illustrates the effect of 6B3 treatment post MCAO (therapeutic treatment) on the stroke volume (FIG. 24A) and hemorrhage score (FIG. 24B).

To test if blocking of PDGF-CC with 6B3 post MCAO (therapeutic treatment) would significantly reduce stroke volume and hemorrhage score, PDGF-CC$^{hum}$ were fed with HFD for 16 weeks and MCAO was induced. 1 h post MCAO induction mice were either treated with 6B3 (n=13) or BM4 (n=13). 72 h post MCAO mice were sacrificed and stroke volume was measured using the TTC method. 6B3 treated mice had a stroke volume of 16.05%+/−1.55% and BM4 treated mice 27.32+/−2.78% (average+/−SEM). The p value using unpaired t test was 0.0017. The magenta dots indicate that these mice had to be sacrificed 24 h post MCAO due to worsening of their general health condition (FIG. 24A). 6B3 treated mice had a hemorrhage score of 12+/−0.83 and BM4 treated mice 9.69+/−0.84 (average+/−SEM). The p value using unpaired t test was 0.062. The magenta dots indicate that these mice had to be sacrificed 24 h post MCAO due to worsening of their general health condition (FIG. 24B).

In summary, blocking PDGF-CC with 6B3 after induction of MCAO significantly reduced stroke volume, but did not significantly alter the hemorrhage score.

Example 11. Generation of Humanized Anti-PDGF-CC Antibody 6B3 (hu6B3)

In order to minimize the immunogenicity of 6B3 antibody variable domains, while preserving ligand-binding properties, a humanization process was undertaken. First generation constructs comprised two variants of human variable light chain domains of 6B3 and 3 variants of the humanized variable heavy chain domains of 6B3. These were generated based upon homology modelling analyses with the crystal structures available that were closest to the selected germline sequences.

Variable region amino acids were evaluated based on the following criteria:
  not in the CDR
  buried residues were not changed
  change made if both human consensus and human germline had the same residue
  Outside the $V_L$/$V_H$ interface
  Outside conserved residues as identified by Chothia, Tomlinson, Padlan The expression system was based on the LONZA GS expression system using the pEE 14.4 and pEE6.4 heavy and light chain expression vectors as provided by LONZA Biologics. Synthesized, sequence verified humanized variable light chain and heavy chain domains were cloned into the previously prepared pEE14.4ch6B3LC and pEE6.4ch6B3HC chimeric IgG1κ constructs replacing the murine variable domains. Double gene vectors were constructed followed by transient transfection of chimeric light chains combined with humanized heavy chain candidates as well as humanized light chains candidates combined with chimeric heavy chain. In addition to the hybrid constructs, the fully humanized versions were combined and also analyzed. The binding to PDGF-CC by the six variant hu-ch6B3 products and the hu6B3LC+HC products were assessed by ELISA and Biosensor analyses and lower binding activity compared to the parental murine 6B3 antibody was observed in all products.

Second generation humanized constructs were then generated following evaluation of variable region amino acids based on the following additional criteria:
  Buried residues were changed to the human germline amino acids
  Conservative changes from murine to common human germline consensus sequence Non-conservative changes and back mutations to the murine amino acid were considered according to contribution to antigen binding based upon amino acid structure, side chain interactions and charge.

Figure 27A:
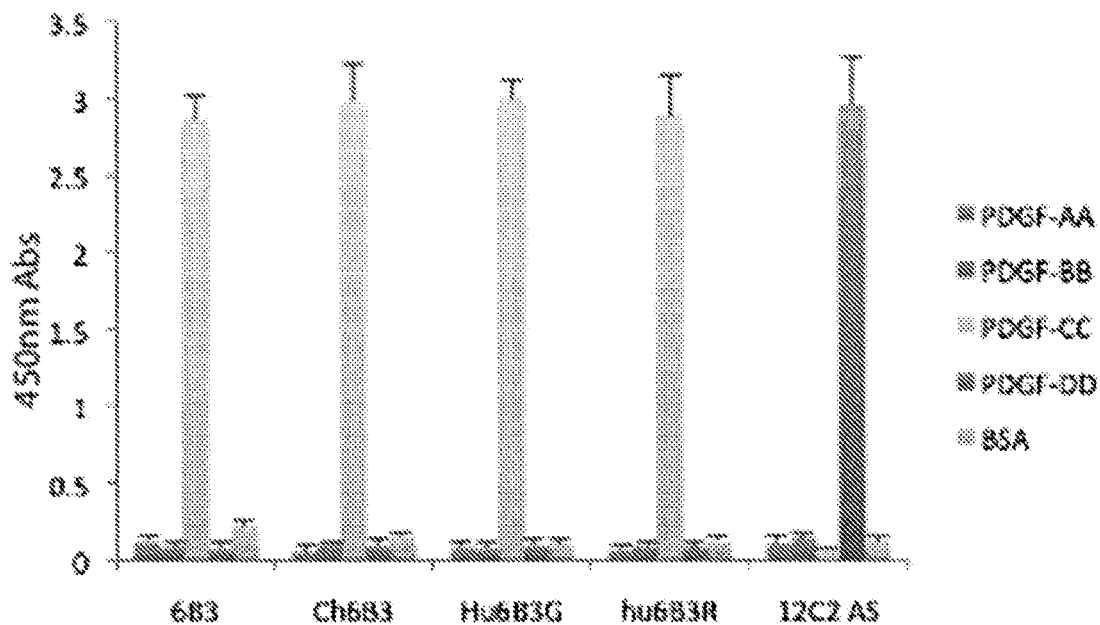
FIG. 27A: Specificity of parental murine anti-PDGF-CC monoclonal antibody 6B3 for PDGF-CC is retained by the chimeric 6B3 (ch6B3) and humanized antibody hu6B3 G and hu6B3 R forms. Only control anti-PDGF-DD antibody 12C2 binds the closely related PDGF family member PDGF-DD.
Figure 27B:
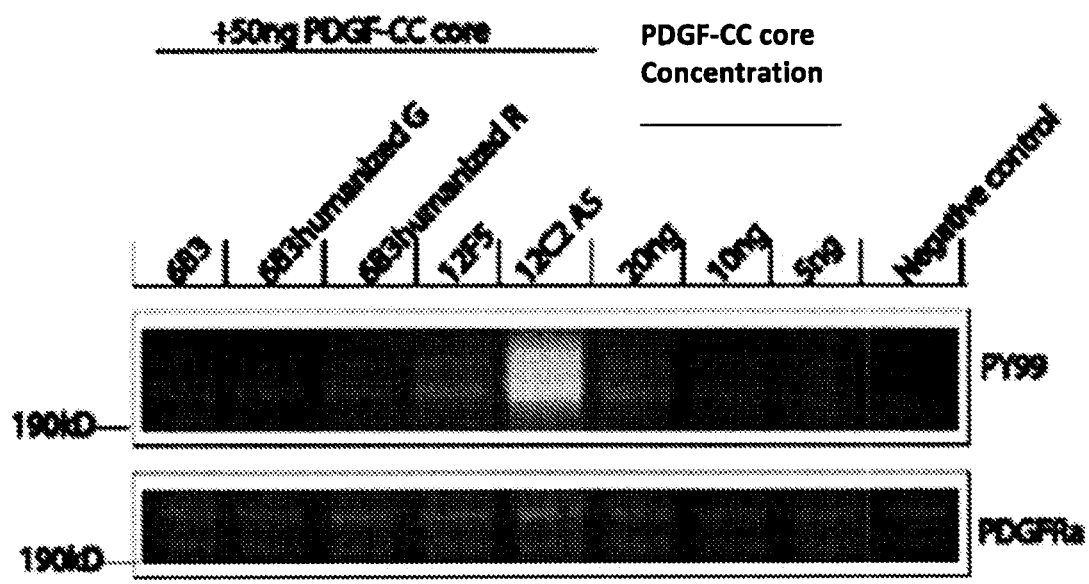
FIG. 27B: PAE cells were stimulated with 50 ng/ml PDGF-CC core protein with or without prior incubation of the cells with purified antibody (5 μg/ml). Activated receptors were detected with an anti-phosphotyrosine antibody PY99. Results demonstrate that humanized 6B3 G and R variants neutralize PDGF-C as effectively as parental murine mAb 6B3. Anti-PDGF-CC monoclonal antibody 12F5, but not control 12C2, was also neutralizing.

Heavy Chain residue glycine G30 was modified to an arginine (R30) in accordance with the commonly occurring initial mu6B3 variable sequence amplified from the hybridoma by degenerate primers. The hu6B3$V_L$ and hu6B3$V_H$ have been engineered into a full length human IgG1κ and IgG4κ context using codon-optimized sequence to achieve stable gene expression in CHO cells. The humanization of the 6B3 anti-PDGF-C antibody involved mutation of 11 amino acids in the $V_L$ (FIG. 25) and 18 amino acid mutations in the $V_H$ chain (FIGS. 26A and 26B). The final hu6B3 antibody demonstrated strong binding to recombinant PDGF-CC by ELISA and high apparent affinity by Biosensor analyses. Specificity and neutralizing activity for PDGF-CC was confirmed in vitro (FIG. 27). The hu6B3 R30 and R30G variants apparent binding characteristics over a concentration range of 2.6 nM-333 nM to immobilized PDGF-CC were analyzed by Biosensor analyses. While both constructs displayed nanomolar apparent binding affinities, the hu6B3"R" version demonstrated superior binding characteristics for PDGF-CC (FIG. 28) and was selected as the final sequence of the IgG1κ humanized antibody hu6B3.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated by reference in their entireties.

What is claimed is:

1. An isolated antibody or antigen-binding fragment thereof that specifically interacts and shows measurable affinity to a polypeptide comprising the active portion of PDGF-C (SEQ ID NO: 2) or a polypeptide having at least 90% sequence identity thereto, wherein said antibody comprises:
   (a) light chain complementary determining regions CDR1L, CDR2L, and CDR3L, wherein CDR1L comprises SEQ ID NO: 16; CDR2L comprises SEQ ID NO: 17; and CDR3L comprises SEQ ID NO: 18; and
   (b) heavy chain complementary determining regions CDR1H, CDR2H, and CDR3H, wherein:
      (i) CDR1H comprises SEQ ID NO: 34, CDR2H comprises SEQ ID NO: 35, and CDR3H comprises SEQ ID NO: 36;
      (ii) CDR1H comprises SEQ ID NO: 46, CDR2H comprises SEQ ID NO: 47, and CDR3H comprises SEQ ID NO: 48; or
      (iii) CDR1H comprises SEQ ID NO: 49, CDR2L comprises SEQ ID NO: 50, and CDR3H comprises SEQ ID NO: 51.

2. An isolated antibody or antigen-binding fragment thereof that specifically interacts and shows measurable affinity to a polypeptide comprising the active portion of PDGF-C (SEQ ID NO: 2) or a polypeptide having at least 90% sequence identity thereto, wherein said antibody comprises a light and a heavy chain, wherein the light chain and the heavy chain of the antibody comprise the respective sequences of (i) SEQ ID NOs: 4 and 10, (ii) SEQ ID NOs: 8 and 14, or (iii) SEQ ID NOs: 9 and 15.

* * * * *

SEQUENCE LISTING

<160> NUMBER OF SEQ ID NOS: 111

<210> SEQ ID NO 1
<211> LENGTH: 345
<212> TYPE: PRT
<213> ORGANISM: Homo sapiens

<400> SEQUENCE: 1

```
Met Ser Leu Phe Gly Leu Leu Leu Val Thr Ser Ala Leu Ala Gly Gln
1               5                   10                  15

Arg Arg Gly Thr Gln Ala Glu Ser Asn Leu Ser Ser Lys Phe Gln Phe
            20                  25                  30

Ser Ser Asn Lys Glu Gln Asn Gly Val Gln Asp Pro Gln His Glu Arg
        35                  40                  45

Ile Ile Thr Val Ser Thr Asn Gly Ser Ile His Ser Pro Arg Phe Pro
    50                  55                  60

His Thr Tyr Pro Arg Asn Thr Val Leu Val Trp Arg Leu Val Ala Val
65                  70                  75                  80

Glu Glu Asn Val Trp Ile Gln Leu Thr Phe Asp Glu Arg Phe Gly Leu
                85                  90                  95

Glu Asp Pro Glu Asp Asp Ile Cys Lys Tyr Asp Phe Val Glu Val Glu
            100                 105                 110

Glu Pro Ser Asp Gly Thr Ile Leu Gly Arg Trp Cys Gly Ser Gly Thr
        115                 120                 125

Val Pro Gly Lys Gln Ile Ser Lys Gly Asn Gln Ile Arg Ile Arg Phe
    130                 135                 140

Val Ser Asp Glu Tyr Phe Pro Ser Glu Pro Gly Phe Cys Ile His Tyr
145                 150                 155                 160

Asn Ile Val Met Pro Gln Phe Thr Glu Ala Val Ser Pro Ser Val Leu
                165                 170                 175

Pro Pro Ser Ala Leu Pro Leu Asp Leu Leu Asn Asn Ala Ile Thr Ala
            180                 185                 190

Phe Ser Thr Leu Glu Asp Leu Ile Arg Tyr Leu Glu Pro Glu Arg Trp
        195                 200                 205

Gln Leu Asp Leu Glu Asp Leu Tyr Arg Pro Thr Trp Gln Leu Leu Gly
    210                 215                 220

Lys Ala Phe Val Phe Gly Arg Lys Ser Arg Val Val Asp Leu Asn Leu
225                 230                 235                 240

Leu Thr Glu Glu Val Arg Leu Tyr Ser Cys Thr Pro Arg Asn Phe Ser
```

```
                    245                 250                 255
Val Ser Ile Arg Glu Glu Leu Lys Arg Thr Asp Thr Ile Phe Trp Pro
            260                 265                 270

Gly Cys Leu Leu Val Lys Arg Cys Gly Gly Asn Cys Ala Cys Cys Leu
            275                 280                 285

His Asn Cys Asn Glu Cys Gln Cys Val Pro Ser Lys Val Thr Lys Lys
            290                 295                 300

Tyr His Glu Val Leu Gln Leu Arg Pro Lys Thr Gly Val Arg Gly Leu
305                 310                 315                 320

His Lys Ser Leu Thr Asp Val Ala Leu Glu His His Glu Glu Cys Asp
            325                 330                 335

Cys Val Cys Arg Gly Ser Thr Gly Gly
            340                 345

<210> SEQ ID NO 2
<211> LENGTH: 115
<212> TYPE: PRT
<213> ORGANISM: Homo sapiens
<220> FEATURE:
<221> NAME/KEY: SITE
<222> LOCATION: (1)..(115)
<223> OTHER INFORMATION: core active domain

<400> SEQUENCE: 2

Arg Lys Ser Arg Val Val Asp Leu Asn Leu Leu Thr Glu Glu Val Arg
1               5                   10                  15

Leu Tyr Ser Cys Thr Pro Arg Asn Phe Ser Val Ser Ile Arg Glu Glu
            20                  25                  30

Leu Lys Arg Thr Asp Thr Ile Phe Trp Pro Gly Cys Leu Leu Val Lys
        35                  40                  45

Arg Cys Gly Gly Asn Cys Ala Cys Cys Leu His Asn Cys Asn Glu Cys
    50                  55                  60

Gln Cys Val Pro Ser Lys Val Thr Lys Lys Tyr His Glu Val Leu Gln
65                  70                  75                  80

Leu Arg Pro Lys Thr Gly Val Arg Gly Leu His Lys Ser Leu Thr Asp
                85                  90                  95

Val Ala Leu Glu His His Glu Glu Cys Asp Cys Val Cys Arg Gly Ser
            100                 105                 110

Thr Gly Gly
        115

<210> SEQ ID NO 3
<211> LENGTH: 19
<212> TYPE: PRT
<213> ORGANISM: artificial
<220> FEATURE:
<223> OTHER INFORMATION: synthetic

<400> SEQUENCE: 3

Ser Val Ser Ile Arg Glu Glu Leu Lys Arg Thr Asp Thr Ile Phe Trp
1               5                   10                  15

Pro Gly Cys

<210> SEQ ID NO 4
<211> LENGTH: 114
<212> TYPE: PRT
<213> ORGANISM: Mus musculus

<400> SEQUENCE: 4
```

Asp Ile Val Met Thr Gln Ser Pro Ser Ser Leu Ala Met Ser Val Gly
1               5                   10                  15

Gln Lys Val Thr Met Ser Cys Lys Ser Gln Ser Leu Leu Asn Ser
                20                  25                  30

Arg Asn Gln Lys Asn Tyr Leu Ala Trp Tyr Gln Gln Lys Pro Gly Gln
            35                  40                  45

Ser Pro Lys Leu Leu Val Tyr Phe Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Gln
                85                  90                  95

His Tyr Ser Thr Pro Leu Thr Phe Gly Ala Gly Thr Lys Leu Glu Leu
                100                 105                 110

Lys Arg

<210> SEQ ID NO 5
<211> LENGTH: 114
<212> TYPE: PRT
<213> ORGANISM: Mus musculus

<400> SEQUENCE: 5

Asp Ile Val Met Thr Gln Ser Pro Ser Ser Leu Ala Met Ser Val Gly
1               5                   10                  15

Gln Lys Val Ala Val Ser Cys Lys Ser Ser Gln Ser Leu Leu Asn Ser
                20                  25                  30

Ser Asn Gln Lys Asn Tyr Leu Ala Trp Tyr Gln Gln Lys Pro Gly Gln
            35                  40                  45

Ser Pro Lys Leu Leu Val Tyr Phe Ala Ser Thr Arg Asp Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Gln
                85                  90                  95

His Tyr Ser Thr Pro Leu Thr Phe Gly Ala Gly Thr Lys Leu Glu Leu
                100                 105                 110

Lys Arg

<210> SEQ ID NO 6
<211> LENGTH: 113
<212> TYPE: PRT
<213> ORGANISM: Mus musculus

<400> SEQUENCE: 6

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
                20                  25                  30

Asn Gly Asn Thr Tyr Leu His Trp Tyr Leu Gln Lys Pro Gly Gln Ser
            35                  40                  45

Pro Lys Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Met Gly Val Tyr Tyr Cys Phe Gln Gly
                85                  90                  95

```
Thr His Val Pro Phe Thr Phe Gly Ser Gly Thr Lys Leu Glu Ile Lys
                100                 105                 110
Arg

<210> SEQ ID NO 7
<211> LENGTH: 114
<212> TYPE: PRT
<213> ORGANISM: Mus musculus

<400> SEQUENCE: 7

Asp Ile Val Met Thr Gln Ser Pro Ser Ser Leu Ala Met Ser Val Gly
1               5                   10                  15

Gln Lys Val Thr Met Ser Cys Lys Ser Ser Gln Ser Leu Leu Asn Ser
            20                  25                  30

Arg Asn Gln Lys Asn Tyr Leu Ala Trp Tyr Gln Gln Lys Pro Gly Gln
        35                  40                  45

Ser Pro Lys Leu Leu Val Tyr Phe Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Gln
                85                  90                  95

His Tyr Ser Thr Pro Leu Thr Phe Gly Ala Gly Thr Lys Leu Glu Leu
                100                 105                 110

Lys Arg

<210> SEQ ID NO 8
<211> LENGTH: 114
<212> TYPE: PRT
<213> ORGANISM: Mus musculus

<400> SEQUENCE: 8

Asp Ile Val Met Thr Gln Ser Pro Ser Ser Leu Ala Met Ser Val Gly
1               5                   10                  15

Gln Lys Val Thr Met Ser Cys Lys Ser Ser Gln Ser Leu Leu Asn Ser
            20                  25                  30

Arg Asn Gln Lys Asn Tyr Leu Ala Trp Tyr Gln Gln Lys Pro Gly Gln
        35                  40                  45

Ser Pro Lys Leu Leu Val Tyr Phe Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Gln
                85                  90                  95

His Tyr Ser Thr Pro Leu Thr Phe Gly Ala Gly Thr Lys Leu Glu Leu
                100                 105                 110

Lys Arg

<210> SEQ ID NO 9
<211> LENGTH: 114
<212> TYPE: PRT
<213> ORGANISM: Mus musculus

<400> SEQUENCE: 9

Asp Ile Val Met Thr Gln Ser Pro Ser Ser Leu Ala Met Ser Val Gly
1               5                   10                  15
```

-continued

```
Glu Arg Ala Thr Ile Asn Cys Lys Ser Ser Gln Ser Leu Leu Asn Ser
                20                  25                  30

Arg Asn Gln Lys Asn Tyr Leu Ala Trp Tyr Gln Lys Pro Gly Gln
            35                  40                  45

Pro Pro Lys Leu Leu Ile Tyr Phe Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Val Gln Ala Glu Asp Val Ala Val Tyr Tyr Cys Gln Gln
                85                  90                  95

His Tyr Thr Pro Leu Thr Phe Gly Gly Gly Thr Lys Val Glu Leu
                100                 105                 110

Lys Arg

<210> SEQ ID NO 10
<211> LENGTH: 121
<212> TYPE: PRT
<213> ORGANISM: Mus musculus

<400> SEQUENCE: 10

Gln Val Gln Leu Gln Gln Ser Gly Val Glu Val Ala Arg Pro Gly Ala
1               5                   10                  15

Ser Val Lys Leu Ser Cys Lys Ala Ser Gly Tyr Thr Phe Arg Ser Tyr
                20                  25                  30

Gly Ile Thr Trp Val Arg Gln Arg Thr Gly Gln Gly Leu Glu Trp Ile
            35                  40                  45

Gly Glu Ile Tyr Pro Arg Ser Gly Lys Thr Tyr Tyr Asn Glu Lys Phe
 50                  55                  60

Lys Gly Lys Ala Thr Leu Thr Ala Asp Thr Ser Ser Ser Thr Val Tyr
 65                  70                  75                  80

Met Glu Leu Arg Ser Leu Thr Ser Glu Asp Ser Ala Val Tyr Phe Cys
                85                  90                  95

Ala Arg Glu Gly Tyr Gly Tyr Asp Gly Gly Tyr Phe Asp Tyr Trp Gly
                100                 105                 110

Gln Gly Thr Thr Leu Thr Val Ser Ser
            115                 120

<210> SEQ ID NO 11
<211> LENGTH: 121
<212> TYPE: PRT
<213> ORGANISM: Mus musculus

<400> SEQUENCE: 11

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Ile Phe Ile Ser Tyr
                20                  25                  30

Gly Ile Ser Trp Val Lys Gln Arg Thr Gly Gln Gly Leu Glu Trp Ile
            35                  40                  45

Gly Glu Ile Tyr Pro Arg Ser Gly Lys Thr Tyr Tyr Asn Glu Lys Phe
 50                  55                  60

Lys Asp Lys Ala Ala Leu Thr Ala Asp Lys Ser Ser Ser Ile Ala Tyr
 65                  70                  75                  80

Met Glu Leu Arg Ser Leu Thr Ser Glu Asp Ser Ala Val Tyr Phe Cys
                85                  90                  95

Ala Arg Glu Gly Tyr Gly Tyr Asp Gly Gly Tyr Phe Asp Tyr Trp Gly
```

```
                    100                 105                 110
Gln Gly Thr Ile Leu Thr Val Ser Ser
        115                 120

<210> SEQ ID NO 12
<211> LENGTH: 120
<212> TYPE: PRT
<213> ORGANISM: Mus musculus

<400> SEQUENCE: 12

Glu Val Lys Leu Glu Glu Ser Gly Gly Gly Leu Val Gln Pro Gly Gly
1               5                   10                  15

Ser Arg Glu Leu Ser Cys Glu Gly Ser Gly Phe Thr Phe Ser Gly Phe
            20                  25                  30

Trp Met Ser Trp Val Arg Gln Thr Pro Gly Lys Thr Leu Glu Trp Ile
        35                  40                  45

Gly Asp Ile Asn Ser Asp Gly Ser Ala Ile Ile Tyr Ala Pro Ser Ile
    50                  55                  60

Lys Asp Arg Phe Thr Ile Phe Arg Asp Asn Asp Lys Ser Thr Leu Tyr
65                  70                  75                  80

Leu Gln Met Asn Asn Val Arg Ser Glu Asp Thr Ala Thr Tyr Phe Cys
                85                  90                  95

Met Arg Trp Gly Tyr Tyr Gly Ser Asn Tyr Phe Asp Tyr Trp Gly Gln
            100                 105                 110

Gly Thr Thr Leu Thr Val Ser Ser
        115                 120

<210> SEQ ID NO 13
<211> LENGTH: 121
<212> TYPE: PRT
<213> ORGANISM: Mus musculus

<400> SEQUENCE: 13

Gln Val Gln Leu Gln Gln Ser Gly Val Glu Val Ala Arg Pro Gly Ala
1               5                   10                  15

Ser Val Lys Leu Ser Cys Lys Ala Ser Gly Tyr Thr Phe Arg Ser Tyr
            20                  25                  30

Gly Ile Thr Trp Val Arg Gln Arg Thr Gly Gln Gly Leu Glu Trp Ile
        35                  40                  45

Gly Glu Ile Tyr Pro Arg Ser Gly Lys Thr Tyr Tyr Asn Glu Lys Phe
    50                  55                  60

Lys Gly Lys Ala Thr Leu Thr Ala Asp Thr Ser Ser Ser Thr Val Tyr
65                  70                  75                  80

Met Glu Leu Arg Ser Leu Thr Ser Glu Asp Ser Ala Val Tyr Phe Cys
                85                  90                  95

Ala Arg Glu Gly Tyr Gly Tyr Asp Gly Gly Tyr Phe Asp Tyr Trp Gly
            100                 105                 110

Gln Gly Thr Thr Leu Thr Val Ser Ser
        115                 120

<210> SEQ ID NO 14
<211> LENGTH: 121
<212> TYPE: PRT
<213> ORGANISM: Mus musculus

<400> SEQUENCE: 14

Gln Val Gln Leu Gln Gln Ser Gly Val Glu Val Ala Arg Pro Gly Ala
1               5                   10                  15
```

```
Ser Val Lys Leu Ser Cys Lys Ala Ser Gly Tyr Thr Phe Gly Ser Tyr
            20                  25                  30

Gly Ile Thr Trp Val Arg Gln Arg Thr Gly Gln Gly Leu Glu Trp Ile
        35                  40                  45

Gly Glu Ile Tyr Pro Arg Ser Gly Lys Thr Tyr Tyr Asn Glu Lys Phe
    50                  55                  60

Lys Gly Lys Ala Thr Leu Thr Ala Asp Thr Ser Ser Ser Thr Val Tyr
65                  70                  75                  80

Met Glu Leu Arg Ser Leu Thr Ser Glu Asp Ser Ala Val Tyr Phe Cys
                85                  90                  95

Ala Arg Glu Gly Tyr Gly Tyr Asp Gly Gly Tyr Phe Asp Tyr Trp Gly
            100                 105                 110

Gln Gly Thr Thr Leu Thr Val Ser Ser
        115                 120
```

<210> SEQ ID NO 15
<211> LENGTH: 121
<212> TYPE: PRT
<213> ORGANISM: Mus musculus

<400> SEQUENCE: 15

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Arg Ser Tyr
            20                  25                  30

Gly Ile Thr Trp Val Arg Gln Ala Thr Gly Gln Gly Leu Glu Trp Met
        35                  40                  45

Gly Glu Ile Tyr Pro Arg Ser Gly Lys Thr Gly Tyr Ala Gln Lys Phe
    50                  55                  60

Gln Gly Arg Val Thr Met Thr Ala Asp Thr Ser Thr Ser Thr Val Tyr
65                  70                  75                  80

Met Glu Leu Arg Ser Leu Arg Ser Glu Asp Ser Ala Val Tyr Phe Cys
                85                  90                  95

Ala Arg Glu Gly Tyr Gly Tyr Asp Gly Gly Tyr Phe Asp Tyr Trp Gly
            100                 105                 110

Gln Gly Thr Leu Val Thr Val Ser Ser
        115                 120
```

<210> SEQ ID NO 16
<211> LENGTH: 17
<212> TYPE: PRT
<213> ORGANISM: Mus musculus

<400> SEQUENCE: 16

```
Lys Ser Ser Gln Ser Leu Leu Asn Ser Arg Asn Gln Lys Asn Tyr Leu
1               5                   10                  15

Ala
```

<210> SEQ ID NO 17
<211> LENGTH: 7
<212> TYPE: PRT
<213> ORGANISM: Mus musculus

<400> SEQUENCE: 17

```
Phe Ala Ser Thr Arg Glu Ser
1               5
```

```
<210> SEQ ID NO 18
<211> LENGTH: 9
<212> TYPE: PRT
<213> ORGANISM: Mus musculus

<400> SEQUENCE: 18

Gln Gln His Tyr Ser Thr Pro Leu Thr
1               5

<210> SEQ ID NO 19
<211> LENGTH: 17
<212> TYPE: PRT
<213> ORGANISM: Mus musculus

<400> SEQUENCE: 19

Lys Ser Ser Gln Ser Leu Leu Asn Ser Ser Asn Gln Lys Asn Tyr Leu
1               5                   10                  15

Ala

<210> SEQ ID NO 20
<211> LENGTH: 7
<212> TYPE: PRT
<213> ORGANISM: Mus musculus

<400> SEQUENCE: 20

Phe Ala Ser Thr Arg Asp Ser
1               5

<210> SEQ ID NO 21
<211> LENGTH: 9
<212> TYPE: PRT
<213> ORGANISM: Mus musculus

<400> SEQUENCE: 21

Gln Gln His Tyr Ser Thr Pro Leu Thr
1               5

<210> SEQ ID NO 22
<211> LENGTH: 16
<212> TYPE: PRT
<213> ORGANISM: Mus musculus

<400> SEQUENCE: 22

Arg Ser Ser Gln Ser Ile Val His Ser Asn Gly Asn Thr Tyr Leu His
1               5                   10                  15

<210> SEQ ID NO 23
<211> LENGTH: 7
<212> TYPE: PRT
<213> ORGANISM: Homo sapiens

<400> SEQUENCE: 23

Arg Val Ser Asn Arg Phe Ser
1               5

<210> SEQ ID NO 24
<211> LENGTH: 9
<212> TYPE: PRT
<213> ORGANISM: Homo sapiens

<400> SEQUENCE: 24

Phe Gln Gly Thr His Val Pro Phe Thr
1               5
```

```
<210> SEQ ID NO 25
<211> LENGTH: 17
<212> TYPE: PRT
<213> ORGANISM: Homo sapiens

<400> SEQUENCE: 25

Lys Ser Ser Gln Ser Leu Leu Asn Ser Arg Asn Gln Lys Asn Tyr Leu
1               5                   10                  15

Ala

<210> SEQ ID NO 26
<211> LENGTH: 7
<212> TYPE: PRT
<213> ORGANISM: Mus musculus

<400> SEQUENCE: 26

Phe Ala Ser Thr Arg Glu Ser
1               5

<210> SEQ ID NO 27
<211> LENGTH: 9
<212> TYPE: PRT
<213> ORGANISM: Mus musculus

<400> SEQUENCE: 27

Gln Gln His Tyr Ser Thr Pro Leu Thr
1               5

<210> SEQ ID NO 28
<211> LENGTH: 17
<212> TYPE: PRT
<213> ORGANISM: Mus musculus

<400> SEQUENCE: 28

Lys Ser Ser Gln Ser Leu Leu Asn Ser Arg Asn Gln Lys Asn Tyr Leu
1               5                   10                  15

Ala

<210> SEQ ID NO 29
<211> LENGTH: 7
<212> TYPE: PRT
<213> ORGANISM: Mus musculus

<400> SEQUENCE: 29

Phe Ala Ser Thr Arg Glu Ser
1               5

<210> SEQ ID NO 30
<211> LENGTH: 9
<212> TYPE: PRT
<213> ORGANISM: Mus musculus

<400> SEQUENCE: 30

Gln Gln His Tyr Ser Thr Pro Leu Thr
1               5

<210> SEQ ID NO 31
<211> LENGTH: 17
<212> TYPE: PRT
<213> ORGANISM: Mus musculus

<400> SEQUENCE: 31

Lys Ser Ser Gln Ser Leu Leu Asn Ser Arg Asn Gln Lys Asn Tyr Leu
1               5                   10                  15
```

Ala

<210> SEQ ID NO 32
<211> LENGTH: 7
<212> TYPE: PRT
<213> ORGANISM: Mus musculus

<400> SEQUENCE: 32

Phe Ala Ser Thr Arg Glu Ser
1               5

<210> SEQ ID NO 33
<211> LENGTH: 9
<212> TYPE: PRT
<213> ORGANISM: Mus musculus

<400> SEQUENCE: 33

Gln Gln His Tyr Ser Thr Pro Leu Thr
1               5

<210> SEQ ID NO 34
<211> LENGTH: 10
<212> TYPE: PRT
<213> ORGANISM: Mus musculus

<400> SEQUENCE: 34

Gly Tyr Thr Phe Arg Ser Tyr Gly Ile Thr
1               5                   10

<210> SEQ ID NO 35
<211> LENGTH: 17
<212> TYPE: PRT
<213> ORGANISM: Mus musculus

<400> SEQUENCE: 35

Glu Ile Tyr Pro Arg Ser Gly Lys Thr Tyr Tyr Asn Glu Lys Phe Lys
1               5                   10                  15

Gly

<210> SEQ ID NO 36
<211> LENGTH: 12
<212> TYPE: PRT
<213> ORGANISM: Mus musculus

<400> SEQUENCE: 36

Glu Gly Tyr Gly Tyr Asp Gly Gly Tyr Phe Asp Tyr
1               5                   10

<210> SEQ ID NO 37
<211> LENGTH: 10
<212> TYPE: PRT
<213> ORGANISM: Mus musculus

<400> SEQUENCE: 37

Gly Tyr Ile Phe Ile Ser Tyr Gly Ile Ser
1               5                   10

<210> SEQ ID NO 38
<211> LENGTH: 17
<212> TYPE: PRT
<213> ORGANISM: Mus musculus

<400> SEQUENCE: 38

-continued

Glu Ile Tyr Pro Arg Ser Gly Lys Thr Tyr Tyr Asn Glu Lys Phe Lys
1               5                   10                  15

Asp

<210> SEQ ID NO 39
<211> LENGTH: 12
<212> TYPE: PRT
<213> ORGANISM: Mus musculus

<400> SEQUENCE: 39

Glu Gly Tyr Gly Tyr Asp Gly Gly Tyr Phe Asp Tyr
1               5                   10

<210> SEQ ID NO 40
<211> LENGTH: 10
<212> TYPE: PRT
<213> ORGANISM: Mus musculus

<400> SEQUENCE: 40

Gly Phe Thr Phe Ser Gly Phe Trp Met Ser
1               5                   10

<210> SEQ ID NO 41
<211> LENGTH: 17
<212> TYPE: PRT
<213> ORGANISM: Mus musculus

<400> SEQUENCE: 41

Asp Ile Asn Ser Asp Gly Ser Ala Ile Ile Tyr Ala Pro Ser Ile Lys
1               5                   10                  15

Asp

<210> SEQ ID NO 42
<211> LENGTH: 11
<212> TYPE: PRT
<213> ORGANISM: Mus musculus

<400> SEQUENCE: 42

Trp Gly Tyr Tyr Gly Ser Asn Tyr Phe Asp Tyr
1               5                   10

<210> SEQ ID NO 43
<211> LENGTH: 10
<212> TYPE: PRT
<213> ORGANISM: Mus musculus

<400> SEQUENCE: 43

Gly Tyr Thr Phe Arg Ser Tyr Gly Ile Thr
1               5                   10

<210> SEQ ID NO 44
<211> LENGTH: 17
<212> TYPE: PRT
<213> ORGANISM: Mus musculus

<400> SEQUENCE: 44

Glu Ile Tyr Pro Arg Ser Gly Lys Thr Tyr Tyr Asn Glu Lys Phe Lys
1               5                   10                  15

Gly

<210> SEQ ID NO 45
<211> LENGTH: 12
<212> TYPE: PRT

```
<213> ORGANISM: Mus musculus

<400> SEQUENCE: 45

Glu Gly Tyr Gly Tyr Asp Gly Gly Tyr Phe Asp Tyr
1               5                   10

<210> SEQ ID NO 46
<211> LENGTH: 10
<212> TYPE: PRT
<213> ORGANISM: Mus musculus

<400> SEQUENCE: 46

Gly Tyr Thr Phe Gly Ser Tyr Gly Ile Thr
1               5                   10

<210> SEQ ID NO 47
<211> LENGTH: 17
<212> TYPE: PRT
<213> ORGANISM: Mus musculus

<400> SEQUENCE: 47

Glu Ile Tyr Pro Arg Ser Gly Lys Thr Tyr Tyr Asn Glu Lys Phe Lys
1               5                   10                  15

Gly

<210> SEQ ID NO 48
<211> LENGTH: 12
<212> TYPE: PRT
<213> ORGANISM: Mus musculus

<400> SEQUENCE: 48

Glu Gly Tyr Gly Tyr Asp Gly Gly Tyr Phe Asp Tyr
1               5                   10

<210> SEQ ID NO 49
<211> LENGTH: 10
<212> TYPE: PRT
<213> ORGANISM: Mus musculus

<400> SEQUENCE: 49

Gly Tyr Thr Phe Arg Ser Tyr Gly Ile Thr
1               5                   10

<210> SEQ ID NO 50
<211> LENGTH: 17
<212> TYPE: PRT
<213> ORGANISM: Mus musculus

<400> SEQUENCE: 50

Glu Ile Tyr Pro Arg Ser Gly Lys Thr Gly Tyr Ala Gln Lys Phe Gln
1               5                   10                  15

Gly

<210> SEQ ID NO 51
<211> LENGTH: 12
<212> TYPE: PRT
<213> ORGANISM: Mus musculus

<400> SEQUENCE: 51

Glu Gly Tyr Gly Tyr Asp Gly Gly Tyr Phe Asp Tyr
1               5                   10

<210> SEQ ID NO 52
```

```
<211> LENGTH: 342
<212> TYPE: DNA
<213> ORGANISM: Mus musculus

<400> SEQUENCE: 52
gatattgtga tgacccagtc tccatcctcc ctggctatgt cagtaggaca gaaggtcact      60
atgagttgca agtccagtca gagccttta aatagtagaa atcaaaagaa ctatttggcc     120
tggtaccagc agaaaccagg acagtctcct aaacttctgg tatactttgc atccactagg    180
gaatctgggg tccctgatcg cttcacaggc agtggatctg ggacagattt cactcttacc    240
atcagcagtg tgcaggctga ggacctggca gtttattact gtcagcaaca ttatagcact    300
cctctcacgt tcggtgctgg gaccaagctg gagctgaaac gg                        342

<210> SEQ ID NO 53
<211> LENGTH: 342
<212> TYPE: DNA
<213> ORGANISM: Mus musculus

<400> SEQUENCE: 53
gatattgtga tgacccagtc tccatcctcc ctggctatgt cagtaggaca gaaggtcgct     60
gtgagctgca agtccagtca gagccttta aatagtagca atcaaaagaa ctatttggcc    120
tggtaccagc agaaaccagg acagtctcct aaacttcttg tatactttgc atccactagg    180
gactctgggg tccctgatcg cttcacaggc agtggatctg ggacagattt cactcttacc    240
atcagcagtg tgcaggctga agacctggca gtttattact gtcagcaaca ttatagcact    300
cctctcacgt tcggtgctgg gaccaagctg gagctgaaac gg                        342

<210> SEQ ID NO 54
<211> LENGTH: 339
<212> TYPE: DNA
<213> ORGANISM: Mus musculus

<400> SEQUENCE: 54
gatgttgtga tgacccaaac tccactctcc ctgcctgtca gtcttggaga tcaagcctcc    60
atctcttgca gatctagtca gagcattgta cacagtaatg gaaacaccta tttacattgg   120
tacctgcaga aaccaggcca gtctccaaag ctcctgatct acagggtttc caaccgattt    180
tctggggtcc cagacaggtt cagtggcagt ggatcaggga cagatttcac actcaagatc    240
agcagagtgg aggctgagga tatgggagtt tattactgct ttcaaggtac acatgttcca    300
ttcacgttcg gctcggggac aaagttggaa ataaaacgg                            339

<210> SEQ ID NO 55
<211> LENGTH: 342
<212> TYPE: DNA
<213> ORGANISM: Mus musculus

<400> SEQUENCE: 55
gacattgtga tgacccagtc tccatcctcc ctggctatgt cagtaggaca gaaggtcact     60
atgagttgca agtccagtca gagccttta aatagtagaa atcaaaagaa ctatttggcc    120
tggtaccagc agaaaccagg acagtctcct aaacttctgg tatactttgc atccactagg    180
gaatctgggg tccctgatcg cttcacaggc agtggatctg ggacagattt cactcttacc    240
atcagcagtg tgcaggctga ggacctggca gtttattact gtcagcaaca ttatagcact    300
cctctcacgt tcggtgctgg gaccaagctg gagctgaaac gg                        342
```

<210> SEQ ID NO 56
<211> LENGTH: 342
<212> TYPE: DNA
<213> ORGANISM: Mus musculus

<400> SEQUENCE: 56

```
gacatcgtga tgacccagtc cccctcctcc ctggccatgt ccgtgggcca gaaagtgacc        60
atgtcctgca gtcctccca gtccctgctg aactcccgga accagaagaa ctacctggcc       120
tggtatcagc agaagcccgg ccagtccccc aagctgctgg tgtacttcgc ctccacccgc       180
gagtccggcg tgcccgatag attcaccggc tccggcagcg gcaccgactt caccctgacc       240
atctccagcg tgcaggccga ggacctggcc gtgtactact gccagcagca ctactccacc       300
cccctgacct tcggcgctgg caccaagctg gaactgaagc gt                         342
```

<210> SEQ ID NO 57
<211> LENGTH: 342
<212> TYPE: DNA
<213> ORGANISM: Mus musculus

<400> SEQUENCE: 57

```
gacatcgtga tgacccagtc cccctcctcc ctggccatgt ccgtgggcga gcgggccacc        60
atcaactgca gtcctccca gtccctgctg aactcccgga accagaagaa ctacctggcc       120
tggtatcagc agaagcccgg ccagcctccc aagctgctga tctacttcgc ctccacccgc       180
gagtccggcg tgcccgatag attctccggc tccggcagcg gcaccgactt caccctgacc       240
atctccagcg tgcaggccga ggacgtggcc gtgtactact gccagcagca ctactccacc       300
cccctgacct tcggcggagg caccaaggtg gaactgaagc gt                         342
```

<210> SEQ ID NO 58
<211> LENGTH: 363
<212> TYPE: DNA
<213> ORGANISM: Mus musculus

<400> SEQUENCE: 58

```
caggttcagc tgcagcagtc tggagttgag gtggcgaggc ctggggcttc agtgaagctg        60
tcctgcaagg cttctggcta caccttcaga agttatggta aacctgggt gaggcagaga       120 actggacagg gccttgagtg gattggagag atttatccta agtggtaa gacttactac       180 aatgagaagt tcaagggcaa ggccacactg actgcagaca catcttccag cacagtgtac       240
atggagctcc gcagcctgac atctgaggac tctgcggtct atttctgtgc aagagagggg       300
tatggttacg acggcggtta ctttgactac tggggccaag gcaccactct cacagtctcc       360
tca                                                                    363
```

<210> SEQ ID NO 59
<211> LENGTH: 363
<212> TYPE: DNA
<213> ORGANISM: Mus musculus

<400> SEQUENCE: 59

```
caggttcagc tgcagcagtc tggagctgag ctggcgaggc ctggggcttc agtgaagctg        60
tcctgcaagg cttctggcta catcttcata agttatggta aagttgggt gaagcagaga       120 actggacagg gccttgagtg gattggagag atttatccta agtgggaa aacttactac       180 aatgagaagt tcaaggacaa ggccgcactg actgcagaca aatcctccag catagcgtac       240
atggagctcc gcagcctgac atctgaggac tctgcggtct atttctgtgc aagagagggg       300
```

```
tatggttacg acggcggtta cttttgactac tggggccaag gcaccatact cacagtctcc    360
tca                                                                   363

<210> SEQ ID NO 60
<211> LENGTH: 360
<212> TYPE: DNA
<213> ORGANISM: Mus musculus

<400> SEQUENCE: 60
gaagtcaagc tggaggagtc tggaggaggc ttggtgcaac ctggggggtc acgggaactc     60
tcttgtgaag gctcagggtt cactttagt ggcttctgga tgagctgggt tcgacagaca    120
cctgggaaga ccctggagtg gattggagac attaattctg atggcagtgc aataatctac    180
gcaccatcca taaaggatcg attcactatc ttcagagaca tgacaagag tacccctgtac    240 ctgcagatga acaatgtgcg atcggaggac acagccacgt atttctgtat gagatggggg    300
tactacggta gtaactactt tgactactgg ggccaaggca ccactctcac agtctcctca    360

<210> SEQ ID NO 61
<211> LENGTH: 363
<212> TYPE: DNA
<213> ORGANISM: Mus musculus

<400> SEQUENCE: 61
caggttcagc tgcagcagtc tggagttgag gtggcgaggc ctggggcttc agtgaagctg     60
tcctgcaagg cttctggcta caccttcaga agttatggta acctgggt gaggcagaga    120 actggacagg gccttgagtg gattggagag atttatccta gaagtggtaa gacttactac    180
aatgagaagt tcaagggcaa ggccacactg actgcagaca catcttccag cacagtgtac    240
atggagctcc gcagcctgac atctgaggac tctgcggtct atttctgtgc aagagagggg    300
tatggttacg acggcggtta cttggactac tggggccaag gcaccactct cacagtctcc    360
tca                                                                   363

<210> SEQ ID NO 62
<211> LENGTH: 363
<212> TYPE: DNA
<213> ORGANISM: Mus musculus

<400> SEQUENCE: 62
caggtgcagc tgcagcagtc cggcgtggaa gtggccagac ctggcgcctc cgtgaagctg     60
tcctgcaagg cctccggcta caccttcggc tcctacggca tcacctgggt gcgacagaga    120
accggccagg gcctggaatg gatcggcgag atctaccctc ggagcggcaa gacctactac    180
aacgagaagt tcaagggcaa ggccaccctg accgccgaca cctcctcctc caccgtgtac    240
atggaactgc ggtccctgac ctccgaggac tccgccgtgt acttctgcgc cagagagggc    300
tacggctacg acggcggcta cttcgactac tggggccagg gcaccaccct gacagtgtcc    360
tcc                                                                   363

<210> SEQ ID NO 63
<211> LENGTH: 363
<212> TYPE: DNA
<213> ORGANISM: Mus musculus

<400> SEQUENCE: 63
caggtgcagc tggtgcagtc cggcgccgaa gtgaagaagc tggcgcctc cgtgaaggtg      60 tcctgcaagg cctccggcta caccttcaga tcctacggca tcacctgggt gcgacaggcc    120
```

```
accggccagg gcctggaatg gatgggcgaa atctaccctc ggagcggcaa gaccggctac      180
gcccagaagt tccagggcag agtgaccatg accgccgaca cctccacctc caccgtgtac      240
atggaactgc ggtccctgcg gtccgaggac tccgccgtgt acttctgcgc cagagagggc      300
tacggctacg acggcggcta cttcgactac tggggccagg gcaccctggt gacagtgtcc      360
tcc                                                                   363
```

```
<210> SEQ ID NO 64
<211> LENGTH: 51
<212> TYPE: DNA
<213> ORGANISM: Mus musculus

<400> SEQUENCE: 64
aagtccagtc agagccttt aaatagtaga atcaaaaga actatttggc c                51
```

```
<210> SEQ ID NO 65
<211> LENGTH: 21
<212> TYPE: DNA
<213> ORGANISM: Mus musculus

<400> SEQUENCE: 65
tttgcatcca ctagggaatc t                                                21
```

```
<210> SEQ ID NO 66
<211> LENGTH: 27
<212> TYPE: DNA
<213> ORGANISM: Mus musculus

<400> SEQUENCE: 66
cagcaacatt atagcactcc tctcacg                                          27
```

```
<210> SEQ ID NO 67
<211> LENGTH: 51
<212> TYPE: DNA
<213> ORGANISM: Mus musculus

<400> SEQUENCE: 67
aagtccagtc agagccttt aaatagtagc aatcaaaaga actatttggc c                51
```

```
<210> SEQ ID NO 68
<211> LENGTH: 21
<212> TYPE: DNA
<213> ORGANISM: Mus musculus

<400> SEQUENCE: 68
tttgcatcca ctagggactc t                                                21
```

```
<210> SEQ ID NO 69
<211> LENGTH: 24
<212> TYPE: DNA
<213> ORGANISM: Mus musculus

<400> SEQUENCE: 69
cagcaacatt atagcactcc tctc                                             24
```

```
<210> SEQ ID NO 70
<211> LENGTH: 48
<212> TYPE: DNA
<213> ORGANISM: Mus musculus

<400> SEQUENCE: 70
```

```
agatctagtc agagcattgt acacagtaat ggaaacacct atttacat              48
```

<210> SEQ ID NO 71
<211> LENGTH: 21
<212> TYPE: DNA
<213> ORGANISM: Mus musculus

<400> SEQUENCE: 71

```
agggtttcca accgattttc t                                           21
```

<210> SEQ ID NO 72
<211> LENGTH: 27
<212> TYPE: DNA
<213> ORGANISM: Mus musculus

<400> SEQUENCE: 72

```
tttcaaggta cacatgttcc attcacg                                     27
```

<210> SEQ ID NO 73
<211> LENGTH: 51
<212> TYPE: DNA
<213> ORGANISM: Mus musculus

<400> SEQUENCE: 73

```
aagtccagtc agagcctttt aaatagtaga atcaaaaga actatttggc c           51
```

<210> SEQ ID NO 74
<211> LENGTH: 21
<212> TYPE: DNA
<213> ORGANISM: Mus musculus

<400> SEQUENCE: 74

```
tttgcatcca ctagggaatc t                                           21
```

<210> SEQ ID NO 75
<211> LENGTH: 27
<212> TYPE: DNA
<213> ORGANISM: Mus musculus

<400> SEQUENCE: 75

```
cagcaacatt atagcactcc tctcacg                                     27
```

<210> SEQ ID NO 76
<211> LENGTH: 51
<212> TYPE: DNA
<213> ORGANISM: Mus musculus

<400> SEQUENCE: 76

```
aagtcctccc agtccctgct gaactcccgg aaccagaaga actacctggc c          51
```

<210> SEQ ID NO 77
<211> LENGTH: 21
<212> TYPE: DNA
<213> ORGANISM: Mus musculus

<400> SEQUENCE: 77

```
ttcgcctcca cccgcgagtc c                                           21
```

<210> SEQ ID NO 78
<211> LENGTH: 27
<212> TYPE: DNA
<213> ORGANISM: Mus musculus

<400> SEQUENCE: 78
cagcagcact actccacccc cctgacc                              27

<210> SEQ ID NO 79
<211> LENGTH: 51
<212> TYPE: DNA
<213> ORGANISM: Mus musculus

<400> SEQUENCE: 79
aagtcctccc agtccctgct gaactcccgg aaccagaaga actacctggc c    51

<210> SEQ ID NO 80
<211> LENGTH: 21
<212> TYPE: DNA
<213> ORGANISM: Mus musculus

<400> SEQUENCE: 80
ttcgcctcca cccgcgagtc c                                    21

<210> SEQ ID NO 81
<211> LENGTH: 27
<212> TYPE: DNA
<213> ORGANISM: Mus musculus

<400> SEQUENCE: 81
cagcagcact actccacccc cctgacc                              27

<210> SEQ ID NO 82
<211> LENGTH: 30
<212> TYPE: DNA
<213> ORGANISM: Mus musculus

<400> SEQUENCE: 82
ggctacacct tcagaagtta tggtataacc                           30

<210> SEQ ID NO 83
<211> LENGTH: 51
<212> TYPE: DNA
<213> ORGANISM: Mus musculus

<400> SEQUENCE: 83
gagatttatc ctagaagtgg taagacttac tacaatgaga agttcaaggg c    51

<210> SEQ ID NO 84
<211> LENGTH: 36
<212> TYPE: DNA
<213> ORGANISM: Mus musculus

<400> SEQUENCE: 84
gaggggtatg gttacgacgg cggttacttt gactac                    36

<210> SEQ ID NO 85
<211> LENGTH: 30
<212> TYPE: DNA
<213> ORGANISM: Mus musculus

<400> SEQUENCE: 85
ggctacatct tcataagtta tggtataagt                           30

<210> SEQ ID NO 86
<211> LENGTH: 51
<212> TYPE: DNA
<213> ORGANISM: Mus musculus

<400> SEQUENCE: 86
gagatttatc ctagaagtgg gaaaacttac tacaatgaga agttcaagga c         51

<210> SEQ ID NO 87
<211> LENGTH: 36
<212> TYPE: DNA
<213> ORGANISM: Mus musculus

<400> SEQUENCE: 87
gaggggtatg gttacgacgg cggttacttt gactac                          36

<210> SEQ ID NO 88
<211> LENGTH: 30
<212> TYPE: DNA
<213> ORGANISM: Mus musculus

<400> SEQUENCE: 88
gggttcactt ttagtggctt ctggatgagc                                 30

<210> SEQ ID NO 89
<211> LENGTH: 51
<212> TYPE: DNA
<213> ORGANISM: Mus musculus

<400> SEQUENCE: 89
gacattaatt ctgatggcag tgcaataatc tacgcaccat ccataaagga t         51

<210> SEQ ID NO 90
<211> LENGTH: 33
<212> TYPE: DNA
<213> ORGANISM: Mus musculus

<400> SEQUENCE: 90
tgggggtact acggtagtaa ctactttgac tac                             33

<210> SEQ ID NO 91
<211> LENGTH: 30
<212> TYPE: DNA
<213> ORGANISM: Mus musculus

<400> SEQUENCE: 91
ggctacacct tcagaagtta tggtataacc                                 30

<210> SEQ ID NO 92
<211> LENGTH: 51
<212> TYPE: DNA
<213> ORGANISM: Mus musculus

<400> SEQUENCE: 92
gagatttatc ctagaagtgg taagacttac tacaatgaga agttcaaggg c         51

<210> SEQ ID NO 93
<211> LENGTH: 36
<212> TYPE: DNA
<213> ORGANISM: Mus musculus

<400> SEQUENCE: 93
gaggggtatg gttacgacgg cggttacttt gactac                          36

<210> SEQ ID NO 94
<211> LENGTH: 30
<212> TYPE: DNA
<213> ORGANISM: Mus musculus

```
<400> SEQUENCE: 94
ggctacacct tcggctccta cggcatcacc                                          30

<210> SEQ ID NO 95
<211> LENGTH: 51
<212> TYPE: DNA
<213> ORGANISM: Mus musculus

<400> SEQUENCE: 95
gagatctacc ctcggagcgg caagacctac tacaacgaga agttcaaggg c                  51

<210> SEQ ID NO 96
<211> LENGTH: 36
<212> TYPE: DNA
<213> ORGANISM: Mus musculus

<400> SEQUENCE: 96
gagggctacg gctacgacgg cggctacttc gactac                                   36

<210> SEQ ID NO 97
<211> LENGTH: 30
<212> TYPE: DNA
<213> ORGANISM: Mus musculus

<400> SEQUENCE: 97
ggctacacct tcagatccta cggcatcacc                                          30

<210> SEQ ID NO 98
<211> LENGTH: 51
<212> TYPE: DNA
<213> ORGANISM: Mus musculus

<400> SEQUENCE: 98
gaaatctacc ctcggagcgg caagaccggc tacgcccaga agttccaggg c                  51

<210> SEQ ID NO 99
<211> LENGTH: 36
<212> TYPE: DNA
<213> ORGANISM: Mus musculus

<400> SEQUENCE: 99
gagggctacg gctacgacgg cggctacttc gactac                                   36

<210> SEQ ID NO 100
<211> LENGTH: 12
<212> TYPE: PRT
<213> ORGANISM: artificial
<220> FEATURE:
<223> OTHER INFORMATION: synthetic

<400> SEQUENCE: 100

Asp Val Ala Leu Glu His His Glu Glu Cys Asp Cys
1               5                   10

<210> SEQ ID NO 101
<211> LENGTH: 7
<212> TYPE: PRT
<213> ORGANISM: artificial
<220> FEATURE:
<223> OTHER INFORMATION: synthetic

<400> SEQUENCE: 101

Leu Leu Thr Glu Glu Val Arg
```

<210> SEQ ID NO 102
<211> LENGTH: 9
<212> TYPE: PRT
<213> ORGANISM: artificial
<220> FEATURE:
<223> OTHER INFORMATION: synthetic

<400> SEQUENCE: 102

Val Thr Lys Lys Tyr His Glu Val Leu
1               5

<210> SEQ ID NO 103
<211> LENGTH: 345
<212> TYPE: PRT
<213> ORGANISM: artificial
<220> FEATURE:
<223> OTHER INFORMATION: synthetic

<400> SEQUENCE: 103

Met Leu Leu Leu Gly Leu Leu Leu Thr Ser Ala Leu Ala Gly Gln
1               5                   10                  15

Arg Thr Gly Thr Arg Ala Glu Ser Asn Leu Ser Ser Lys Leu Gln Leu
            20                  25                  30

Ser Ser Asp Lys Glu Gln Asn Gly Val Gln Asp Pro Arg His Glu Arg
        35                  40                  45

Val Val Thr Ile Ser Gly Asn Gly Ser Ile His Ser Pro Lys Phe Pro
    50                  55                  60

His Thr Tyr Pro Arg Asn Met Val Leu Val Trp Arg Leu Val Ala Val
65                  70                  75                  80

Asp Glu Asn Val Arg Ile Gln Leu Thr Phe Asp Glu Arg Phe Gly Leu
                85                  90                  95

Glu Asp Pro Glu Asp Asp Ile Cys Lys Tyr Asp Phe Val Glu Val Glu
            100                 105                 110

Glu Pro Ser Asp Gly Ser Val Leu Gly Arg Trp Cys Gly Ser Gly Thr
        115                 120                 125

Val Pro Gly Lys Gln Thr Ser Lys Gly Asn His Ile Arg Ile Arg Phe
    130                 135                 140

Val Ser Asp Glu Tyr Phe Pro Ser Glu Pro Gly Phe Cys Ile His Tyr
145                 150                 155                 160

Ser Ile Ile Met Pro Gln Val Thr Glu Thr Thr Ser Pro Ser Val Leu
                165                 170                 175

Pro Pro Ser Ser Leu Ser Leu Asp Leu Leu Asn Asn Ala Val Thr Ala
            180                 185                 190

Phe Ser Thr Leu Glu Glu Leu Ile Arg Tyr Leu Glu Pro Asp Arg Trp
        195                 200                 205

Gln Val Asp Leu Asp Ser Leu Tyr Lys Pro Thr Trp Gln Leu Leu Gly
    210                 215                 220

Lys Ala Phe Leu Tyr Gly Lys Lys Ser Lys Val Val Asn Leu Asn Leu
225                 230                 235                 240

Leu Thr Glu Glu Val Arg Leu Tyr Ser Cys Thr Pro Arg Asn Phe Ser
                245                 250                 255

Val Ser Ile Arg Glu Glu Leu Lys Arg Thr Asp Thr Ile Phe Trp Pro
            260                 265                 270

Gly Cys Leu Leu Val Lys Arg Cys Gly Gly Asn Cys Ala Cys Cys Leu
        275                 280                 285

His Asn Cys Asn Glu Cys Gln Cys Val Pro Ser Lys Val Thr Lys Lys
290                 295                 300

Tyr His Glu Val Leu Gln Leu Arg Pro Lys Thr Gly Val Arg Gly Leu
305                 310                 315                 320

His Lys Ser Leu Thr Asp Val Ala Leu Glu His His Glu Glu Cys Asp
            325                 330                 335

Cys Val Cys Arg Gly Ser Thr Gly Gly
            340             345

<210> SEQ ID NO 104
<211> LENGTH: 345
<212> TYPE: PRT
<213> ORGANISM: Mus musculus

<400> SEQUENCE: 104

Met Leu Leu Leu Gly Leu Leu Leu Thr Ser Ala Leu Ala Gly Gln
1               5                   10                  15

Arg Thr Gly Thr Arg Ala Glu Ser Asn Leu Ser Ser Lys Leu Gln Leu
            20                  25                  30

Ser Ser Asp Lys Glu Gln Asn Gly Val Gln Asp Pro Arg His Glu Arg
            35                  40                  45

Val Val Thr Ile Ser Gly Asn Gly Ser Ile His Ser Pro Lys Phe Pro
50                  55                  60

His Thr Tyr Pro Arg Asn Met Val Leu Val Trp Arg Leu Val Ala Val
65                  70                  75                  80

Asp Glu Asn Val Arg Ile Gln Leu Thr Phe Asp Glu Arg Phe Gly Leu
                85                  90                  95

Glu Asp Pro Glu Asp Asp Ile Cys Lys Tyr Asp Phe Val Glu Val Glu
            100                 105                 110

Glu Pro Ser Asp Gly Ser Val Leu Gly Arg Trp Cys Gly Ser Gly Thr
            115                 120                 125

Val Pro Gly Lys Gln Thr Ser Lys Gly Asn His Ile Arg Ile Arg Phe
130                 135                 140

Val Ser Asp Glu Tyr Phe Pro Ser Glu Pro Gly Phe Cys Ile His Tyr
145                 150                 155                 160

Ser Ile Ile Met Pro Gln Val Thr Glu Thr Thr Ser Pro Ser Val Leu
                165                 170                 175

Pro Pro Ser Ser Leu Ser Leu Asp Leu Leu Asn Asn Ala Val Thr Ala
            180                 185                 190

Phe Ser Thr Leu Glu Glu Leu Ile Arg Tyr Leu Glu Pro Asp Arg Trp
            195                 200                 205

Gln Val Asp Leu Asp Ser Leu Tyr Lys Pro Thr Trp Gln Leu Leu Gly
210                 215                 220

Lys Ala Phe Leu Tyr Gly Lys Lys Ser Lys Val Val Asn Leu Asn Leu
225                 230                 235                 240

Leu Lys Glu Glu Val Lys Leu Tyr Ser Cys Thr Pro Arg Asn Phe Ser
                245                 250                 255

Val Ser Ile Arg Glu Glu Leu Lys Arg Thr Asp Thr Ile Phe Trp Pro
            260                 265                 270

Gly Cys Leu Leu Val Lys Arg Cys Gly Gly Asn Cys Ala Cys Cys Leu
            275                 280                 285

His Asn Cys Asn Glu Cys Gln Cys Val Pro Arg Lys Val Thr Lys Lys
290                 295                 300

Tyr His Glu Val Leu Gln Leu Arg Pro Lys Thr Gly Val Lys Gly Leu
305                 310                 315                 320

```
His Lys Ser Leu Thr Asp Val Ala Leu Glu His His Glu Glu Cys Asp
            325                 330                 335

Cys Val Cys Arg Gly Asn Ala Gly Gly
        340                 345

<210> SEQ ID NO 105
<211> LENGTH: 10
<212> TYPE: PRT
<213> ORGANISM: artificial
<220> FEATURE:
<223> OTHER INFORMATION: synthetic

<400> SEQUENCE: 105

Ser Val Ser Ile Arg Glu Glu Leu Lys Cys
1               5                   10

<210> SEQ ID NO 106
<211> LENGTH: 10
<212> TYPE: PRT
<213> ORGANISM: artificial
<220> FEATURE:
<223> OTHER INFORMATION: synthetic

<400> SEQUENCE: 106

Arg Thr Asp Thr Ile Phe Trp Pro Gly Cys
1               5                   10

<210> SEQ ID NO 107
<211> LENGTH: 11
<212> TYPE: PRT
<213> ORGANISM: artificial
<220> FEATURE:
<223> OTHER INFORMATION: synthetic

<400> SEQUENCE: 107

Glu Glu Leu Lys Arg Thr Asp Thr Ile Phe Cys
1               5                   10

<210> SEQ ID NO 108
<211> LENGTH: 10
<212> TYPE: PRT
<213> ORGANISM: artificial
<220> FEATURE:
<223> OTHER INFORMATION: synthetic

<400> SEQUENCE: 108

Ser Val Asn Ile Arg Glu Glu Leu Lys Cys
1               5                   10

<210> SEQ ID NO 109
<211> LENGTH: 116
<212> TYPE: PRT
<213> ORGANISM: Mus musculus

<400> SEQUENCE: 109

Gly Lys Lys Ser Lys Val Val Asn Leu Asn Leu Leu Lys Glu Glu Val
1               5                   10                  15

Lys Leu Tyr Ser Cys Thr Pro Arg Asn Phe Ser Val Ser Ile Arg Glu
                20                  25                  30

Glu Leu Lys Arg Thr Asp Thr Ile Phe Trp Pro Gly Cys Leu Leu Val
            35                  40                  45
```

-continued

Lys Arg Cys Gly Gly Asn Cys Ala Cys Cys Leu His Asn Cys Asn Glu
        50                  55                  60

Cys Gln Cys Val Pro Arg Lys Val Thr Lys Lys Tyr His Glu Val Leu
65                  70                  75                  80

Gln Leu Arg Pro Lys Thr Gly Val Lys Gly Leu His Lys Ser Leu Thr
                85                  90                  95

Asp Val Ala Leu Glu His His Glu Glu Cys Asp Cys Val Cys Arg Gly
                100                 105                 110

Asn Ala Gly Gly
        115

<210> SEQ ID NO 110
<211> LENGTH: 81
<212> TYPE: PRT
<213> ORGANISM: Homo sapiens

<400> SEQUENCE: 110

Gly Arg Lys Ser Arg Val Val Asp Leu Asn Leu Thr Glu Glu Val
1               5                   10                  15

Arg Leu Tyr Ser Cys Thr Pro Arg Asn Phe Ser Val Ser Ile Arg Glu
                20                  25                  30

Glu Leu Lys Arg Thr Asp Thr Ile Phe Trp Pro Gly Cys Leu Leu Val
                35                  40                  45

Lys Arg Cys Gly Gly Asn Cys Ala Cys Cys Leu His Asn Cys Asn Glu
        50                  55                  60

Cys Gln Cys Val Pro Ser Lys Ala Val Thr Lys Lys Tyr His Glu Val
65                  70                  75                  80

Leu

<210> SEQ ID NO 111
<211> LENGTH: 121
<212> TYPE: PRT
<213> ORGANISM: artificial
<220> FEATURE:
<223> OTHER INFORMATION: synthetic

<400> SEQUENCE: 111

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Gly Ser Tyr
                20                  25                  30

Gly Ile Thr Trp Val Arg Gln Ala Thr Gly Gln Gly Leu Glu Trp Met
            35                  40                  45

Gly Glu Ile Tyr Pro Arg Ser Gly Lys Thr Gly Tyr Ala Gln Lys Phe
        50                  55                  60

Gln Gly Arg Val Thr Met Thr Ala Asp Thr Ser Thr Ser Thr Val Tyr
65                  70                  75                  80

Met Glu Leu Arg Ser Leu Arg Ser Glu Asp Ser Ala Val Tyr Phe Cys
                85                  90                  95

Ala Arg Glu Gly Tyr Gly Tyr Asp Gly Gly Tyr Phe Asp Tyr Trp Gly
                100                 105                 110

Gln Gly Thr Leu Val Thr Val Ser Ser
        115                 120